US010603360B2

(12) United States Patent
Gerdes et al.

(10) Patent No.: US 10,603,360 B2
(45) Date of Patent: *Mar. 31, 2020

(54) COMBINATION IL-2 IMMUNOCONJUGATE THERAPY

(71) Applicant: Roche Glycart AG, Schlieren (CH)

(72) Inventors: Christian Gerdes, Erlenbach (CH); Christian Klein, Bonstetten (CH); Valeria G. Nicolini, Erlenbach (CH); Pablo Umana, Wollerau (CH)

(73) Assignee: Roche Glycart AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/353,587

(22) Filed: Nov. 16, 2016

(65) Prior Publication Data

US 2017/0056522 A1    Mar. 2, 2017

Related U.S. Application Data

(63) Continuation of application No. 13/961,649, filed on Aug. 7, 2013, now Pat. No. 9,526,797.

(30) Foreign Application Priority Data

Aug. 7, 2012 (EP) .................................. 12179473

(51) Int. Cl.
| | | |
|---|---|---|
| A61K 38/20 | (2006.01) | |
| A61K 39/00 | (2006.01) | |
| A61K 45/06 | (2006.01) | |
| A61K 47/64 | (2017.01) | |
| A61K 47/68 | (2017.01) | |
| C07K 16/28 | (2006.01) | |
| C07K 16/30 | (2006.01) | |
| C07K 16/32 | (2006.01) | |
| C07K 16/40 | (2006.01) | |

(52) U.S. Cl.
CPC .......... *A61K 38/2013* (2013.01); *A61K 45/06* (2013.01); *A61K 47/642* (2017.08); *A61K 47/6849* (2017.08); *A61K 47/6853* (2017.08); *C07K 16/2863* (2013.01); *C07K 16/30* (2013.01); *C07K 16/3007* (2013.01); *C07K 16/32* (2013.01); *C07K 16/40* (2013.01); *A61K 2039/505* (2013.01); *A61K 2039/507* (2013.01); *C07K 2317/24* (2013.01); *C07K 2317/33* (2013.01); *C07K 2317/41* (2013.01); *C07K 2317/71* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| 8,288,030 B2 | 10/2012 | Dong et al. | |
|---|---|---|---|
| 9,526,797 B2 * | 12/2016 | Gerdes | ............... C07K 16/2863 |

FOREIGN PATENT DOCUMENTS

| WO | 2004/099249 A2 | 11/2004 |
|---|---|---|
| WO | 2005/044859 A2 | 5/2005 |
| WO | 2005/100402 A1 | 10/2005 |
| WO | 2008/003473 A2 | 1/2008 |
| WO | 2008/143954 A2 | 11/2008 |
| WO | 2011/001276 A1 | 1/2011 |
| WO | 2011/076683 A1 | 6/2011 |
| WO | 2011/101328 A2 | 8/2011 |
| WO | 2011/111254 A1 | 9/2011 |
| WO | 2012/020038 A1 | 2/2012 |
| WO | 2012/107416 A2 | 8/2012 |
| WO | 2012/130831 A1 | 10/2012 |
| WO | 2012/146628 A1 | 11/2012 |

OTHER PUBLICATIONS

Bork et al., "Powers and Pitfalls in Sequence Analysis: the 70% Hurdle" Genorme Res. 10:398-400 (2000).
Bowie et al., "Deciphering the message in protein sequences: tolerance to amino acid substitutions" Science 247:1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" Journal of Cell Biology 111:2129-2138 (Nov. 1990).
Gillies et al., "Improving the Efficacy of Antibody-Interleukin 2 Fusion Proteins by Reducing Their Interaction with Fc Receptors" Cancer Research 59(9):2159-2166 (1999).
Hezareh, M. et al., "Effector function activities of a panel of mutants of a broadly neutralizing antibody against human immunodeficiency virus type 1" J VIROL 75(24):12161-12168 (2001).
International Search Report dated Oct. 28, 2013, for PCT Patent Application No. PCT/EP2013/066351 filed on Aug. 5, 2013.
Lazar et al., "Transforming Growth Factor α: Mutation of Aspartic Acid 47 and Leucine 48 Results in Different Biological Activities" Molecular & Cellular Biology 8(3):1247-1252 (Mar. 1988).
Ogura et al., "Phase 1 study of anti-CD22 immunoconjugate inotuzumab ozogamicin plus rituximab in relapsed/refractory B-cell non-hodgkin lymphoma" Cancer Science 103(5):933-938 (May 2012).
Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).

\* cited by examiner

*Primary Examiner* — Brian Gangle
*Assistant Examiner* — Andrea K McCollum

(57) ABSTRACT

The present invention provides combinations of (a) an immunoconjugate comprising a first antibody engineered to have reduced effector function and an effector moiety, and (b) a second antibody engineered to have increased effector function, for use in treating a disease in an individual in need thereof. Further provided are pharmaceutical compositions comprising the combinations, and methods of using them.

22 Claims, 13 Drawing Sheets

Figure 1A:
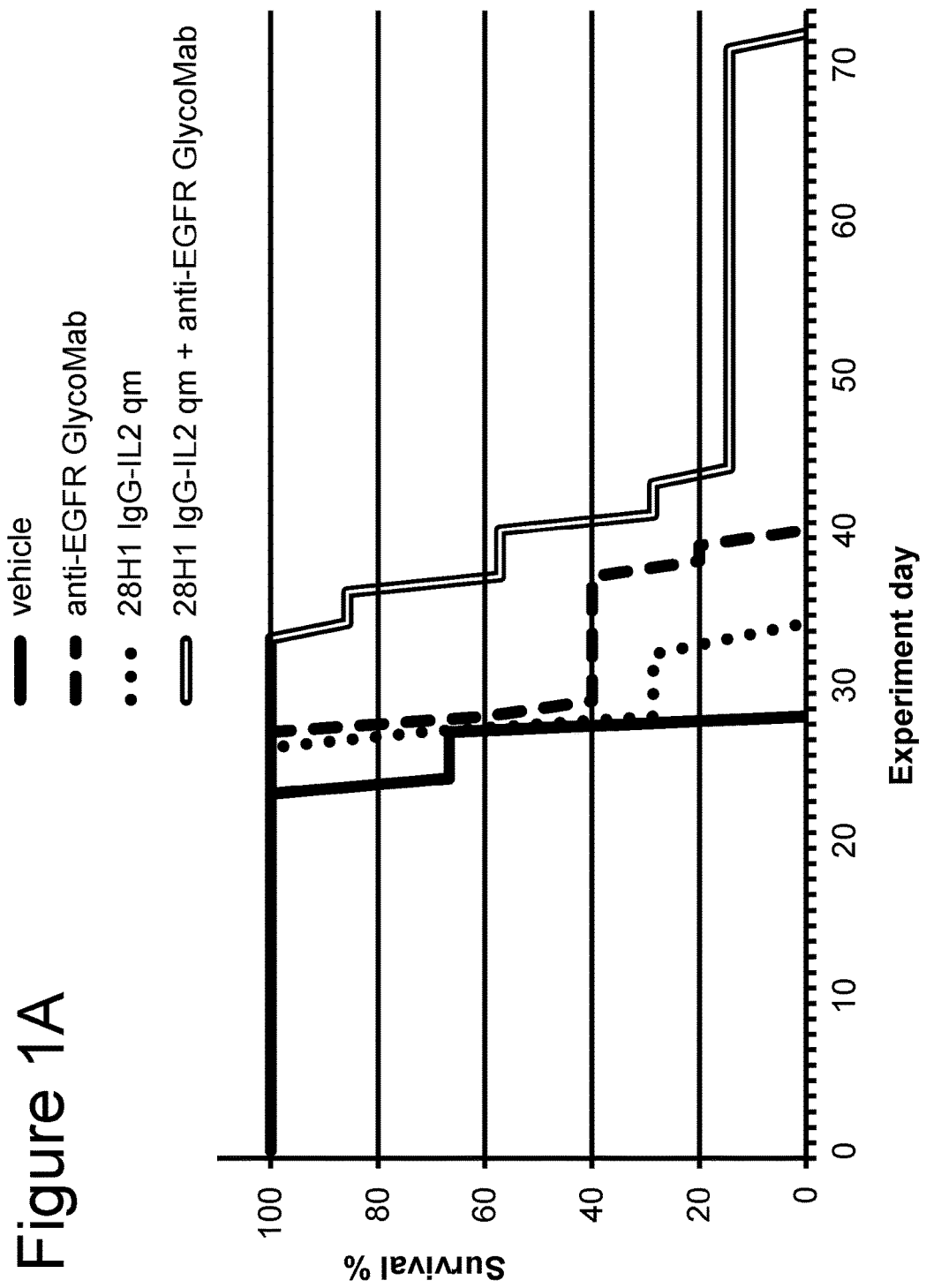

Specification includes a Sequence Listing.

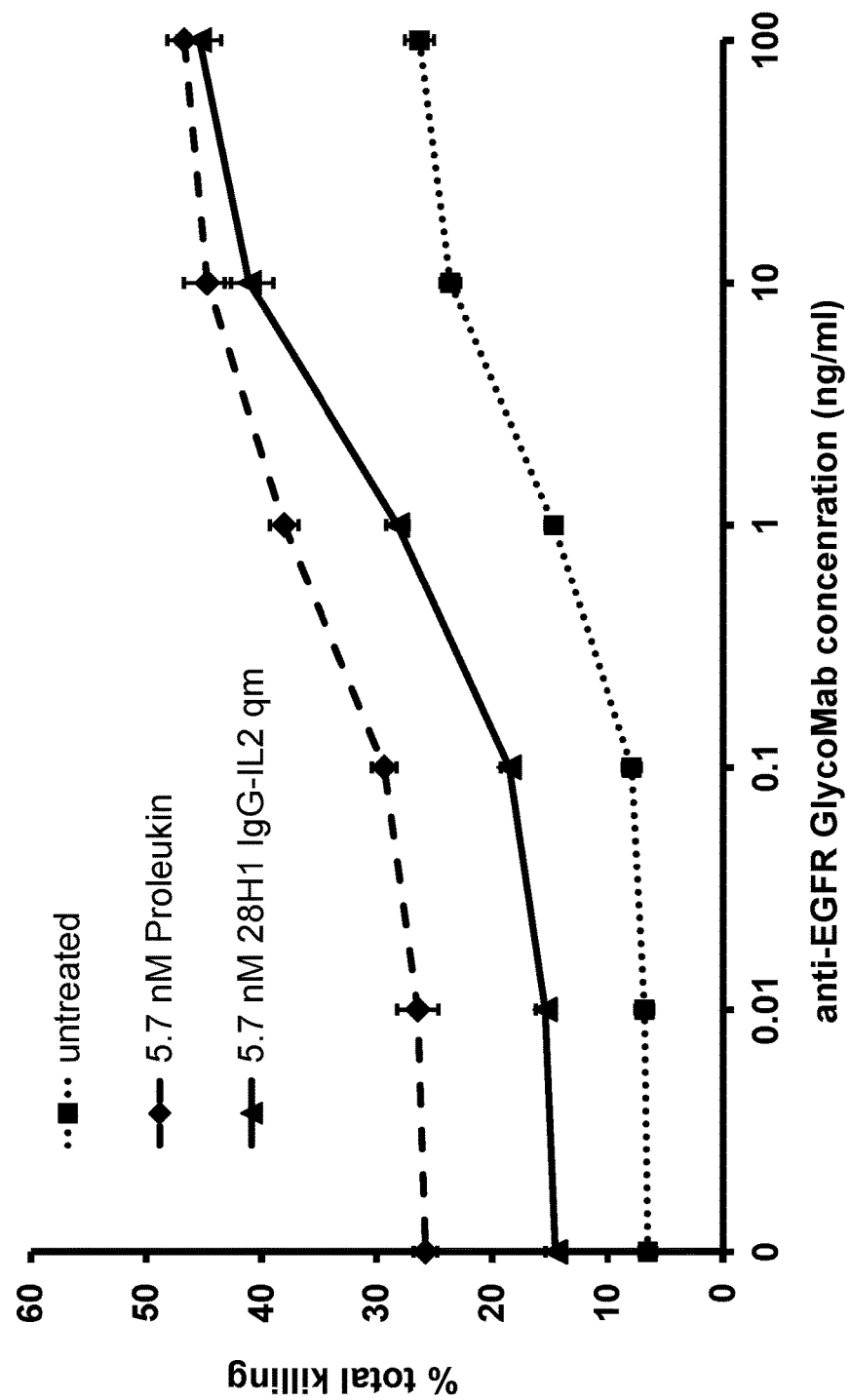

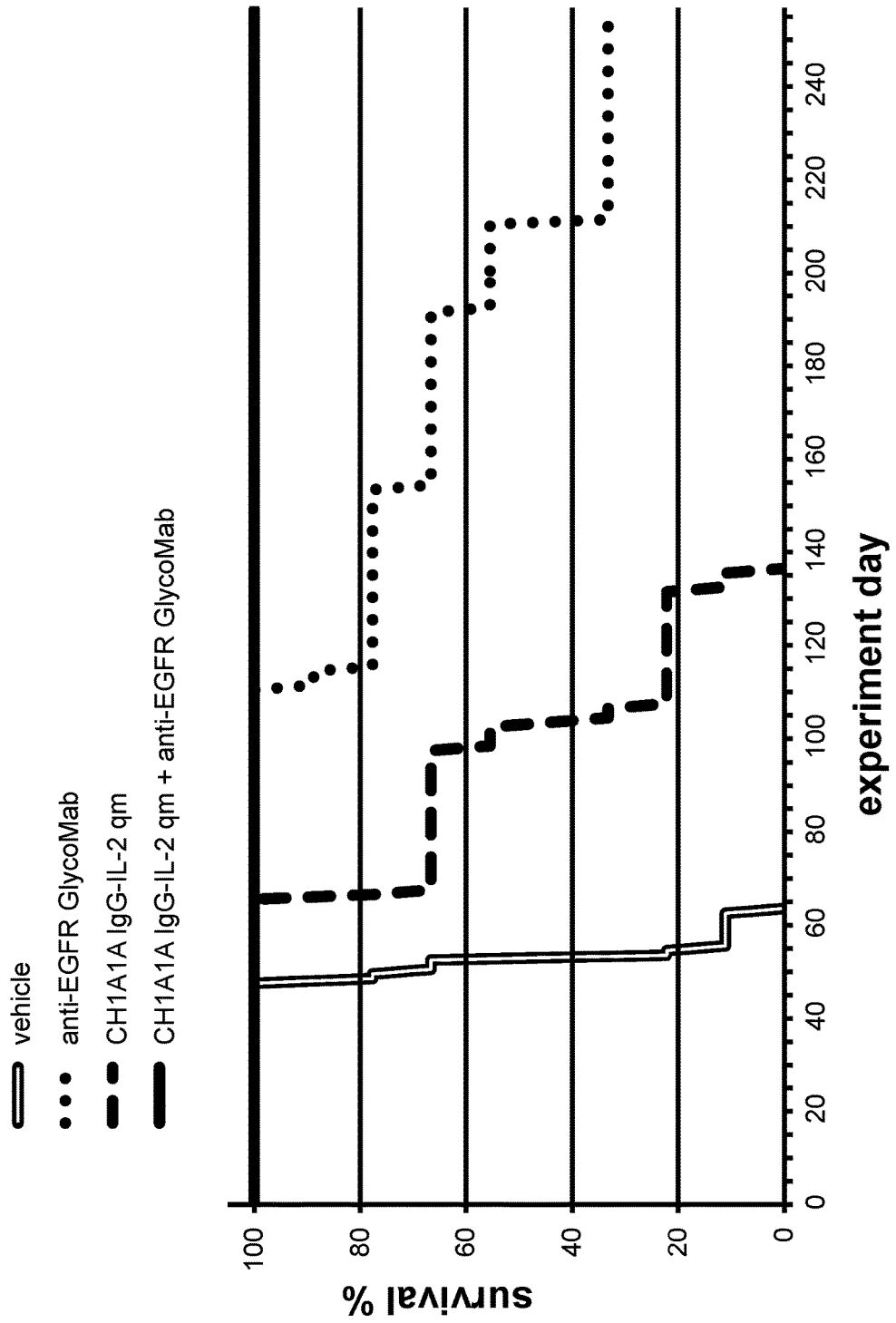

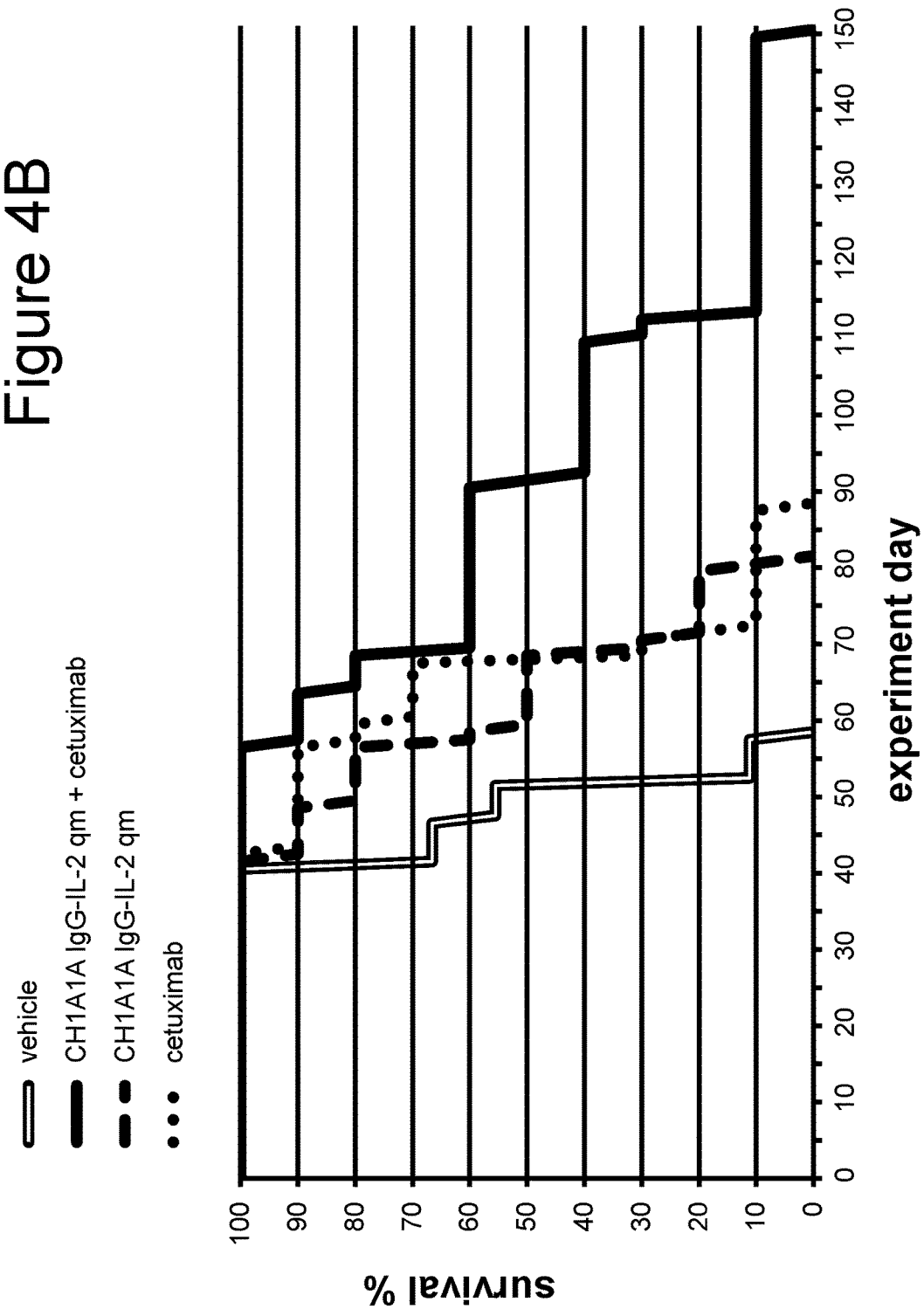

SEQUENCE LISTING

```
<160> NUMBER OF SEQ ID NOS: 146

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

-continued

```
<210> SEQ ID NO 2
<211> LENGTH: 133
<212> TYPE: PRT
<213> ORGANISM: Homo sapiens

<400> SEQUENCE: 2

Ala Pro Ala Ser Ser Thr Lys Lys Thr Gln Leu Gln Leu Glu His
1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 3
<211> LENGTH: 107
<212> TYPE: PRT
<213> ORGANISM: Artificial Sequence
<220> FEATURE:
<223> OTHER INFORMATION: 2B10; VL

<400> SEQUENCE: 3

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: 2B10(GS); VL
```

-continued

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: 2B10; VH

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 6
<211> LENGTH: 108
<212> TYPE: PRT
<213> ORGANISM: Artificial Sequence
<220> FEATURE:
<223> OTHER INFORMATION: 2F11; VL

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Tyr Thr Pro
                85                  90                  95

Pro Thr Phe Gly Gln Gly Thr Lys Val Glu Ile Lys
            100                 105

<210> SEQ ID NO 7
<211> LENGTH: 108
<212> TYPE: PRT
<213> ORGANISM: Artificial Sequence
<220> FEATURE:
<223> OTHER INFORMATION: 2F11(VI); VL

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Tyr Thr Pro
                85                  90                  95

Pro Thr Phe Gly Gln Gly Thr Lys Val Glu Ile Lys
            100                 105

<210> SEQ ID NO 8
<211> LENGTH: 117
<212> TYPE: PRT
<213> ORGANISM: Artificial Sequence
<220> FEATURE:
<223> OTHER INFORMATION: 2F11; VH

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
            115

<210> SEQ ID NO 9
<211> LENGTH: 117
<212> TYPE: PRT
<213> ORGANISM: Artificial Sequence
```

```
<220> FEATURE:
<223> OTHER INFORMATION: 2F11(MT); VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
            115

<210> SEQ ID NO 10
<211> LENGTH: 108
<212> TYPE: PRT
<213> ORGANISM: Artificial Sequence
<220> FEATURE:
<223> OTHER INFORMATION: 3F2; VL

<400> SEQUENCE: 10

Glu Ile Val Leu Thr Gln Ser Pro Gly Thr Leu Ser Leu Tyr Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 11
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45
```

```
Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys
            100                 105
```

<210> SEQ ID NO 12
<211> LENGTH: 117
<212> TYPE: PRT
<213> ORGANISM: Artificial Sequence
<220> FEATURE:
<223> OTHER INFORMATION: 3F2; VH

<400> SEQUENCE: 12

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Gly Phe Asn Tyr Trp Gly Gln Gly Thr Leu
            100                 105                 110

Val Thr Val Ser Ser
            115
```

<210> SEQ ID NO 13
<211> LENGTH: 108
<212> TYPE: PRT
<213> ORGANISM: Artificial Sequence
<220> FEATURE:
<223> OTHER INFORMATION: 3D9, VL

<400> SEQUENCE: 13

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Leu Ile Pro
                 85                  90                  95

Pro Thr Phe Gly Gln Gly Thr Lys Val Glu Ile Lys
            100                 105
```

```
<210> SEQ ID NO 14
<211> LENGTH: 117
<212> TYPE: PRT
<213> ORGANISM: Artificial Sequence
<220> FEATURE:
<223> OTHER INFORMATION: 3D9, VH

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: 3D9(TA); VH

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: 4G8; VL
```

-continued

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 17
<211> LENGTH: 117
<212> TYPE: PRT
<213> ORGANISM: Artificial Sequence
<220> FEATURE:
<223> OTHER INFORMATION: 4G8; VH

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

<210> SEQ ID NO 18
<211> LENGTH: 108
<212> TYPE: PRT
<213> ORGANISM: Artificial Sequence
<220> FEATURE:
<223> OTHER INFORMATION: 4B3; VL

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 19
<211> LENGTH: 117
<212> TYPE: PRT
<213> ORGANISM: Artificial Sequence
<220> FEATURE:
<223> OTHER INFORMATION: 4B3; VH

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115
```

<210> SEQ ID NO 20
<211> LENGTH: 108
<212> TYPE: PRT
<213> ORGANISM: Artificial Sequence
<220> FEATURE:
<223> OTHER INFORMATION: 4D6; VL

<400> SEQUENCE: 20

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
            35                  40                  45

Ile Gln Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 21
<211> LENGTH: 117
<212> TYPE: PRT
<213> ORGANISM: Artificial Sequence

<220> FEATURE:
<223> OTHER INFORMATION: 4D6; VH

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

<210> SEQ ID NO 22
<211> LENGTH: 108
<212> TYPE: PRT
<213> ORGANISM: Artificial Sequence
<220> FEATURE:
<223> OTHER INFORMATION: 2C6; VL

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: 2C6; VH

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Ala Gly Tyr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Asn Phe Asp Tyr Trp Gly Gln Gly Thr Leu
                100                 105                 110

Val Thr Val Ser Ser
            115
```

<210> SEQ ID NO 24
<211> LENGTH: 108
<212> TYPE: PRT
<213> ORGANISM: Artificial Sequence
<220> FEATURE:
<223> OTHER INFORMATION: 5H5; VL

<400> SEQUENCE: 24

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Asn Gln Ile Pro
                 85                  90                  95

Pro Thr Phe Gly Gln Gly Thr Lys Val Glu Ile Lys
                100                 105
```

<210> SEQ ID NO 25
<211> LENGTH: 116
<212> TYPE: PRT
<213> ORGANISM: Artificial Sequence
<220> FEATURE:
<223> OTHER INFORMATION: 5H5; VH

<400> SEQUENCE: 25

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Thr Met Ser Trp Val Arg Arg Ser Pro Gly Lys Gly Leu Glu Trp Val
             35                  40                  45

Ser Ala Ile Ser Gly Gly Gly Arg Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gly Trp Phe Thr Pro Phe Asp Tyr Trp Gly Gln Gly Thr Leu Val
                100                 105                 110

Thr Val Ser Ser
            115
```

```
<210> SEQ ID NO 26
<211> LENGTH: 108
<212> TYPE: PRT
<213> ORGANISM: Artificial Sequence
<220> FEATURE:
<223> OTHER INFORMATION: 2C4; VL

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105

<210> SEQ ID NO 27
<211> LENGTH: 117
<212> TYPE: PRT
<213> ORGANISM: Artificial Sequence
<220> FEATURE:
<223> OTHER INFORMATION: 2C4; VH

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115

<210> SEQ ID NO 28
<211> LENGTH: 108
<212> TYPE: PRT
<213> ORGANISM: Artificial Sequence
<220> FEATURE:
<223> OTHER INFORMATION: 2D9; VL

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Asn Gln Ile Pro
                 85                  90                  95

Pro Thr Phe Gly Gln Gly Thr Lys Val Glu Ile Lys
                100                 105

<210> SEQ ID NO 29
<211> LENGTH: 117
<212> TYPE: PRT
<213> ORGANISM: Artificial Sequence
<220> FEATURE:
<223> OTHER INFORMATION: 2D9; VH

<400> SEQUENCE: 29

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Thr Pro Phe Asp Tyr Trp Gly Gln Gly Thr Leu
                100                 105                 110

Val Thr Val Ser Ser
        115

<210> SEQ ID NO 30
<211> LENGTH: 108
<212> TYPE: PRT
<213> ORGANISM: Artificial Sequence
<220> FEATURE:
<223> OTHER INFORMATION: 4B8; VL

<400> SEQUENCE: 30

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys
                100                 105

-continued

```
<210> SEQ ID NO 31
<211> LENGTH: 117
<212> TYPE: PRT
<213> ORGANISM: Artificial Sequence
<220> FEATURE:
<223> OTHER INFORMATION: 4B8; VH

<400> SEQUENCE: 31
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

```
<210> SEQ ID NO 32
<211> LENGTH: 108
<212> TYPE: PRT
<213> ORGANISM: Artificial Sequence
<220> FEATURE:
<223> OTHER INFORMATION: 7A1; VL

<400> SEQUENCE: 32
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105

```
<210> SEQ ID NO 33
<211> LENGTH: 117
<212> TYPE: PRT
<213> ORGANISM: Artificial Sequence
<220> FEATURE:
<223> OTHER INFORMATION: 7A1; VH

<400> SEQUENCE: 33
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Asn Phe Asp Tyr Trp Gly Gln Gly Thr Leu
                100                 105                 110

Val Thr Val Ser Ser
            115

<210> SEQ ID NO 34
<211> LENGTH: 108
<212> TYPE: PRT
<213> ORGANISM: Artificial Sequence
<220> FEATURE:
<223> OTHER INFORMATION: 13C2; VL

<400> SEQUENCE: 34

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Leu Ile Pro
                 85                  90                  95

Pro Thr Phe Gly Gln Gly Thr Lys Val Glu Ile Lys
                100                 105

<210> SEQ ID NO 35
<211> LENGTH: 117
<212> TYPE: PRT
<213> ORGANISM: Artificial Sequence
<220> FEATURE:
<223> OTHER INFORMATION: 13C2; VH

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Gly Trp Leu Gly Pro Phe Asp Tyr Trp Gly Gln Gly Thr Leu
                100                 105                 110

Val Thr Val Ser Ser
        115

<210> SEQ ID NO 36
<211> LENGTH: 108
<212> TYPE: PRT
<213> ORGANISM: Artificial Sequence
<220> FEATURE:
<223> OTHER INFORMATION: 13E8; VL

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105

<210> SEQ ID NO 37
<211> LENGTH: 117
<212> TYPE: PRT
<213> ORGANISM: Artificial Sequence
<220> FEATURE:
<223> OTHER INFORMATION: 13E8; VH

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
                100                 105                 110

Val Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: 14C10; VL
```

-continued

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly His Ile Ile Pro
                85                  90                  95

Pro Thr Phe Gly Gln Gly Thr Lys Val Glu Ile Lys
            100                 105

<210> SEQ ID NO 39
<211> LENGTH: 117
<212> TYPE: PRT
<213> ORGANISM: Artificial Sequence
<220> FEATURE:
<223> OTHER INFORMATION: 14C10; VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Trp Met Gly Pro Phe Asp Tyr Trp Gly Gln Gly Thr Leu
            100                 105                 110

Val Thr Val Ser Ser
        115

<210> SEQ ID NO 40
<211> LENGTH: 108
<212> TYPE: PRT
<213> ORGANISM: Artificial Sequence
<220> FEATURE:
<223> OTHER INFORMATION: 17A11; VL

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105

<210> SEQ ID NO 41
<211> LENGTH: 117
<212> TYPE: PRT
<213> ORGANISM: Artificial Sequence
<220> FEATURE:
<223> OTHER INFORMATION: 17A11; VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 42
<211> LENGTH: 108
<212> TYPE: PRT
<213> ORGANISM: Artificial Sequence
<220> FEATURE:
<223> OTHER INFORMATION: 19G1; VL

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 43
<211> LENGTH: 117
<212> TYPE: PRT
<213> ORGANISM: Artificial Sequence

<220> FEATURE:
<223> OTHER INFORMATION: 19G1; VH

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 44
<211> LENGTH: 108
<212> TYPE: PRT
<213> ORGANISM: Artificial Sequence
<220> FEATURE:
<223> OTHER INFORMATION: 20G8; VL

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 45
<211> LENGTH: 117
<212> TYPE: PRT
<213> ORGANISM: Artificial Sequence
<220> FEATURE:
<223> OTHER INFORMATION: 20G8; VH

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Gly Phe Asn Tyr Trp Gly Gln Gly Thr Leu
                100                 105                 110

Val Thr Val Ser Ser
            115

<210> SEQ ID NO 46
<211> LENGTH: 108
<212> TYPE: PRT
<213> ORGANISM: Artificial Sequence
<220> FEATURE:
<223> OTHER INFORMATION: 4B9; VL

<400> SEQUENCE: 46

Glu Ile Val Leu Thr Gln Ser Pro Gly Thr Leu Ser Leu Ser Pro Gly
 1                   5                  10                  15

Glu Arg Ala Thr Leu Ser Cys Arg Ala Ser Gln Ser Val Thr Ser Ser
                 20                  25                  30

Tyr Leu Ala Trp Tyr Gln Gln Lys Pro Gly Gln Ala Pro Arg Leu Leu
             35                  40                  45

Ile Asn Val Gly Ser Arg Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys
                100                 105

<210> SEQ ID NO 47
<211> LENGTH: 117
<212> TYPE: PRT
<213> ORGANISM: Artificial Sequence
<220> FEATURE:
<223> OTHER INFORMATION: 4B9; VH

<400> SEQUENCE: 47

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ile Gly Ser Gly Ala Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Gly Phe Asn Tyr Trp Gly Gln Gly Thr Leu
                100                 105                 110

Val Thr Val Ser Ser
            115

-continued

```
<210> SEQ ID NO 48
<211> LENGTH: 108
<212> TYPE: PRT
<213> ORGANISM: Artificial Sequence
<220> FEATURE:
<223> OTHER INFORMATION: 5B8; VL

<400> SEQUENCE: 48
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

```
<210> SEQ ID NO 49
<211> LENGTH: 117
<212> TYPE: PRT
<213> ORGANISM: Artificial Sequence
<220> FEATURE:
<223> OTHER INFORMATION: 5B8; VH

<400> SEQUENCE: 49
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Trp Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

```
<210> SEQ ID NO 50
<211> LENGTH: 108
<212> TYPE: PRT
<213> ORGANISM: Artificial Sequence
<220> FEATURE:
<223> OTHER INFORMATION: 5F1; VL

<400> SEQUENCE: 50
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
          35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
              85                  90                  95

Pro Thr Phe Gly Gln Gly Thr Lys Val Glu Ile Lys
              100                 105

<210> SEQ ID NO 51
<211> LENGTH: 117
<212> TYPE: PRT
<213> ORGANISM: Artificial Sequence
<220> FEATURE:
<223> OTHER INFORMATION: 5F1; VH

<400> SEQUENCE: 51

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
              20                  25                  30

Ala Met Ser Trp Val Arg Gln Ala Pro Gly Lys Gly Leu Glu Trp Val
          35                  40                  45

Ser Ala Ile Ile Ser Ser Gly Ala Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
              85                  90                  95

Ala Lys Gly Trp Phe Gly Gly Phe Asn Tyr Trp Gly Gln Gly Thr Leu
              100                 105                 110

Val Thr Val Ser Ser
         115

<210> SEQ ID NO 52
<211> LENGTH: 108
<212> TYPE: PRT
<213> ORGANISM: Artificial Sequence
<220> FEATURE:
<223> OTHER INFORMATION: 14B3; VL

<400> SEQUENCE: 52

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Thr Ser Ser
              20                  25                  30

Tyr Leu Ala Trp Tyr Gln Gln Lys Pro Gly Gln Ala Pro Arg Leu Leu
          35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
              85                  90                  95

Pro Thr Phe Gly Gln Gly Thr Lys Val Glu Ile Lys
              100                 105

<210> SEQ ID NO 53
<211> LENGTH: 117
<212> TYPE: PRT
<213> ORGANISM: Artificial Sequence
<220> FEATURE:
<223> OTHER INFORMATION: 14B3; VH

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 54
<211> LENGTH: 108
<212> TYPE: PRT
<213> ORGANISM: Artificial Sequence
<220> FEATURE:
<223> OTHER INFORMATION: 16F1; VL

<400> SEQUENCE: 54

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 55
<211> LENGTH: 117
<212> TYPE: PRT
<213> ORGANISM: Artificial Sequence
<220> FEATURE:
<223> OTHER INFORMATION: 16F1; VH

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Gly Ile Ile Gly Ser Gly Gly Ile Thr Tyr Tyr Ala Asp Ser Val
 50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 56
<211> LENGTH: 108
<212> TYPE: PRT
<213> ORGANISM: Artificial Sequence
<220> FEATURE:
<223> OTHER INFORMATION: 16F8; VL

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 57
<211> LENGTH: 117
<212> TYPE: PRT
<213> ORGANISM: Artificial Sequence
<220> FEATURE:
<223> OTHER INFORMATION: 16F8; VH

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Leu Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 58
<211> LENGTH: 108
<212> TYPE: PRT
<213> ORGANISM: Artificial Sequence
<220> FEATURE:
<223> OTHER INFORMATION: O3C9; VL

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 59
<211> LENGTH: 117
<212> TYPE: PRT
<213> ORGANISM: Artificial Sequence
<220> FEATURE:
<223> OTHER INFORMATION: O3C9; VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ser Pro Gly Lys Gly Leu Glu Trp Val
        35                  40                  45

Ser Ala Ile Ile Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 60
<211> LENGTH: 108
<212> TYPE: PRT
<213> ORGANISM: Artificial Sequence
<220> FEATURE:
<223> OTHER INFORMATION: O2D7; VL -continued

<400> SEQUENCE: 60

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Met Leu Pro
                85                  90                  95

Pro Thr Phe Gly Gln Gly Thr Lys Val Glu Ile Lys
            100                 105

<210> SEQ ID NO 61
<211> LENGTH: 117
<212> TYPE: PRT
<213> ORGANISM: Artificial Sequence
<220> FEATURE:
<223> OTHER INFORMATION: O2D7; VH

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 62
<211> LENGTH: 108
<212> TYPE: PRT
<213> ORGANISM: Artificial Sequence
<220> FEATURE:
<223> OTHER INFORMATION: 28H1; VL

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 63
<211> LENGTH: 116
<212> TYPE: PRT
<213> ORGANISM: Artificial Sequence
<220> FEATURE:
<223> OTHER INFORMATION: 28H1; VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: 22A3; VL

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 65
<211> LENGTH: 117
<212> TYPE: PRT
<213> ORGANISM: Artificial Sequence

```
<220> FEATURE:
<223> OTHER INFORMATION: 22A3; VH

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 66
<211> LENGTH: 108
<212> TYPE: PRT
<213> ORGANISM: Artificial Sequence
<220> FEATURE:
<223> OTHER INFORMATION: 29B11; VL

<400> SEQUENCE: 66

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 67
<211> LENGTH: 117
<212> TYPE: PRT
<213> ORGANISM: Artificial Sequence
<220> FEATURE:
<223> OTHER INFORMATION: 29B11; VH

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
                100                 105                 110

Val Thr Val Ser Ser
            115

<210> SEQ ID NO 68
<211> LENGTH: 108
<212> TYPE: PRT
<213> ORGANISM: Artificial Sequence
<220> FEATURE:
<223> OTHER INFORMATION: 23C10; VL

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
                100                 105

<210> SEQ ID NO 69
<211> LENGTH: 117
<212> TYPE: PRT
<213> ORGANISM: Artificial Sequence
<220> FEATURE:
<223> OTHER INFORMATION: 23C10; VH

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Thr Asn Gly Asn Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
                100                 105                 110

Val Thr Val Ser Ser
            115
```

```
<210> SEQ ID NO 70
<211> LENGTH: 107
<212> TYPE: PRT
<213> ORGANISM: Artificial Sequence
<220> FEATURE:
<223> OTHER INFORMATION: 2B10_C3B6; VL

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 71
<211> LENGTH: 121
<212> TYPE: PRT
<213> ORGANISM: Artificial Sequence
<220> FEATURE:
<223> OTHER INFORMATION: 2B10_C3B6; VH

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: 2B10_6A12; VL

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

Leu Gly Trp Tyr Gln Gln Lys Pro Gly Lys Ala Pro Lys Arg Leu Ile
                35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Asn Gly Leu Gln Pro Ala
                 85                  90                  95

Thr Phe Gly Gln Gly Thr Lys Val Glu Ile Lys
                100                 105

<210> SEQ ID NO 73
<211> LENGTH: 121
<212> TYPE: PRT
<213> ORGANISM: Artificial Sequence
<220> FEATURE:
<223> OTHER INFORMATION: 2B10_6A12; VH

<400> SEQUENCE: 73

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Val Ile Pro Ile Leu Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Tyr Gly Tyr Ala Tyr Tyr Gly Ala Phe Asp Tyr Trp Gly
                100                 105                 110

Gln Gly Thr Thr Val Thr Val Ser Ser
            115                 120

<210> SEQ ID NO 74
<211> LENGTH: 107
<212> TYPE: PRT
<213> ORGANISM: Artificial Sequence
<220> FEATURE:
<223> OTHER INFORMATION: 2B10_C3A6; VL

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Val
                20                  25                  30

Leu Gly Trp Tyr Gln Gln Lys Pro Gly Lys Ala Pro Lys Arg Leu Ile
                35                  40                  45

Tyr Asp Ser Ser Ser Leu Gln Ser Gly Val Pro Ser Arg Phe Ser Gly
 50                  55                  60

Gly Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Asn Gly Leu Gln Pro Ala
                 85                  90                  95

Thr Phe Gly Gln Gly Thr Lys Val Glu Ile Lys
                100                 105

-continued

```
<210> SEQ ID NO 75
<211> LENGTH: 121
<212> TYPE: PRT
<213> ORGANISM: Artificial Sequence
<220> FEATURE:
<223> OTHER INFORMATION: 2B10_C3A6; VH

<400> SEQUENCE: 75
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

```
<210> SEQ ID NO 76
<211> LENGTH: 107
<212> TYPE: PRT
<213> ORGANISM: Artificial Sequence
<220> FEATURE:
<223> OTHER INFORMATION: 2B10_D1A2_wt; VL

<400> SEQUENCE: 76
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

```
<210> SEQ ID NO 77
<211> LENGTH: 121
<212> TYPE: PRT
<213> ORGANISM: Artificial Sequence
<220> FEATURE:
<223> OTHER INFORMATION: 2B10_D1A2_wt; VH

<400> SEQUENCE: 77
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Leu Tyr Gly Tyr Ala Tyr Tyr Gly Ala Phe Asp Tyr Trp Gly
                100                 105                 110

Gln Gly Thr Thr Val Thr Val Ser Ser
            115                 120
```

<210> SEQ ID NO 78
<211> LENGTH: 107
<212> TYPE: PRT
<213> ORGANISM: Artificial Sequence
<220> FEATURE:
<223> OTHER INFORMATION: 2B10_D1A2_VD; VL

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
 50                 55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 79
<211> LENGTH: 121
<212> TYPE: PRT
<213> ORGANISM: Artificial Sequence
<220> FEATURE:
<223> OTHER INFORMATION: 2B10_D1A2_VD; VH

<400> SEQUENCE: 79

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
 50                 55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 80
<211> LENGTH: 107
<212> TYPE: PRT
<213> ORGANISM: Artificial Sequence
<220> FEATURE:
<223> OTHER INFORMATION: 2B10_O7D8; VL

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 81
<211> LENGTH: 121
<212> TYPE: PRT
<213> ORGANISM: Artificial Sequence
<220> FEATURE:
<223> OTHER INFORMATION: 2B10_O7D8; VH

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 82
<211> LENGTH: 107
<212> TYPE: PRT
<213> ORGANISM: Artificial Sequence
<220> FEATURE:
<223> OTHER INFORMATION: 2B10_O1F7; VL -continued

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
50                  55                  60

Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 83
<211> LENGTH: 121
<212> TYPE: PRT
<213> ORGANISM: Artificial Sequence
<220> FEATURE:
<223> OTHER INFORMATION: 2B10_O1F7; VH

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 84
<211> LENGTH: 107
<212> TYPE: PRT
<213> ORGANISM: Artificial Sequence
<220> FEATURE:
<223> OTHER INFORMATION: 2B10_6H10; VL

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Gln Ala Ala Thr Ser Leu Gln Ser Gly Val Pro Ser Arg Phe Ser Gly
50                  55                  60

```
Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 85
<211> LENGTH: 121
<212> TYPE: PRT
<213> ORGANISM: Artificial Sequence
<220> FEATURE:
<223> OTHER INFORMATION: 2B10_6H10; VH

<400> SEQUENCE: 85

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 86
<211> LENGTH: 112
<212> TYPE: PRT
<213> ORGANISM: Artificial Sequence
<220> FEATURE:
<223> OTHER INFORMATION: LC007 VH

<400> SEQUENCE: 86

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110
```

<210> SEQ ID NO 87
<211> LENGTH: 107
<212> TYPE: PRT
<213> ORGANISM: Artificial Sequence

```
<220> FEATURE:
<223> OTHER INFORMATION: LC007 VL

<400> SEQUENCE: 87

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 88
<211> LENGTH: 6
<212> TYPE: PRT
<213> ORGANISM: Artificial Sequence
<220> FEATURE:
<223> OTHER INFORMATION: anti-CD20 HCDR1

<400> SEQUENCE: 88

Gly Tyr Ala Phe Ser Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: anti-CD20 HCDR2

<400> SEQUENCE: 89

Phe Pro Gly Asp Gly Asp Thr Asp
1               5

<210> SEQ ID NO 90
<211> LENGTH: 10
<212> TYPE: PRT
<213> ORGANISM: Artificial Sequence
<220> FEATURE:
<223> OTHER INFORMATION: anti-CD20 HCDR3

<400> SEQUENCE: 90

Asn Val Phe Asp Gly Tyr Trp Leu Val Tyr
1               5                   10

<210> SEQ ID NO 91
<211> LENGTH: 16
<212> TYPE: PRT
<213> ORGANISM: Artificial Sequence
<220> FEATURE:
<223> OTHER INFORMATION: anti-CD20 LCDR1

<400> SEQUENCE: 91

Arg Ser Ser Lys Ser Leu Leu His Ser Asn Gly Ile Thr Tyr Leu Tyr
1               5                   10                  15
```

-continued

```
<210> SEQ ID NO 92
<211> LENGTH: 7
<212> TYPE: PRT
<213> ORGANISM: Artificial Sequence
<220> FEATURE:
<223> OTHER INFORMATION: anti-CD20 LCDR2

<400> SEQUENCE: 92

Gln Met Ser Asn Leu Val Ser
1               5

<210> SEQ ID NO 93
<211> LENGTH: 9
<212> TYPE: PRT
<213> ORGANISM: Artificial Sequence
<220> FEATURE:
<223> OTHER INFORMATION: anti-CD20 LCDR3

<400> SEQUENCE: 93

Ala Gln Asn Leu Glu Leu Pro Tyr Thr
1               5

<210> SEQ ID NO 94
<211> LENGTH: 119
<212> TYPE: PRT
<213> ORGANISM: Artificial Sequence
<220> FEATURE:
<223> OTHER INFORMATION: anti-CD20 VH

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 95
<211> LENGTH: 115
<212> TYPE: PRT
<213> ORGANISM: Artificial Sequence
<220> FEATURE:
<223> OTHER INFORMATION: anti-CD20 VL

<400> SEQUENCE: 95

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45
```

```
Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Arg Thr Val
       115

<210> SEQ ID NO 96
<211> LENGTH: 5
<212> TYPE: PRT
<213> ORGANISM: Artificial Sequence
<220> FEATURE:
<223> OTHER INFORMATION: anti-EGFR HCDR1

<400> SEQUENCE: 96

Asp Tyr Lys Ile His
1               5

<210> SEQ ID NO 97
<211> LENGTH: 17
<212> TYPE: PRT
<213> ORGANISM: Artificial Sequence
<220> FEATURE:
<223> OTHER INFORMATION: anti-EGFR HCDR2

<400> SEQUENCE: 97

Tyr Phe Asn Pro Asn Ser Gly Tyr Ser Thr Tyr Ala Gln Lys Phe Gln
1               5                   10                  15

Gly

<210> SEQ ID NO 98
<211> LENGTH: 11
<212> TYPE: PRT
<213> ORGANISM: Artificial Sequence
<220> FEATURE:
<223> OTHER INFORMATION: anti-EGFR HCDR3

<400> SEQUENCE: 98

Leu Ser Pro Gly Gly Tyr Tyr Val Met Asp Ala
1               5                   10

<210> SEQ ID NO 99
<211> LENGTH: 11
<212> TYPE: PRT
<213> ORGANISM: Artificial Sequence
<220> FEATURE:
<223> OTHER INFORMATION: anti-EGFR LCDR1

<400> SEQUENCE: 99

Arg Ala Ser Gln Gly Ile Asn Asn Tyr Leu Asn
1               5                   10

<210> SEQ ID NO 100
<211> LENGTH: 7
<212> TYPE: PRT
<213> ORGANISM: Artificial Sequence
<220> FEATURE:
<223> OTHER INFORMATION: anti-EGFR LCDR2
```

<400> SEQUENCE: 100

Asn Thr Asn Asn Leu Gln Thr
1               5

<210> SEQ ID NO 101
<211> LENGTH: 8
<212> TYPE: PRT
<213> ORGANISM: Artificial Sequence
<220> FEATURE:
<223> OTHER INFORMATION: anti-EGFR LCDR3

<400> SEQUENCE: 101

Leu Gln His Asn Ser Phe Pro Thr
1               5

<210> SEQ ID NO 102
<211> LENGTH: 120
<212> TYPE: PRT
<213> ORGANISM: Artificial Sequence
<220> FEATURE:
<223> OTHER INFORMATION: anti-EGFR VH

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 103
<211> LENGTH: 108
<212> TYPE: PRT
<213> ORGANISM: Artificial Sequence
<220> FEATURE:
<223> OTHER INFORMATION: anti-EGFR VL

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

-continued

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105

<210> SEQ ID NO 104
<211> LENGTH: 118
<212> TYPE: PRT
<213> ORGANISM: Artificial Sequence
<220> FEATURE:
<223> OTHER INFORMATION: anti-IGF-1R VH (1)

<400> SEQUENCE: 104

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 105
<211> LENGTH: 108
<212> TYPE: PRT
<213> ORGANISM: Artificial Sequence
<220> FEATURE:
<223> OTHER INFORMATION: anti-IGF-1R VL (1)

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 106
<211> LENGTH: 118
<212> TYPE: PRT
<213> ORGANISM: Artificial Sequence
<220> FEATURE:
<223> OTHER INFORMATION: anti-IGF-1R VH (2)

<400> SEQUENCE: 106

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Met
            35                  40                  45

Ala Ile Ile Trp Phe Asp Gly Ser Ser Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser
            115

<210> SEQ ID NO 107
<211> LENGTH: 108
<212> TYPE: PRT
<213> ORGANISM: Artificial Sequence
<220> FEATURE:
<223> OTHER INFORMATION: anti-IGF-1R VL (2)

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys
            100                 105

<210> SEQ ID NO 108
<211> LENGTH: 5
<212> TYPE: PRT
<213> ORGANISM: Artificial Sequence
<220> FEATURE:
<223> OTHER INFORMATION: anti-CEA HCDR1

<400> SEQUENCE: 108

Glu Phe Gly Met Asn
1               5

<210> SEQ ID NO 109
<211> LENGTH: 17
<212> TYPE: PRT
<213> ORGANISM: Artificial Sequence
<220> FEATURE:
<223> OTHER INFORMATION: anti-CEA HCDR2

<400> SEQUENCE: 109

Trp Ile Asn Thr Lys Thr Gly Glu Ala Thr Tyr Val Glu Glu Phe Lys
1               5                   10                  15
Gly

<210> SEQ ID NO 110
<211> LENGTH: 12
<212> TYPE: PRT
<213> ORGANISM: Artificial Sequence
<220> FEATURE:
<223> OTHER INFORMATION: anti-CEA HCDR3

<400> SEQUENCE: 110

Trp Asp Phe Ala Tyr Tyr Val Glu Ala Met Asp Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: anti-CEA LCDR1

<400> SEQUENCE: 111

Lys Ala Ser Ala Ala Val Gly Thr Tyr Val Ala
1               5                   10

<210> SEQ ID NO 112
<211> LENGTH: 7
<212> TYPE: PRT
<213> ORGANISM: Artificial Sequence
<220> FEATURE:
<223> OTHER INFORMATION: anti-CEA LCDR2

<400> SEQUENCE: 112

Ser Ala Ser Tyr Arg Lys Arg
1               5

<210> SEQ ID NO 113
<211> LENGTH: 10
<212> TYPE: PRT
<213> ORGANISM: Artificial Sequence
<220> FEATURE:
<223> OTHER INFORMATION: anti-CEA LCDR3

<400> SEQUENCE: 113

His Gln Tyr Tyr Thr Tyr Pro Leu Phe Thr
1               5                   10

<210> SEQ ID NO 114
<211> LENGTH: 121
<212> TYPE: PRT
<213> ORGANISM: Artificial Sequence
<220> FEATURE:
<223> OTHER INFORMATION: anti-CEA VH

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

```
Gly Trp Ile Asn Thr Lys Thr Gly Glu Ala Thr Tyr Val Glu Glu Phe
 50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ser
            115                 120
```

<210> SEQ ID NO 115
<211> LENGTH: 108
<212> TYPE: PRT
<213> ORGANISM: Artificial Sequence
<220> FEATURE:
<223> OTHER INFORMATION: anti-CEA VL

<400> SEQUENCE: 115

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Ala Ala Val Gly Thr Tyr
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Lys Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys
                100                 105
```

<210> SEQ ID NO 116
<211> LENGTH: 11
<212> TYPE: PRT
<213> ORGANISM: Artificial Sequence
<220> FEATURE:
<223> OTHER INFORMATION: anti-MCSP HCDR1

<400> SEQUENCE: 116

```
Gly Gly Ser Ile Thr Ser Gly Tyr Tyr Trp Asn
 1               5                  10
```

<210> SEQ ID NO 117
<211> LENGTH: 16
<212> TYPE: PRT
<213> ORGANISM: Artificial Sequence
<220> FEATURE:
<223> OTHER INFORMATION: anti-MCSP HCDR2

<400> SEQUENCE: 117

```
Tyr Ile Thr Tyr Asp Gly Ser Asn Asn Tyr Asn Pro Ser Leu Lys Ser
 1               5                  10                  15
```

<210> SEQ ID NO 118
<211> LENGTH: 3
<212> TYPE: PRT
<213> ORGANISM: Artificial Sequence
<220> FEATURE:
<223> OTHER INFORMATION: anti-MCSP HCDR3

```
<400> SEQUENCE: 118

Phe Asp Tyr
1

<210> SEQ ID NO 119
<211> LENGTH: 11
<212> TYPE: PRT
<213> ORGANISM: Artificial Sequence
<220> FEATURE:
<223> OTHER INFORMATION: anti-MCSP LCDR1

<400> SEQUENCE: 119

Arg Ala Ser Gln Gly Ile Arg Asn Tyr Leu Asn
1               5                   10

<210> SEQ ID NO 120
<211> LENGTH: 7
<212> TYPE: PRT
<213> ORGANISM: Artificial Sequence
<220> FEATURE:
<223> OTHER INFORMATION: anti-MCSP LCDR2

<400> SEQUENCE: 120

Tyr Thr Ser Ser Leu His Ser
1               5

<210> SEQ ID NO 121
<211> LENGTH: 9
<212> TYPE: PRT
<213> ORGANISM: Artificial Sequence
<220> FEATURE:
<223> OTHER INFORMATION: anti-MCSP LCDR3

<400> SEQUENCE: 121

Gln Gln Tyr Ser Lys Leu Pro Trp Thr
1               5

<210> SEQ ID NO 122
<211> LENGTH: 112
<212> TYPE: PRT
<213> ORGANISM: Artificial Sequence
<220> FEATURE:
<223> OTHER INFORMATION: anti-MCSP VH

<400> SEQUENCE: 122

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110
```

<210> SEQ ID NO 123
<211> LENGTH: 107
<212> TYPE: PRT
<213> ORGANISM: Artificial Sequence
<220> FEATURE:
<223> OTHER INFORMATION: anti-MCSP VL

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
            100                 105
```

<210> SEQ ID NO 124
<211> LENGTH: 328
<212> TYPE: PRT
<213> ORGANISM: Homo sapiens

<400> SEQUENCE: 124

```
Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Ala
                85                  90                  95

Glu Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220
```

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
            245                 250                 255

Asp Ile Ala Val Glu Trp Glu Ser Asn Gly Gln Pro Glu Asn Asn Tyr
        260                 265                 270

Lys Thr Thr Pro Pro Val Leu Asp Ser Asp Gly Ser Phe Phe Leu Tyr
    275                 280                 285

Ser Lys Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305             310                 315                 320

Ser Leu Ser Leu Ser Pro Gly Lys
                325

<210> SEQ ID NO 125
<211> LENGTH: 446
<212> TYPE: PRT
<213> ORGANISM: Artificial Sequence
<220> FEATURE:
<223> OTHER INFORMATION: 28H1 Fab HC-Fc hole (LALA P329G)

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

```
Glu Val Thr Cys Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 126
<211> LENGTH: 593
<212> TYPE: PRT
<213> ORGANISM: Artificial Sequence
<220> FEATURE:
<223> OTHER INFORMATION: 28H1 Fab HC-Fc knob (LALA P329G)-IL-2 qm

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Ser Gly Gly Gly Ser Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
                565                 570                 575

Phe Leu Asn Arg Trp Ile Thr Phe Ala Gln Ser Ile Ile Ser Thr Leu
            580                 585                 590

Thr
```

```
<210> SEQ ID NO 127
<211> LENGTH: 447
<212> TYPE: PRT
<213> ORGANISM: Artificial Sequence
<220> FEATURE:
<223> OTHER INFORMATION: 4G8 Fab HC-Fc hole (LALA P329G)

<400> SEQUENCE: 127
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Ser | Gly | Gly | Ser | Thr | Tyr | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Gly | Trp | Leu | Gly | Asn | Phe | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Lys | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Ala | Ala | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Gly | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Cys | Thr | Leu | Pro |
| | | | 340 | | | | | 345 | | | | | 350 | | |
| Pro | Ser | Arg | Asp | Glu | Leu | Thr | Lys | Asn | Gln | Val | Ser | Leu | Ser | Cys | Ala |
| | | 355 | | | | | 360 | | | | | 365 | | | |

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 128
<211> LENGTH: 594
<212> TYPE: PRT
<213> ORGANISM: Artificial Sequence
<220> FEATURE:
<223> OTHER INFORMATION: 4G8 Fab HC-Fc knob (LALA P329G)-IL-2 qm

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Gly Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Cys Arg Asp Glu Leu Thr Lys Asn Gln Val Ser Leu Trp Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Ser Gly Gly Gly Ser Ala Pro Ala
450                 455                 460
Ser Ser Ser Thr Lys Lys Thr Gln Leu Gln Leu Glu His Leu Leu Leu
465                 470                 475                 480
Asp Leu Gln Met Ile Leu Asn Gly Ile Asn Asn Tyr Lys Asn Pro Lys
                485                 490                 495
Leu Thr Arg Met Leu Thr Ala Lys Phe Ala Met Pro Lys Lys Ala Thr
            500                 505                 510
Glu Leu Lys His Leu Gln Cys Leu Glu Glu Leu Lys Pro Leu Glu
        515                 520                 525
Glu Val Leu Asn Gly Ala Gln Ser Lys Asn Phe His Leu Arg Pro Arg
530                 535                 540
Asp Leu Ile Ser Asn Ile Asn Val Ile Val Leu Glu Leu Lys Gly Ser
545                 550                 555                 560
Glu Thr Thr Phe Met Cys Glu Tyr Ala Asp Glu Thr Ala Thr Ile Val
                565                 570                 575
Glu Phe Leu Asn Arg Trp Ile Thr Phe Ala Gln Ser Ile Ile Ser Thr
            580                 585                 590
Leu Thr
```

<210> SEQ ID NO 129
<211> LENGTH: 215
<212> TYPE: PRT
<213> ORGANISM: Artificial Sequence
<220> FEATURE:
<223> OTHER INFORMATION: 4G8 Fab LC

<400> SEQUENCE: 129

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Arg Ser
            20                  25                  30
Tyr Leu Ala Trp Tyr Gln Gln Lys Pro Gly Gln Ala Pro Arg Leu Leu
        35                  40                  45
```

```
Ile Ile Gly Ala Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 130
<211> LENGTH: 447
<212> TYPE: PRT
<213> ORGANISM: Artificial Sequence
<220> FEATURE:
<223> OTHER INFORMATION: 4B9 Fab HC-Fc hole (LALA P329G)

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
    435                 440                 445

<210> SEQ ID NO 131
<211> LENGTH: 594
<212> TYPE: PRT
<213> ORGANISM: Artificial Sequence
<220> FEATURE:
<223> OTHER INFORMATION: 4B9 Fab HC-Fc knob (LALA P329G)-IL-2 qm

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Ala Pro Ala
            450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Ala Lys Phe Ala Met Pro Lys Lys Ala Thr
            500                 505                 510

Glu Leu Lys His Leu Gln Cys Leu Glu Glu Glu Leu Lys Pro Leu Glu
            515                 520                 525
```

```
Glu Val Leu Asn Gly Ala Gln Ser Lys Asn Phe His Leu Arg Pro Arg
            530                 535                 540

Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
            580                 585                 590

Leu Thr

<210> SEQ ID NO 132
<211> LENGTH: 215
<212> TYPE: PRT
<213> ORGANISM: Artificial Sequence
<220> FEATURE:
<223> OTHER INFORMATION: 3F2 Fab LC

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 133
<211> LENGTH: 445
<212> TYPE: PRT
<213> ORGANISM: Artificial Sequence
<220> FEATURE:
<223> OTHER INFORMATION: DP47 GS Fab HC-Fc hole (LALA P329G)
```

<400> SEQUENCE: 133

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415
```

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 134
<211> LENGTH: 592
<212> TYPE: PRT
<213> ORGANISM: Artificial Sequence
<220> FEATURE:
<223> OTHER INFORMATION: DP47GS Fab HC-Fc knob (LALA P329G)-IL-2 qm

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

```
Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Ala Lys Phe Ala Met Pro Lys Lys Ala Thr Glu Leu
            500                 505                 510

Lys His Leu Gln Cys Leu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590

<210> SEQ ID NO 135
<211> LENGTH: 215
<212> TYPE: PRT
<213> ORGANISM: Artificial Sequence
<220> FEATURE:
<223> OTHER INFORMATION: DP47GS Fab LC

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110
```

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 136
<211> LENGTH: 451
<212> TYPE: PRT
<213> ORGANISM: Artificial Sequence
<220> FEATURE:
<223> OTHER INFORMATION: CH1A1A Fab HC-Fc hole (LALA P329G)

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

```
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
        355                 360                 365
Leu Ser Cys Ala Val Lys Gly Phe Tyr Pro Ser Asp Ile Ala Val Glu
    370                 375                 380
Trp Glu Ser Asn Gly Gln Pro Glu Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 137
<211> LENGTH: 598
<212> TYPE: PRT
<213> ORGANISM: Artificial Sequence
<220> FEATURE:
<223> OTHER INFORMATION: CH1A1A Fab HC-Fc knob (LALA P329G)-IL-2 qm

<400> SEQUENCE: 137

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
        35                  40                  45
Gly Trp Ile Asn Thr Lys Thr Gly Glu Ala Thr Tyr Val Glu Glu Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Cys Arg Asp Glu Leu Thr Lys Asn Gln Val Ser
        355                 360                 365
Leu Trp Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Gly Gly Gly Ser Gly Gly Gly Ser Gly Gly Gly Gly
    450                 455                 460
Ser Ala Pro Ala Ser Ser Ser Thr Lys Lys Thr Gln Leu Gln Leu Glu
465                 470                 475                 480
His Leu Leu Leu Asp Leu Gln Met Ile Leu Asn Gly Ile Asn Asn Tyr
                485                 490                 495
Lys Asn Pro Lys Leu Thr Arg Met Leu Thr Ala Lys Phe Ala Met Pro
            500                 505                 510
Lys Lys Ala Thr Glu Leu Lys His Leu Gln Cys Leu Glu Glu Glu Leu
        515                 520                 525
Lys Pro Leu Glu Glu Val Leu Asn Gly Ala Gln Ser Lys Asn Phe His
    530                 535                 540
Leu Arg Pro Arg Asp Leu Ile Ser Asn Ile Asn Val Ile Val Leu Glu
545                 550                 555                 560
Leu Lys Gly Ser Glu Thr Thr Phe Met Cys Glu Tyr Ala Asp Glu Thr
                565                 570                 575
```

```
Ala Thr Ile Val Glu Phe Leu Asn Arg Trp Ile Thr Phe Ala Gln Ser
            580                 585                 590

Ile Ile Ser Thr Leu Thr
            595

<210> SEQ ID NO 138
<211> LENGTH: 215
<212> TYPE: PRT
<213> ORGANISM: Artificial Sequence
<220> FEATURE:
<223> OTHER INFORMATION: CH1A1A Fab LC

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Val Gly Thr Tyr
            20                  25                  30

Val Ala Trp Tyr Gln Gln Lys Pro Gly Lys Ala Pro Lys Leu Leu Ile
            35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 139
<211> LENGTH: 10
<212> TYPE: PRT
<213> ORGANISM: Artificial Sequence
<220> FEATURE:
<223> OTHER INFORMATION: anti-Her3 HCDR1

<400> SEQUENCE: 139

Gly Tyr Thr Phe Arg Ser Ser Tyr Ile Ser
1               5                   10

<210> SEQ ID NO 140
<211> LENGTH: 17
<212> TYPE: PRT
<213> ORGANISM: Artificial Sequence
<220> FEATURE:
<223> OTHER INFORMATION: anti-Her3 HCDR2
```

<400> SEQUENCE: 140

Trp Ile Tyr Ala Gly Thr Gly Ser Pro Ser Tyr Asn Gln Lys Leu Gln
1               5                   10                  15

Gly

<210> SEQ ID NO 141
<211> LENGTH: 11
<212> TYPE: PRT
<213> ORGANISM: Artificial Sequence
<220> FEATURE:
<223> OTHER INFORMATION: anti-Her3 HCDR3

<400> SEQUENCE: 141

His Arg Asp Tyr Tyr Ser Asn Ser Leu Thr Tyr
1               5                   10

<210> SEQ ID NO 142
<211> LENGTH: 120
<212> TYPE: PRT
<213> ORGANISM: Artificial Sequence
<220> FEATURE:
<223> OTHER INFORMATION: anti-Her3 VH

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser
        115                 120

<210> SEQ ID NO 143
<211> LENGTH: 16
<212> TYPE: PRT
<213> ORGANISM: Artificial Sequence
<220> FEATURE:
<223> OTHER INFORMATION: anti-Her3 LCDR1

<400> SEQUENCE: 143

Lys Ser Ser Gln Ser Val Leu Asn Ser Gly Asn Gln Lys Asn Tyr Leu
1               5                   10                  15

<210> SEQ ID NO 144
<211> LENGTH: 7
<212> TYPE: PRT
<213> ORGANISM: Artificial Sequence
<220> FEATURE:
<223> OTHER INFORMATION: anti-Her3 LCDR2

<400> SEQUENCE: 144

Trp Ala Ser Thr Arg Glu Ser
1               5

```
<210> SEQ ID NO 145
<211> LENGTH: 9
<212> TYPE: PRT
<213> ORGANISM: Artificial Sequence
<220> FEATURE:
<223> OTHER INFORMATION: anti-Her3 LCDR3

<400> SEQUENCE: 145

Gln Ser Asp Tyr Ser Tyr Pro Tyr Thr
1               5

<210> SEQ ID NO 146
<211> LENGTH: 113
<212> TYPE: PRT
<213> ORGANISM: Artificial Sequence
<220> FEATURE:
<223> OTHER INFORMATION: anti-Her3 VL

<400> SEQUENCE: 146

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys
```

COMBINATION IL-2 IMMUNOCONJUGATE THERAPY

CROSS-REFERENCE TO RELATED APPLICATIONS

This application is a continuation of U.S. Pat. No. 9,526, 797, issued Dec. 27, 2016, which claims benefit under 35 U.S.C. § 119 to European Patent Application No. 12179473.9 filed on Aug. 7, 2012. The entire contents of each of the foregoing applications are hereby incorporated by reference in their entirety.

SEQUENCE LISTING

The instant application contains a Sequence Listing submitted via EFS-Web and hereby incorporated by reference in its entirety. Said ASCII copy, created on Aug. 7, 2013, is named P4996US_sequence_listing.txt, and is 170,705 bytes in size.

FIELD OF THE INVENTION

The present invention generally relates to immunotherapy. More particularly, the invention concerns antigen-targeted immunoconjugates and Fc-engineered antibodies for combined use as immunotherapeutic agents. In addition, the invention relates to pharmaceutical compositions comprising combinations of said immunoconjugates and antibodies and methods of using the same in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. Effector cells can be activated by various stimuli, including a number of cytokines that induce signaling events through binding to their receptors on the surface of immune cells. For example interleukin-2 (IL-2), which, inter alia, stimulates proliferation and activation of cytotoxic T cells and NK cells, has been approved for the treatment of metastatic renal cell carcinoma and malignant melanoma. However, rapid blood clearance and lack of tumor specificity require systemic administration of high doses of a cytokine in order to achieve a sufficiently high concentration of the cytokine at the tumor site to activate an immune response or have an anti-tumor effect. These high systemic levels of cytokine can lead to severe toxicity and adverse reactions, as is the case also for IL-2. For use in cancer therapy, it is therefore desirable to specifically deliver cytokines to the tumor or tumor microenvironment. This can be achieved by conjugating the cytokine to a targeting moiety, e.g. an antibody or an antibody fragment, specific for a tumor antigen. A further advantage of such immunoconjugates is their increased serum half-life compared to the unconjugated cytokine. Their ability to maximize immunostimulatory activities at the site of a tumor whilst keeping systemic side effects to a minimum at a lower dose makes cytokine immunoconjugates optimal immunotherapeutic agents.

Another way of activating effector cells is through the engagement of activating Fc receptors on their surface by the Fc portion of immunoglobulins or recombinant fusion proteins comprising an Fc region. The so-called effector functions of an antibody which are mediated by its Fc region are an important mechanism of action in antibody-based cancer immunotherapy. Antibody-dependent cell-mediated cytotoxicity, the destruction of antibody-coated target cells (e.g. tumor cells) by NK cells, is triggered when antibody bound to the surface of a cell interacts with Fc receptors on the NK cell. NK cells express FcγRIIIa (CD16a) which recognizes immunoglobulins of the $IgG_1$ or $IgG_3$ subclass. Further effector functions include antibody-dependent cell-mediated phagocytosis (ADCP) and complement dependent cytotoxicity (CDC), and vary with the class and subclass of the antibody since different immune cell types bear different sets of Fc receptors which recognize different types and subtypes of immunoglobulin heavy chain constant domains (e.g. α, δ, γ, ε, or μ heavy chain constant domains, corresponding to IgA, IgD, IgE, IgG, or IgM class antibodies, respectively). Various strategies have been employed to increase the effector functions of antibodies. For example, Shields et al. (J Biol Chem 9(2), 6591-6604 (2001)) show that amino acid substitutions at positions 298, 333, and/or 334 of the Fc region (EU numbering of residues) improve the binding of antibodies to FcγIIIa receptor and ADCC. Further antibody variants having amino acid modifications in the Fc region and exhibiting improved Fc receptor binding and effector function are described e.g. in U.S. Pat. No. 6,737,056, WO 2004/063351 and WO 2004/099249. Alternatively, increased Fc receptor binding and effector function can be obtained by altering the glycosylation of an antibody. IgG1 type antibodies, the most commonly used antibodies in cancer immunotherapy, have a conserved N-linked glycosylation site at Asn 297 in each CH2 domain of the Fc region. The two complex biantennary oligosaccharides attached to Asn 297 are buried between the CH2 domains, forming extensive contacts with the polypeptide backbone, and their presence is essential for the antibody to mediate effector functions including antibody-dependent cell-mediated cytotoxicity (ADCC) (Lifely et al., Glycobiology 5, 813-822 (1995); Jefferis et al., Immunol Rev 163, 59-76 (1998); Wright and Morrison, Trends Biotechnol 15, 26-32 (1997)). Protein engineering studies have shown that FcγRs interact with the lower hinge region of the IgG CH2 domain (Lund et al., J Immunol 157, 4963-69 (1996)). However, FcγR binding also requires the presence of the oligosaccharides in the CH2 region (Lund et al., J Immunol 157, 4963-69 (1996); Wright and Morrison, Trends Biotech 15, 26-31 (1997)), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction between $IgG_1$ and FcγR, and to increase ADCC activity of $IgG_1$ antibodies. Umaña et al. (Nat Biotechnol 17, 176-180 (1999) and U.S. Pat. No. 6,602,684 (WO 99/54342), the contents of which are hereby incorporated by reference in their entirety) showed that overexpression of β(1,4)-N-acetylglucosaminyltransferase III (GnTIII), a glycosyltransferase catalyzing the formation of bisected oligosaccharides, in Chinese hamster ovary (CHO) cells significantly increases the in vitro ADCC activity of antibodies produced in those cells. Overexpression of GnTIII in production cell lines leads to antibodies enriched in bisected oligosaccharides, which are generally also non-fucosylated and of the hybrid type. If in addition to GnTIII, mannosidase II (ManII) is overexpressed in production cell lines, antibodies enriched in bisected, non-fucosylated oligosaccharides of the complex type are obtained (Ferrara et al., Biotechn Bioeng 93, 851-861 (2006)). Both types of antibodies show strongly increased ADCC, as compared to antibodies with unmodified glycans, but only antibodies in which the majority of the N-glycans are of the complex type are able to induce significant complement-dependent cytotoxicity (Ferrara et al., Biotechn Bioeng 93, 851-861 (2006)). The critical factor for the increase of ADCC activity appears to be the elimination of fucose from the innermost N-acetylglucosamine residue of the oligosaccharide core, which improves binding of the IgG Fc domain to FcγRIIIa (Shinkawa et al., J Biol Chem 278, 3466-3473 (2003)). Further methods for producing antibodies with reduced fucosylation include, e.g. expression in α(1,6)-fucosyltransferase deficient host cells (Yamane-Ohnuki et al., Biotech Bioeng 87, 614-622 (2004); Niwa et al., J Immunol Methods 306, 151-160 (2006)).

Despite the successes achieved in anti-cancer immunotherapy by the use of free cytokines, immunoconjugates or engineered antibodies, there is a continuous need for novel efficacious and safe treatment options in cancer therapy.

SUMMARY OF THE INVENTION

The present inventors have found that the combination of these two strategies for local immune cell activation, i.e. simultaneous stimulation of effector cells by cytokine immunoconjugates and by antibodies engineered to have increased effector functions, greatly improves the efficacy of anti-cancer immunotherapy.

Accordingly, the present invention provides a combination of (a) an immunoconjugate comprising a first antibody engineered to have reduced effector function and an effector moiety, and (b) a second antibody engineered to have increased effector function, for use in treating a disease in an individual in need thereof. In one embodiment the effector moiety is a cytokine. In one embodiment the cytokine is selected from the group consisting of IL-2, GM-CSF, IFN-α, and IL-12. In a particular embodiment the effector moiety is IL-2. In another embodiment the effector moiety is IL-12. In another particular embodiment the IL-2 effector moiety is a mutant IL-2 effector moiety comprising at least one amino acid mutation, particularly an amino acid substitution, that reduces or abolishes the affinity of the mutant IL-2 effector moiety to the α-subunit of the IL-2 receptor but preserves the affinity of the mutant IL-2 effector moiety to the intermediate-affinity IL-2 receptor, compared to the non-mutated IL-2 effector moiety. In a specific embodiment, the mutant IL-2 effector moiety comprises one, two or three amino acid substitutions at one, two or three position(s) selected from the positions corresponding to residue 42, 45, and 72 of human IL-2 (SEQ ID NO: 1). In a more specific embodiment, the mutant IL-2 effector moiety comprises three amino acid substitutions at the positions corresponding to residue 42, 45 and 72 of human IL-2. In an even more specific embodiment, the mutant IL-2 effector moiety is human IL-2 comprising the amino acid substitutions F42A, Y45A and L72G. In certain embodiments the mutant IL-2 effector moiety additionally comprises an amino acid mutation at a position corresponding to position 3 of human IL-2, which eliminates the O-glycosylation site of IL-2. In a specific embodiment the mutant IL-2 effector moiety comprises the amino acid sequence of SEQ ID NO: 2. In one embodiment the effector moiety is a single-chain effector moiety.

In one embodiment the first antibody is a full-length IgG class antibody, particularly a full-length IgG$_1$ sub-class antibody. In one embodiment the effector moiety shares an amino- or carboxy-terminal peptide bond with the first antibody. In one embodiment the effector moiety shares an amino-terminal peptide bond with the first antibody. In one embodiment, the effector moiety is fused at its N-terminus to the C-terminus of one of the heavy chains of the first antibody. In a particular embodiment, the immunoconjugate comprises not more than one effector moiety. In one embodiment the immunoconjugate essentially consists of an effector moiety and a first antibody joined by one or more peptide linkers. In a specific embodiment the immunoconjugate comprises an effector moiety, particularly a single chain effector moiety, and a first antibody, particularly a full-length IgG class antibody, wherein the effector moiety is fused at its amino-terminal amino acid to the carboxy-terminus of one of the heavy chains of the first antibody, optionally through a peptide linker. In certain embodiments the first antibody comprises in the Fc region a modification promoting heterodimerization of two non-identical immunoglobulin heavy chains. In a specific embodiment said modification is a knob-into-hole modification, comprising a knob modification in one of the immunoglobulin heavy chains and a hole modification in the other one of the two immunoglobulin heavy chains. In one embodiment, the first antibody comprises a modification within the interface between the two immunoglobulin heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the first antibody comprises the amino acid substitution T366W and optionally the amino acid substitution S354C in one of the immunoglobulin heavy chains, and the amino acid substitutions T366S, L368A, Y407V and optionally Y349C in the other one of the immunoglobulin heavy chains. In a particular embodiment the effector moiety is fused to the amino- or carboxy-terminal amino acid of the immunoglobulin heavy chain comprising the knob modification.

In one embodiment the reduced effector function of the first antibody is selected from the group of reduced binding to an activating Fc receptor, reduced ADCC, reduced ADCP, reduced CDC, and reduced cytokine secretion. In one embodiment the reduced effector function is reduced binding to an activating Fc receptor. In one embodiment the activating Fc receptor is a human receptor. In one embodiment the activating Fc receptor is an Fcγ receptor. In a specific embodiment the activating Fc receptor is selected from the group of FcγRIIIa, FcγRI, and FcRγIIa. In one embodiment the activating Fc receptor is FcγRIIIa, particularly human FcγRIIIa. In one embodiment the reduced effector function is reduced ADCC. In one embodiment the reduced effector function is reduced binding to an activating Fc receptor and reduced ADCC.

In one embodiment the first antibody is engineered by introduction of one or more amino acid mutations in the Fc region. In a specific embodiment the amino acid mutations are amino acid substitutions. In a specific embodiment, the first antibody, particularly a human full-length $IgG_1$ subclass antibody, comprises an amino acid substitution at position P329 of the immunoglobulin heavy chains (Kabat numbering). In a more specific embodiment the amino acid substitution is P329A or P329G, particularly P329G. In one embodiment the antibody comprises a further amino acid substitution at a position selected from S228, E233, L234, L235, N297 and P331 of the immunoglobulin heavy chains. In a more specific embodiment the further amino acid substitution is S228P, E233P, L234A, L235A, L235E, N297A, N297D or P331S. In a particular embodiment the antibody comprises amino acid substitutions at positions P329, L234 and L235 of the immunoglobulin heavy chains (Kabat numbering). In a more particular embodiment the antibody comprises the amino acid substitutions L234A, L235A and P329G (LALA P329G) in the immunoglobulin heavy chains.

In certain embodiments the first antibody is directed to an antigen presented on a tumor cell or in a tumor cell environment. In a specific embodiment the first antibody is directed to an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and Melanoma-associated Chondroitin Sulfate Proteoglycan (MCSP). In a particular embodiment the first antibody is directed to CEA. In another particular embodiment, the first antibody is directed to FAP.

In one embodiment the increased effector function of the second antibody is selected from the group of increased binding to an activating Fc receptor, increased ADCC, increased ADCP, increased CDC, and increased cytokine secretion. In one embodiment the increased effector function is increased binding to an activating Fc receptor. In a specific embodiment the activating Fc receptor is selected from the group of FcγRIIIa, FcγRI, and FcRγIIa. In one embodiment the activating Fc receptor is FcγRIIIa. In one embodiment the increased effector function is increased ADCC. In one embodiment the increased effector function is increased binding to an activating Fc receptor and increased ADCC.

In one embodiment the second antibody is engineered by introduction of one or more amino acid mutations in the Fc region. In a specific embodiment the amino acid mutations are amino acid substitutions. In one embodiment the second antibody is engineered by modification of the glycosylation in the Fc region. In a specific embodiment the modification of the glycosylation in the Fc region is an increased proportion of non-fucosylated oligosaccharides in the Fc region, as compared to a non-engineered antibody. In an even more specific embodiment the increased proportion of non-fucosylated oligosaccharides in the Fc region is at least 20%, preferably at least 50%, most preferably at least 70% of non-fucosylated oligosaccharides in the Fc region. In another specific embodiment the modification of the glycosylation in the Fc region is an increased proportion of bisected oligosaccharides in the Fc region, as compared to a non-engineered antibody. In an even more specific embodiment the increased proportion of bisected oligosaccharides in the Fc region is at least about 20%, preferably at least 50%, and most preferably at least 70% of bisected oligosaccharides in the Fc region. In yet another specific embodiment the modification of the glycosylation in the Fc region is an increased proportion of bisected, non-fucosylated oligosaccharides in the Fc region, as compared to a non-engineered antibody. Preferably the second antibody has at least about 25%, at least about 35%, or at least about 50% of bisected, non-fucosylated oligosaccharides in the Fc region. In a particular embodiment the second antibody is engineered to have an increased proportion of non-fucosylated oligosaccharides in the Fc region as compared to a non-engineered antibody. An increased proportion of non-fucosylated oligosaccharides in the Fc region of an antibody results in the antibody having increased effector function, in particular increased ADCC. In a particular embodiment the non-fucosylated oligosaccharides are bisected, non-fucosylated oligosaccharides.

In one embodiment the second antibody is a full-length IgG class antibody, particularly a full-length $IgG_1$ subclass antibody. In certain embodiments the second antibody is directed to an antigen presented on a tumor cell. In a specific embodiment the second antibody is directed to an antigen selected from the group of CD20, Epidermal Growth Factor Receptor (EGFR), HER2, HER3, Insulin-like Growth Factor 1 Receptor (IGF-1R), c-Met, CUB domain-containing protein-1 (CDCP1), Carcinoembryonic Antigen (CEA) and Melanoma-associated Chondroitin Sulfate Proteoglycan (MCSP).

In a particular embodiment the second antibody is an anti-CD20 antibody engineered to have an increased proportion of non-fucosylated oligosaccharides in the Fc region as compared to a non-engineered antibody. Suitable anti-CD20 antibodies are described in WO 2005/044859, which is incorporated herein by reference in its entirety. In another particular embodiment the second antibody is an anti-EGFR antibody engineered to have an increased proportion of non-fucosylated oligosaccharides in the Fc region as compared to a non-engineered antibody. Suitable anti-EGFR antibodies are described in WO 2006/082515 and WO 2008/017963, each of which is incorporated herein by reference in its entirety. In a further particular embodiment the second antibody is an anti-IGF-1R antibody engineered to have an increased proportion of non-fucosylated oligosaccharides in the Fc region as compared to a non-engineered antibody. Suitable anti-IGF-1R antibodies are described in WO 2008/077546, which is incorporated herein by reference in its entirety. In yet another particular embodiment the second antibody is an anti-CEA antibody engineered to have an increased proportion of non-fucosylated oligosaccharides in the Fc region as compared to a non-engineered antibody. Suitable anti-CEA antibodies are described in PCT publication number WO 2011/023787, which is incorporated herein by reference in its entirety. In yet another particular embodiment the second antibody is an anti-HER3 antibody engineered to have an increased proportion of non-fucosylated oligosaccharides in the Fc region as compared to a non-engineered antibody. Suitable anti-HER3 antibodies are described in PCT publication number WO 2011/076683, which is incorporated herein by reference in its entirety. In yet another particular embodiment the second antibody is an anti-CDCP1 antibody engineered to have an increased proportion of non-fucosylated oligosaccharides in the Fc region as compared to a non-engineered antibody. Suitable anti-CDCP1 antibodies are described in PCT publication number WO 2011/023389, which is incorporated herein by reference in its entirety. In one embodiment the second antibody is engineered to have modified glycosylation in the Fc region, as compared to a non-engineered antibody, by producing the antibody in a host cell having altered activity of one or more glycosyltransferase.

In one embodiment the second antibody is engineered to have an increased proportion of non-fucosylated oligosaccharides in the Fc region, as compared to a non-engineered antibody, by producing the antibody in a host cell having increased β(1,4)-N-acetylglucosaminyltransferase III (GnTIII) activity. In a particular embodiment the host cell additionally has increased α-mannosidase II (ManII) activity. In another embodiment the second antibody is engineered to have an increased proportion of non-fucosylated oligosaccharides in the Fc region, as compared to a non-engineered antibody, by producing the antibody in a host cell having decreased α(1,6)-fucosyltransferase activity.

In one embodiment the disease is a disorder treatable by stimulation of effector cell function. In one embodiment the disease is a cell proliferation disorder. In a particular embodiment the disease is cancer. In a specific embodiment the cancer is selected from the group of lung cancer, colorectal cancer, renal cancer, prostate cancer, breast cancer, head and neck cancer, ovarian cancer, brain cancer, lymphoma, leukemia, and skin cancer. In one embodiment the individual is a mammal. In a particular embodiment the individual is a human.

In a particular embodiment, the invention provides a combination of
(a) an immunoconjugate comprising a first full-length IgG class antibody engineered to have reduced effector function by introduction of one or more amino acid mutation in the Fc region and a cytokine, wherein the effector moiety is fused at its amino-terminal amino acid to the carboxy-terminus of one of the heavy chains of the first antibody, optionally through a peptide linker, and
(b) a second full-length IgG class antibody engineered to have increased effector function by modification of the glycosylation in the Fc region, for use in treating a disease in an individual in need thereof. In another aspect the invention provides a pharmaceutical composition comprising (a) an immunoconjugate comprising a first antibody engineered to have reduced effector function and an effector moiety, and (b) a second antibody engineered to have increased effector function, in a pharmaceutically acceptable carrier.

The invention also encompasses the use of (a) an immunoconjugate comprising a first antibody engineered to have reduced effector function and an effector moiety, and (b) a second antibody engineered to have increased effector function, for the manufacture of a medicament for the treatment of a disease in an individual.

The invention further provides a method of treating a disease in an individual, comprising administering to the individual a combination of (a) an immunoconjugate comprising a first antibody engineered to have reduced effector function and an effector moiety, and (b) a second antibody engineered to have increased effector function, in a therapeutically effective amount.

Also provided by the invention is a method of stimulating effector cell function in an individual, comprising administering to the individual a combination of (a) an immunoconjugate comprising a first antibody engineered to have reduced effector function and an effector moiety, and (b) a second antibody engineered to have increased effector function, in an amount effective to stimulate effector cell function.

In a further aspect the invention provides a kit intended for the treatment of a disease, comprising in the same or in separate containers (a) an immunoconjugate comprising a first antibody engineered to have reduced effector function and an effector moiety, (b) a second antibody engineered to have increased effector function, and (c) optionally a package insert comprising printed instructions directing the use of the combined treatment as a method for treating the disease.

It is understood that the immunoconjugate and the second antibody used in the pharmaceutical composition, use, methods and kit according to the invention may incorporate any of the features, singly or in combination, described in the preceding paragraphs in relation to the second antibodies and immunoconjugates useful for the invention.

SHORT DESCRIPTION OF THE DRAWINGS

Figure 1B:
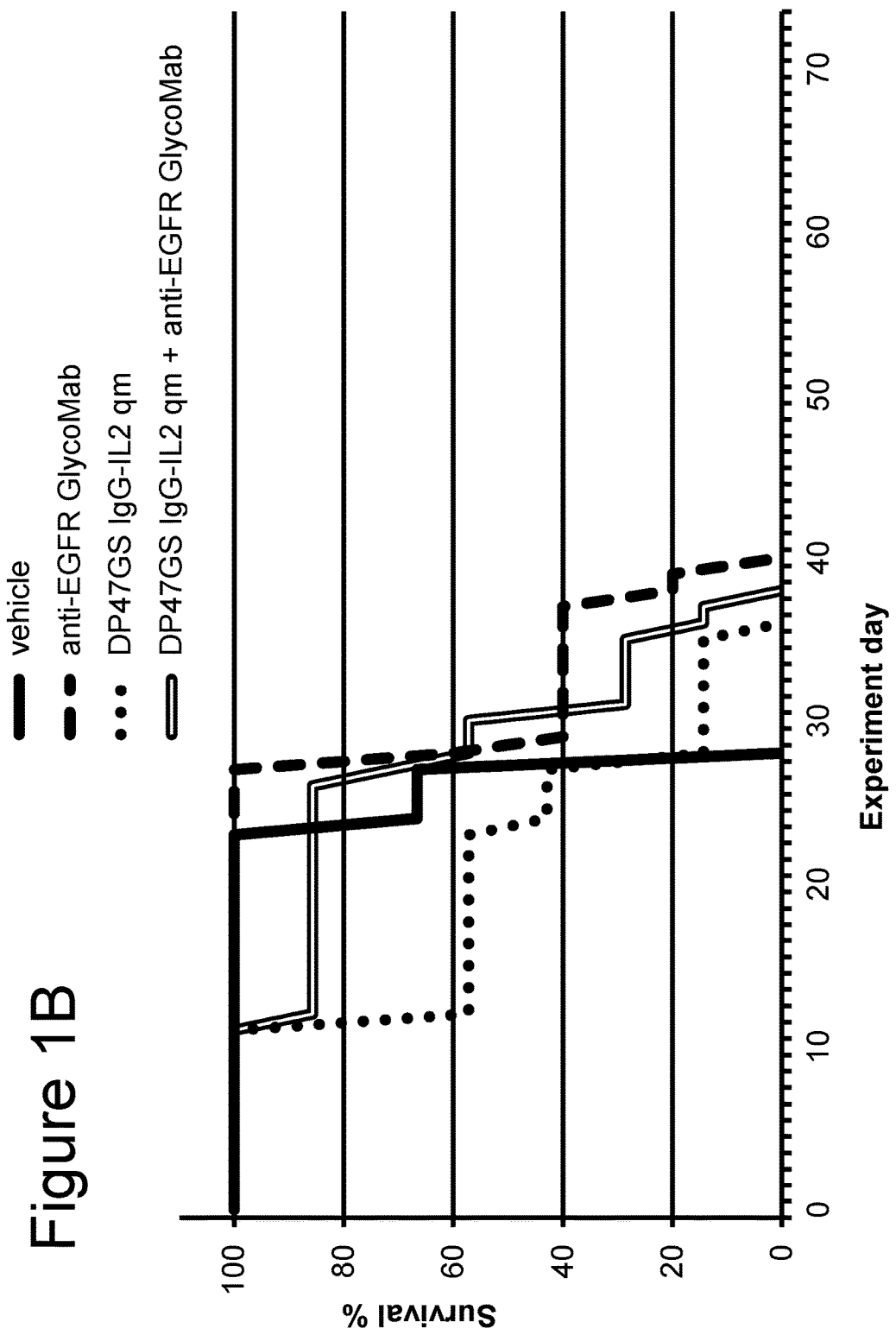

FIG. 1A-B. The FAP-targeted 28H1 IgG-IL-2 immunoconjugate (A) or the untargeted DP47GS IgG-IL-2 immunoconjugate (B), comprising the IL-2 quadruple mutant (qm) that lacks binding to CD25, and the anti-EGFR GLYCOMAB were tested in the human head and neck carcinoma cell line FaDu, intralingually injected into SCID mice. The data show that the combination of the 28H1 IgG-IL2 qm immunoconjugate, but not the DP47GS IgG-IL2 qm immunoconjugate, and the anti-EGFR GLYCOMAB mediates superior efficacy in terms of enhanced median survival compared to the respective immunoconjugate or the anti-EGFR GLYCOMAB alone (see Example 1).

Figure 2A:
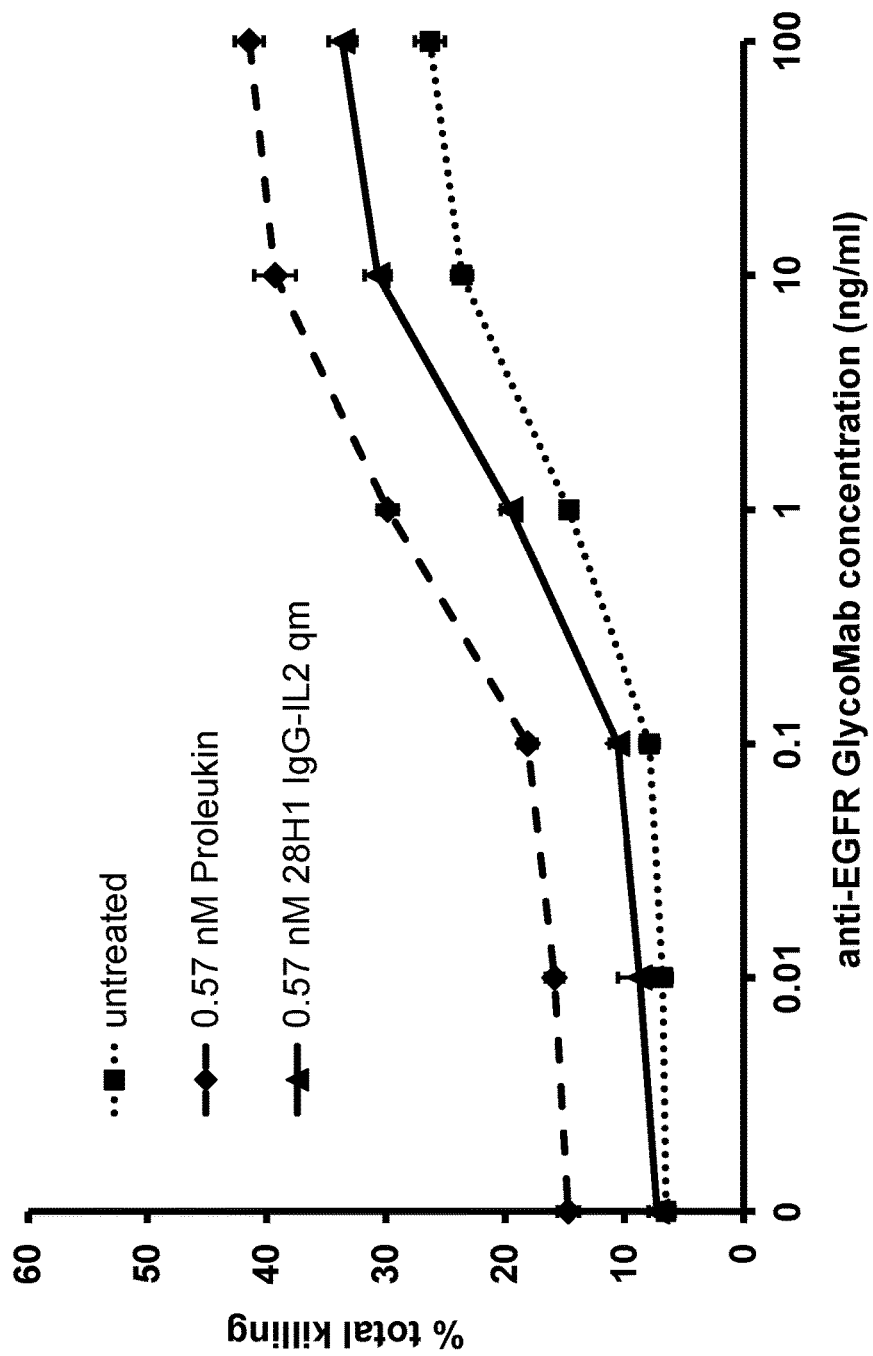

FIG. 2A-B. Overall A549 tumor cell killing by PBMCs (E:T=10:1, 4 hours), pre-treated or not with 0.57 nM (A) or 5.7 nM (B) FAP-targeted 28H1 IgG-IL2 qm immunoconjugate or IL-2 (Proleukin), in the presence of different concentrations of anti-EGFR GLYCOMAB (see Example 2).

Figure 3A:
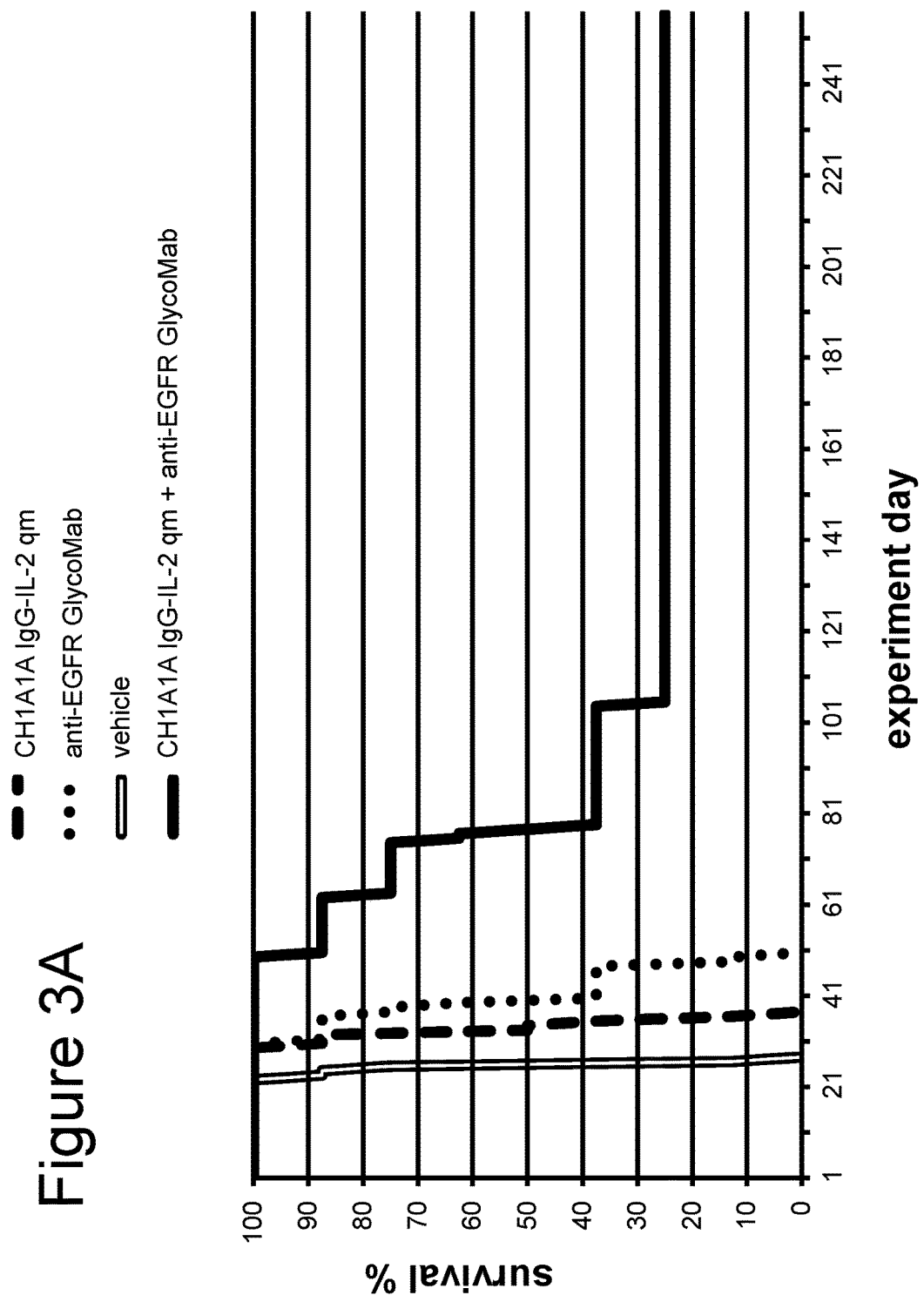
Figure 3B:
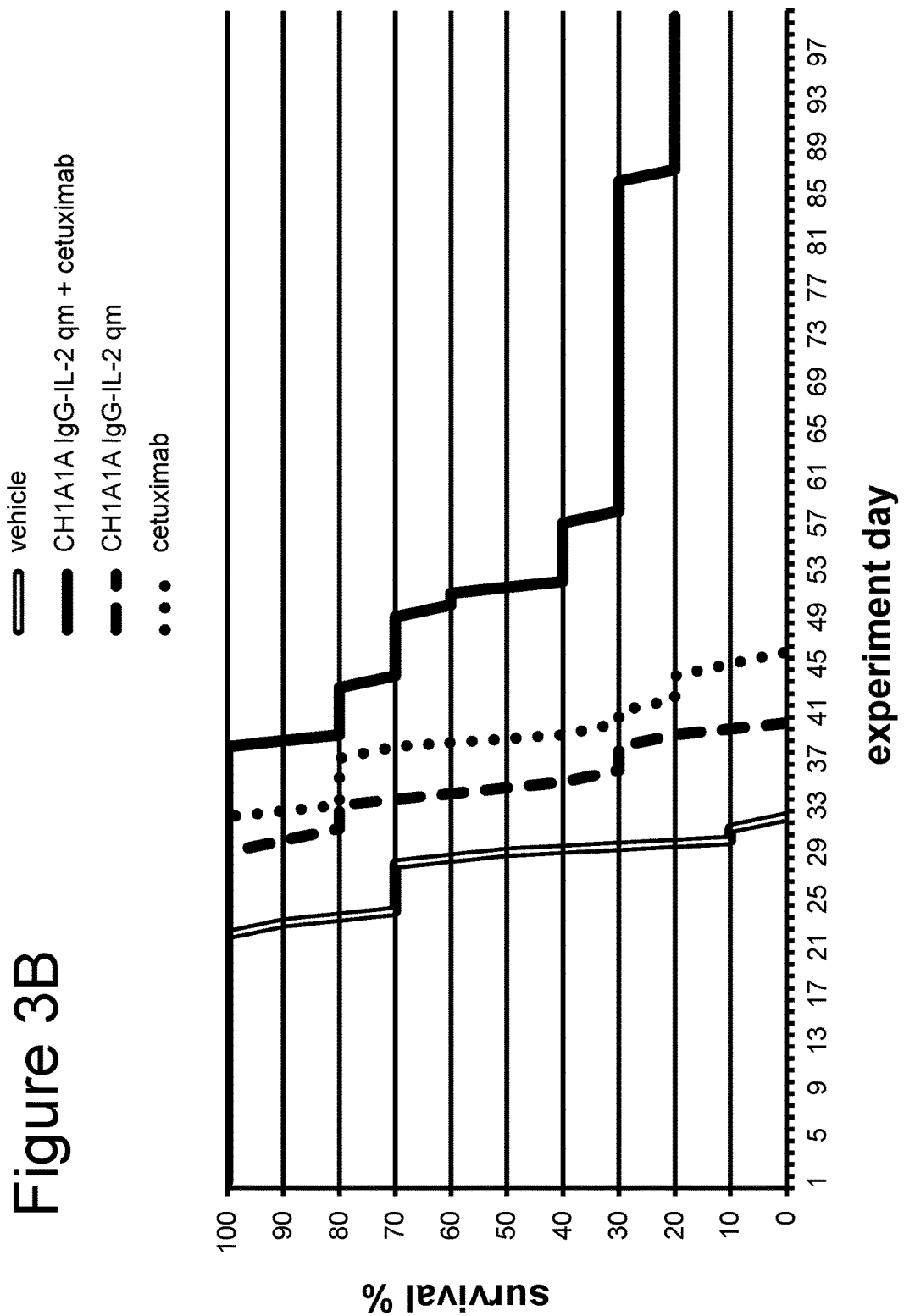

FIG. 3A-B. The CEA-targeted CH1A1A IgG-IL-2 immunoconjugate comprising the IL-2 quadruple mutant (qm) that lacks binding to CD25, and the anti-EGFR GLYCOMAB (A) or cetuximab (B) were tested in the human colorectal carcinoma cell line LS174T, intrasplenically injected into SCID FcγRIII transgenic mice. The data show that the combination of the CH1A1A IgG-IL2 qm immunoconjugate and the anti-EGFR GLYCOMAB mediates superior efficacy in terms of enhanced median and overall survival compared to the respective immunoconjugate, the anti-EGFR GLYCOMAB or cetuximab alone, as well as the combination of the CH1A1A IgG-IL2 qm immunoconjugate and cetuximab (see Example 3).

FIG. 4A-B. The CEA-targeted CH1A1A IgG-IL-2 immunoconjugate comprising the IL-2 quadruple mutant (qm) that lacks binding to CD25, and the anti-EGFR GLYCOMAB (A) or cetuximab (B) were tested in the human lung carcinoma cell line A549, intravenously injected into SCID FcγRIII transgenic mice. The data show that the combination of the CH1A1A IgG-IL2 qm immunoconjugate and the anti-EGFR GLYCOMAB mediates superior efficacy in terms of enhanced median and overall survival compared to the respective immunoconjugate or the anti-EGFR GLYCOMAB alone, as well as the combination of the CH1A1A IgG-IL2 qm immunoconjugate and cetuximab (see Example 4).

Figure 5:
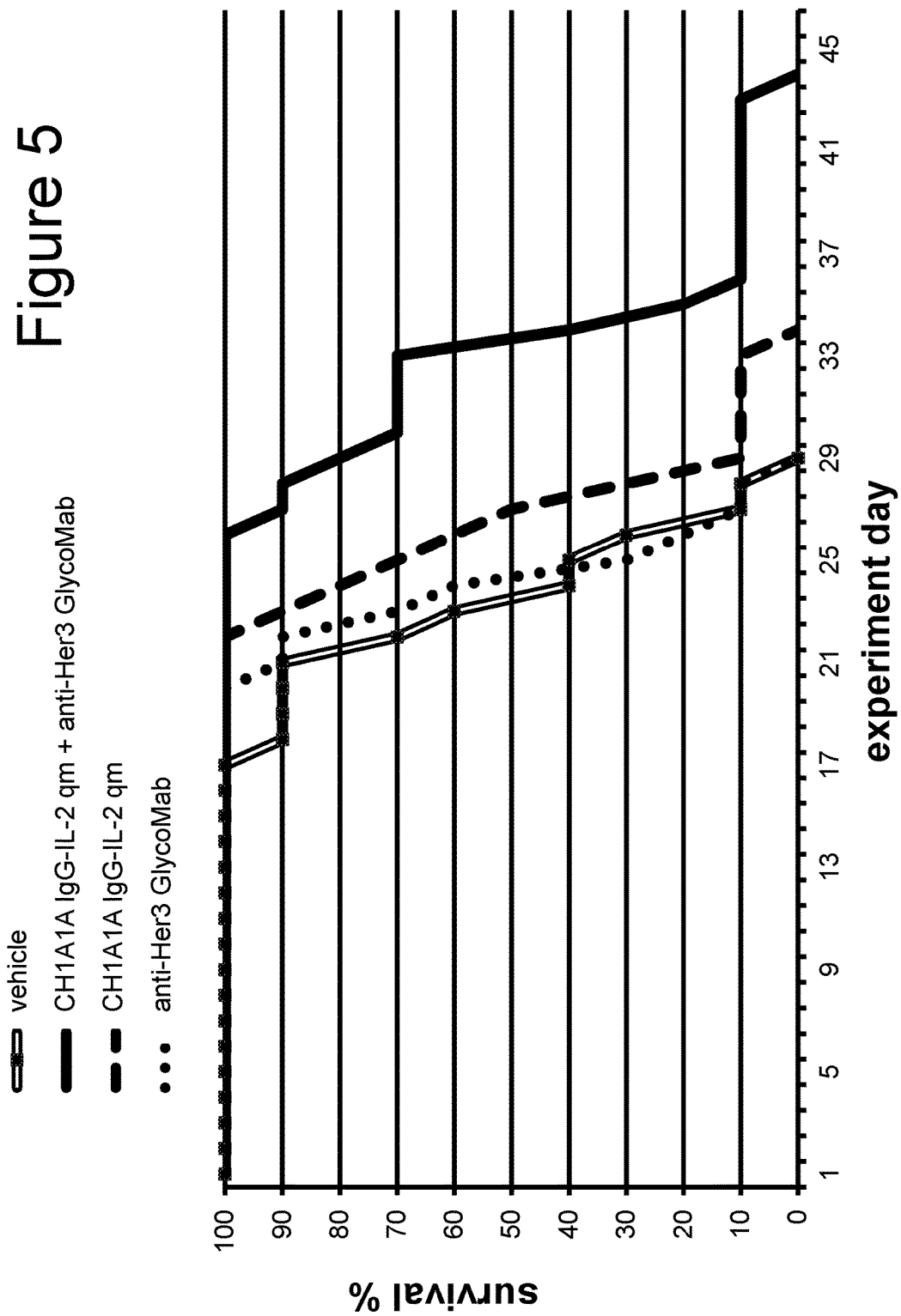

FIG. 5. The CEA-targeted CH1A1A IgG-IL-2 immunoconjugate comprising the IL-2 quadruple mutant (qm) that lacks binding to CD25, and the anti-Her3 GLYCOMAB were tested in the human colorectal carcinoma cell line LS174T, intrasplenically injected into SCID FcγRIII transgenic mice. The data show that the combination of the CH1A1A IgG-IL2 qm immunoconjugate and the anti-Her3 GLYCOMAB mediates superior efficacy in terms of enhanced median survival compared to the respective immunoconjugate or the anti-Her3 GLYCOMAB alone (see Example 5).

Figure 6:
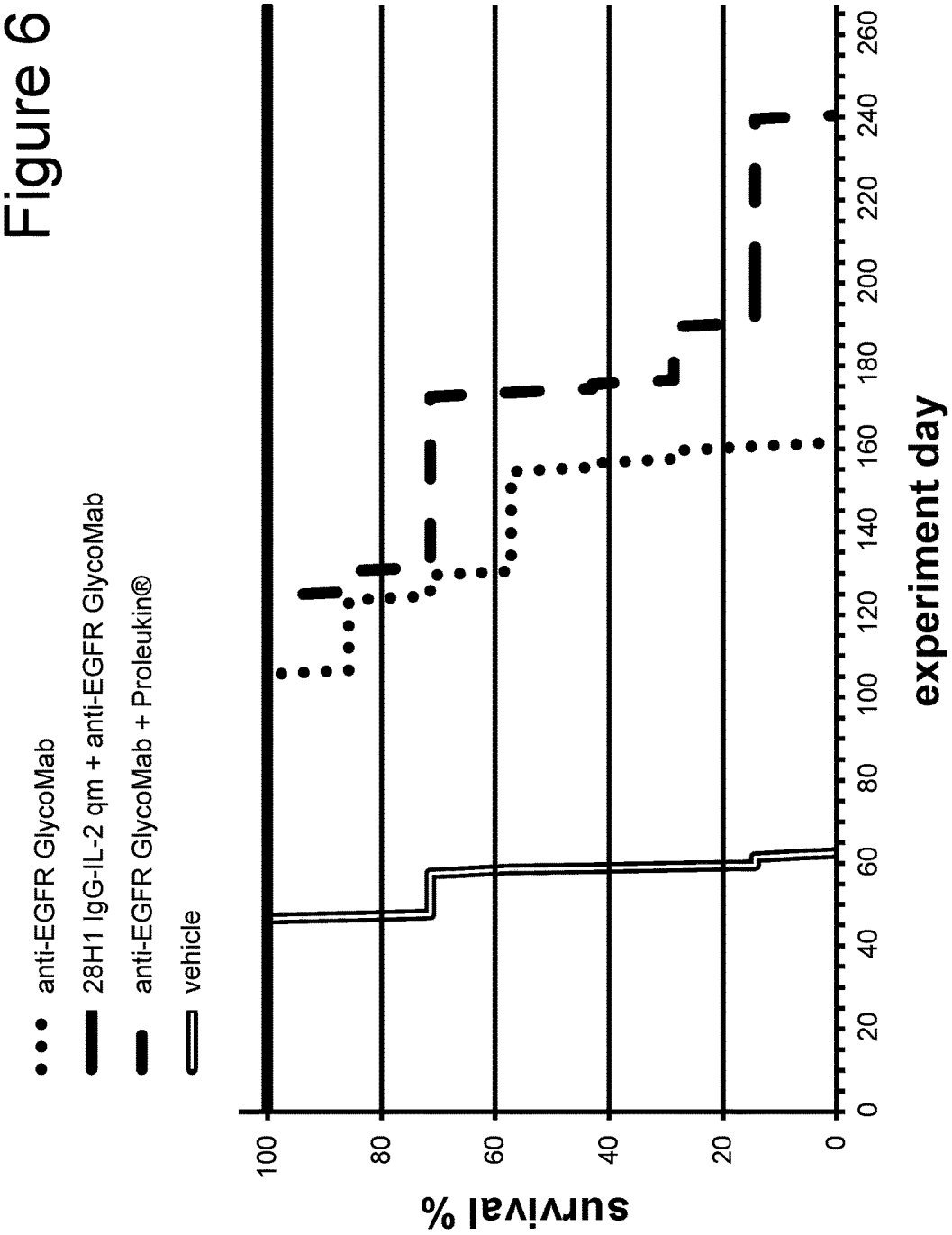

FIG. 6. The FAP-targeted 28H1 IgG-IL-2 immunoconjugate comprising the IL-2 quadruple mutant (qm) that lacks binding to CD25, and the anti-EGFR GLYCOMAB were tested in the human renal carcinoma cell line ACHN, intrarenally injected into SCID FcγRIII transgenic mice. The data show that the combination of the CH1A1A IgG-IL2 qm immunoconjugate and the anti-EGFR GLYCOMAB mediates superior efficacy in terms of enhanced median and overall survival compared to the anti-EGFR GLYCOMAB alone, or the anti-EGFR GLYCOMAB in combination with Proleukin® (see Example 6).

Figure 7:
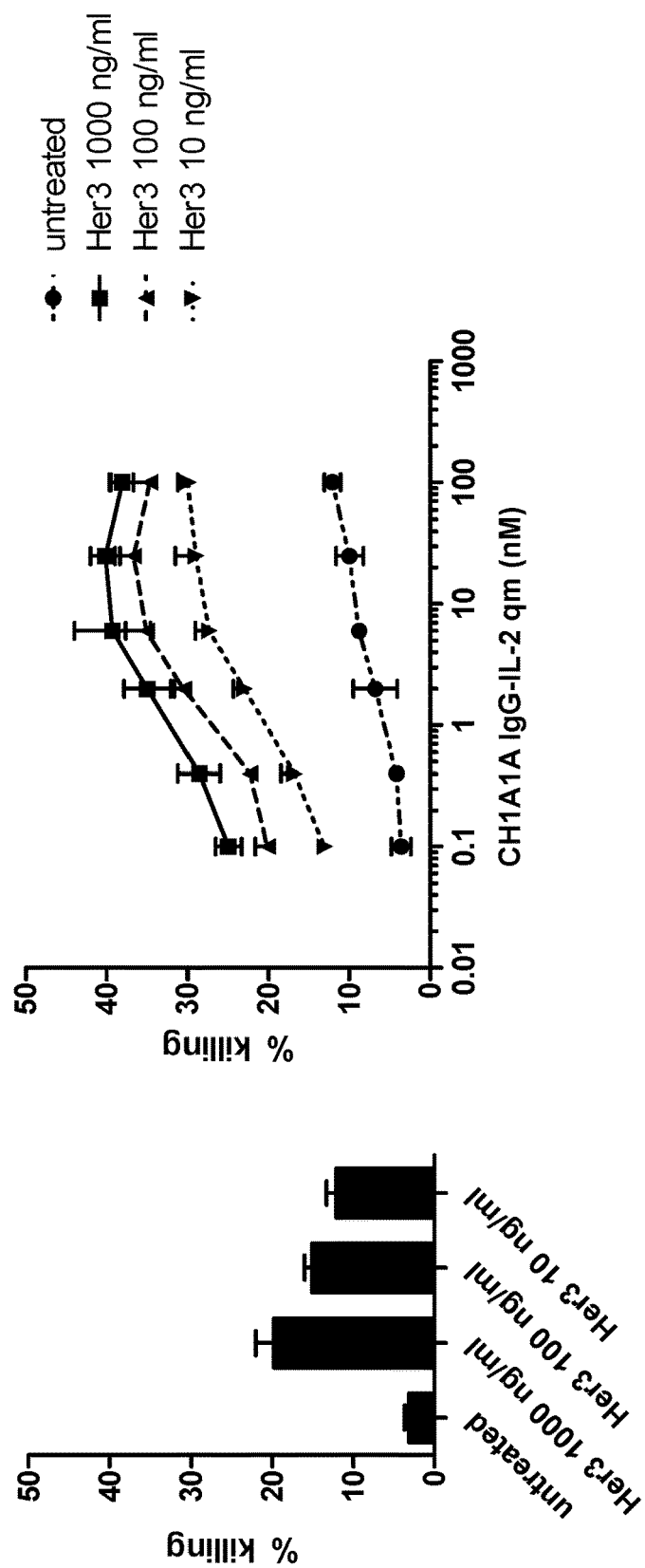

FIG. 7. Overall LS174T cell killing by PBMCs upon treatment with anti-Her3 GLYCOMAB alone (left panel), the CH1A1A IgG-IL-2 qm immunoconjugate alone (right panel) or the combination of the CH1A1A IgG-IL-2 qm immunoconjugate with the anti-Her3 GLYCOMAB (right panel).

Figure 8A:
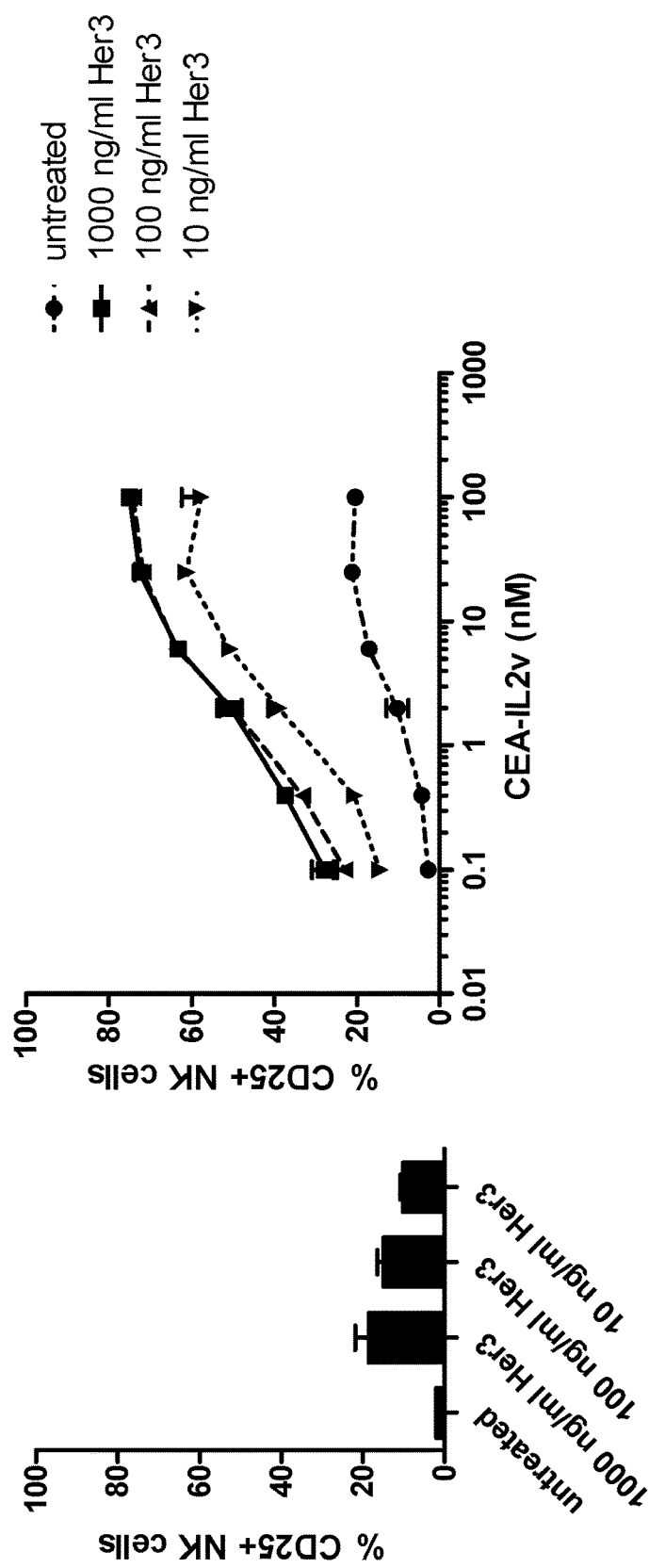
Figure 8B:
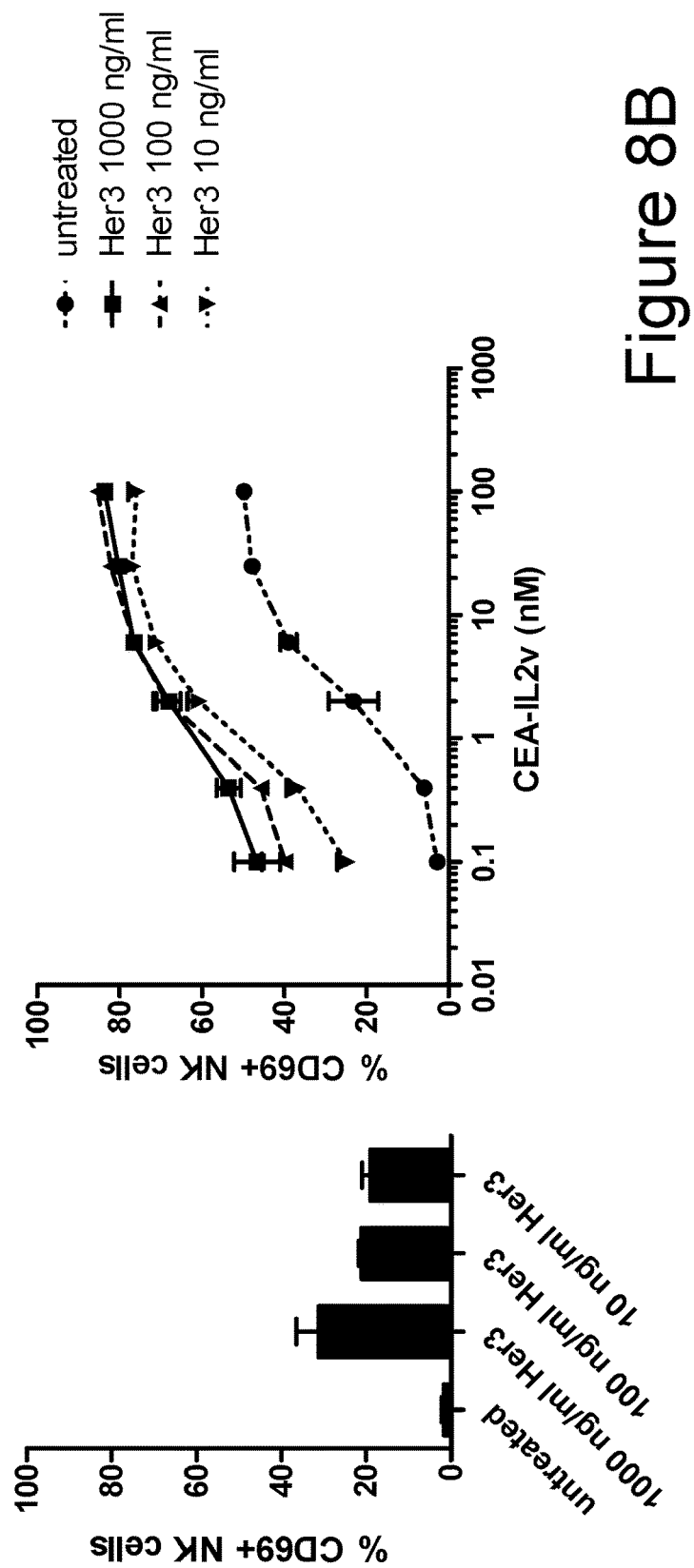

FIG. 8A-B. Expression of CD25 (A) or CD69 (B) on NK cells upon treatment with anti-Her3 GLYCOMAB alone (left panel), the CH1A1A IgG-IL-2 qm immunoconjugate alone (right panel) or the combination of the CH1A1A IgG-IL-2 qm immunoconjugate with the anti-Her3 GLYCOMAB (right panel).

DETAILED DESCRIPTION OF THE INVENTION

In a first aspect the present invention provides a combination of (a) an immunoconjugate comprising a first antibody engineered to have reduced effector function and an effector moiety, and (b) a second antibody engineered to have increased effector function, for use in treating a disease in an individual in need thereof.

The invention further provides a method of treating a disease in an individual, comprising administering to the individual a combination of (a) an immunoconjugate comprising a first antibody engineered to have reduced effector function and an effector moiety, and (b) a second antibody engineered to have increased effector function, in a therapeutically effective amount.

Also provided by the invention is a method of stimulating effector cell function in an individual, comprising administering to the individual a combination of (a) an immunoconjugate comprising a first antibody engineered to have reduced effector function and an effector moiety, and (b) a second antibody engineered to have increased effector function, in an amount effective to stimulate effector cell function.

Definitions

Terms are used herein as generally used in the art, unless otherwise defined in the following.

As used herein, the term "immunoconjugate" refers to a polypeptide molecule that includes at least one effector moiety and an antibody. In certain embodiments, the immunoconjugate comprises not more than one effector moiety. Particular immunoconjugates according to the invention essentially consist of one effector moiety and an antibody joined by one or more peptide linkers. Particular immunoconjugates according to the invention are fusion proteins, i.e. the components of the immunconjugate are joined by peptide bonds.

As used herein, the term "control antibody" refers to an antibody as it would exist free of effector moieties. For example, when comparing a IgG-IL2 immunoconjugate as described herein with a control antibody, the control antibody is free IgG, wherein the IgG-IL2 immunoconjugate and the free IgG molecule can both specifically bind to the same antigenic determinant.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antibody binds, forming an antibody-antigen complex. Useful antigenic determinants can be found, for example, on the surfaces of tumor cells, on the surfaces of virus-infected cells, on the surfaces of other diseased cells, free in blood serum, and/or in the extracellular matrix (ECM).

By "specifically binds" is meant that the binding is selective for the antigen and can be discriminated from unwanted or non-specific interactions. The ability of an antibody to bind to a specific antigenic determinant can be measured either through an enzyme-linked immunosorbent assay (ELISA) or other techniques familiar to one of skill in the art, e.g. surface plasmon resonance technique (analyzed on a BIAcore instrument) (Liljeblad et al., Glyco J 17, 323-329 (2000)), and traditional binding assays (Heeley, Endocr Res 28, 217-229 (2002)).

The terms "anti-[antigen] antibody" and "an antibody that binds to [antigen]" refer to an antibody that is capable of binding the respective antigen with sufficient affinity such that the antibody is useful as a diagnostic and/or therapeutic agent in targeting the antigen. In one embodiment, the extent of binding of an anti-[antigen] antibody to an unrelated protein is less than about 10% of the binding of the antibody to the antigen as measured, e.g., by a radioimmunoassay (RIA). In certain embodiments, an antibody that binds to [antigen] has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

According to one embodiment, $K_D$ is measured by surface plasmon resonance using a BIACORE® T100 machine (GE Healthcare) at 25° C. with ligand (e.g. effector moiety receptor, Fc receptor or target antigen) immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 μg/ml before injection at a flow rate of 10 μl/minute to achieve approximately 100-5000 response units (RU) of coupled protein. Following the injection of the ligand, 1 M ethanolamine is injected to block unreacted groups. For kinetics measurements, three- to five-fold serial dilutions of immunoconjugate (range between ~0.01 nM to 300 nM) are injected in HBS-EP+(GE Healthcare, 10 mM HEPES, 150 mM NaCl, 3 mM EDTA, 0.05% Surfactant P20, pH 7.4) at 25° C. at a flow rate of approximately 30-50 µl/min. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

"Reduced binding", for example reduced binding to an Fc receptor or to CD25, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

As used herein, the terms "first" and "second" with respect to antibodies, effector moieties etc., are used for convenience of distinguishing when there is more than one of each type of moiety. Use of these terms is not intended to confer a specific order or orientation of the immunoconjugate unless explicitly so stated.

As used herein, the term "effector moiety" refers to a polypeptide, e.g., a protein or glycoprotein, that influences cellular activity, for example, through signal transduction or other cellular pathways. Accordingly, the effector moiety of the invention can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e. upregulate or downregulate) of an endogenous cellular protein in cells bearing receptors for the effector moiety. Non-limiting examples of effector moieties include cytokines, growth factors, hormones, enzymes, substrates, and cofactors. The effector moiety can be associated with an antibody in a variety of configurations to form an immunoconjugate.

As used herein, the term "cytokine" refers to a molecule that mediates and/or regulates a biological or cellular function or process (e.g. immunity, inflammation, and hematopoiesis). The term "cytokine" as used herein includes "lymphokines," "chemokines," "monokines," and "interleukins". Examples of useful cytokines include, but are not limited to, GM-CSF, IL-1α, IL-1β, IL-2, IL-3, IL-4, IL-5, IL-6, IL-7, IL-8, IL-10, IL-12, IFN-α, IFN-β, IFN-γ, MIP-1α, MIP-1β, TGF-β, TNF-α, and TNF-β. Particular cytokines are IL-2 and IL-12. The term "cytokine" as used herein is meant to also include cytokine variants comprising one or more amino acid mutations in the amino acid sequences of the corresponding wild-type cytokine, such as for example the IL-2 variants described in Sauvé et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229,109; US Pat. Publ. No. 2007/0036752; WO 2008/0034473; WO 2009/061853; or hereinabove and -below.

As used herein, the term "single-chain" refers to a molecule comprising amino acid monomers linearly linked by peptide bonds. In one embodiment, the effector moiety is a single-chain effector moiety. Non-limiting examples of single-chain effector moieties include cytokines, growth factors, hormones, enzymes, substrates, and cofactors. When the effector moiety is a cytokine and the cytokine of interest is normally found as a multimer in nature, each subunit of the multimeric cytokine is sequentially encoded by the single-chain of the effector moiety. Accordingly, non-limiting examples of useful single-chain effector moieties include GM-CSF, IL-1α, IL-1β, IL-2, IL-3, IL-4, IL-5, IL-6, IL-7, IL-8, IL-10, IL-12, IFN-α, IFN-β, IFN-γ, MIP-1α, MIP-1β, TGF-β, TNF-α, and TNF-β.

As used herein, the term "control effector moiety" refers to an unconjugated effector moiety. For example, when comparing an IL-2 immunoconjugate as described herein with a control effector moiety, the control effector moiety is free, unconjugated IL-2. Likewise, e.g., when comparing an IL-12 immunoconjugate with a control effector moiety, the control effector moiety is free, unconjugated IL-12 (e.g. existing as a heterodimeric protein wherein the p40 and p35 subunits share only disulfide bond(s)).

As used herein, the term "effector moiety receptor" refers to a polypeptide molecule capable of binding specifically to an effector moiety. For example, where IL-2 is the effector moiety, the effector moiety receptor that binds to an IL-2 molecule (e.g. an immunoconjugate comprising IL-2) is the IL-2 receptor. Similarly, e.g., where IL-12 is the effector moiety of an immunoconjugate, the effector moiety receptor is the IL-12 receptor. Where an effector moiety specifically binds to more than one receptor, all receptors that specifically bind to the effector moiety are "effector moiety receptors" for that effector moiety.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin.

The terms "full-length antibody," "intact antibody," and "whole antibody" are used herein interchangeably to refer to an antibody having a structure substantially similar to a native immunoglobulin structure.

The term "immunoglobulin" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or µ (IgM), some of which may be further divided into subtypes, e.g. $γ_1$ (IgG$_1$), $γ_2$ (IgG$_2$), $γ_3$ (IgG$_3$), $γ_4$ (IgG$_4$), $α_1$ (IgA$_1$) and $α_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc region, linked via the immunoglobulin hinge region.

An "antibody fragment" refers to a molecule other than an intact antibody that comprises a portion of an intact antibody that binds the antigen to which the intact antibody binds.

Examples of antibody fragments include but are not limited to Fv, Fab, Fab', Fab'-SH, F(ab')$_2$, diabodies, linear antibodies, single-chain antibody molecules (e.g. scFv), single-domain antibodies, and multispecific antibodies formed from antibody fragments. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| V$_H$ CDR1 | 31-35 | 26-32 | 26-35 |
| V$_H$ CDR2 | 50-65 | 52-58 | 50-58 |
| V$_H$ CDR3 | 95-102 | 95-102 | 95-102 |
| V$_L$ CDR1 | 24-34 | 26-32 | 24-34 |
| V$_L$ CDR2 | 50-56 | 50-52 | 50-56 |
| V$_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing (i.e., SEQ ID NOs 3, 4, 5, 6, 7, 8, 9, etc.) are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc region" or "Fc domain" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cell-mediated cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie et al., Science 247, 1306-10 (1990)).

A "modification promoting heterodimerization" is a manipulation of the peptide backbone or the post-translational modifications of a polypeptide, e.g. an immunoglobulin heavy chain, that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two immunoglobulin heavy chains wherein further immunoconjugate components fused to each of the heavy chains (e.g. effector moiety) are not the same. In the immunoconjugates of the present invention, the modification promoting heterodimerization is in the heavy chain(s), specifically in the Fc region, of an immunoglobulin molecule. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two immunoglobulin heavy chains.

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the term "effector cells" refers to a population of lymphocytes that display effector moiety receptors, e.g. cytokine receptors, and/or Fc receptors on their surface through which they bind an effector moiety, e.g. a cytokine, and/or an Fc region of an antibody and contribute to the destruction of target cells, e.g. tumor cells. Effector cells may for example mediate cytotoxic or phagocytic effects. Effector cells include, but are not limited to, effector T cells such as $CD8^+$ cytotoxic T cells, $CD4^+$ helper T cells, γδ T cells, NK cells, lymphokine-activated killer (LAK) cells and macrophages/monocytes. Depending on their receptor expression pattern there may be different subsets of effector cells, i.e. (a) cells that express receptors for a particular effector moiety but no Fc receptors and are stimulated by the immunoconjugates but not the antibodies of the invention (e.g. T cells, expressing IL-2 receptors); (b) cells that express Fc receptors but no receptors for a particular effector moiety and are stimulated by the antibodies but not the immunoconjugates of the invention; and (c) cells that express both Fc receptors and receptors for a particular effector moiety and are simultaneously stimulated by the antibodies and the immunoconjugates of the invention (e.g. NK cells, expressing FcγIII receptors and IL-2 receptors).

As used herein, the terms "engineer, engineered, engineering," are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g. a host cell that has been manipulated to express increased levels of one or more polypeptides having β(1,4)-N-acetylglucosaminyltransferase III (GnTIII) activity), a "host cell having increased ManII activity" (e.g. a host cell that has been manipulated to express increased levels of one or more polypeptides having α-mannosidase II (ManII) activity), or a "host cell having decreased α(1,6) fucosyltransferase activity" (e.g. a host cell that has been manipulated to express decreased levels of α(1,6) fucosyltransferase).

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc region to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies and immunoconjugates used for the present invention. In one embodiment, the host cell is engineered to allow the production of an antibody with modified oligosaccharides. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetyl-glucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched GlcNAcMan$_5$GlcNAc$_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g. to express the glycosyltransferase, GnTIII, or other glycosyltransferases) by the methods described herein, is relative to the ADCC mediated by the same antibody produced by the same type of non-engineered host cells.

By "antibody having increased/reduced antibody dependent cell-mediated cytotoxicity (ADCC)" is meant an antibody having increased/reduced ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at 5×10$^6$ cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of 10$^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at 50×g for 1 minute and incubated for 1 hour at 4° C.;
   viii) 50 microliters of the PBMC suspension (point i above) are added to each well to yield an effector:target cell ratio of 25:1 and the plates are placed in an incubator under 5% CO$_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased/reduced ADCC" is defined as either an increase/reduction in the maximum percentage of specific lysis observed within the antibody concentration range tested above, and/or a reduction/increase in the concentration of antibody required to achieve one half of the maximum percentage of specific lysis observed within the antibody concentration range tested above. The increase/reduction in ADCC is relative to the ADCC, measured with the above assay, mediated by the same antibody, produced by the same type of host cells, using the same standard production, purification, formulation and storage methods, which are known to those skilled in the art, but that has not been engineered.

As used herein, "combination" (and grammatical variations thereof such as "combine" or "combining") encompasses combinations of an immunoconjugate and an antibody according to the invention wherein the immunoconjugate and the antibody are in the same or in different containers, in the same or in different pharmaceutical formulations, administered together or separately, administered simultaneously or sequentially, in any order, and administered by the same or by different routes, provided that the immunoconjugate and the antibody can simultaneously exert their biological effects in the body, i.e. simultaneously stimulate effector cells. For example "combining" an immunoconjugate and an antibody according to the invention may mean first administering the immunoconjugate in a particular pharmaceutical formulation, followed by administration of the antibody in another pharmaceutical formulation, or vice versa.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease. A therapeutically effective amount of a combination of several active ingredients may be a therapeutically effective amount of each of the active ingredients. Alternatively, to reduce the side effects caused by the treatment, a therapeutically effective amount of a combination of several active ingredients may be amounts of the individual active ingredients that are effective to produce an additive, or a superadditive or synergistic effect, and that in combination are therapeutically effective, but which may be sub-therapeutic amounts of one or several of the active ingredients if they were used alone.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, combinations of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

Immunoconjugates

Immunoconjugates useful in the present invention are polypeptide molecules that comprise an effector moiety and an antibody engineered to have reduced effector function, as compared to a corresponding non-engineered antibody.

Immunoconjugates can be prepared either by chemically conjugating the effector moiety to the antibody, or by expressing the effector moiety and the antibody as a fusion protein (see, e.g. Nakamura and Kubo, Cancer 80, 2650-2655 (1997); and Becker et al., Proc Natl Acad Sci USA 93, 7826-7831 (1996)). For use in the present invention, immunoconjugates expressed as fusion proteins are generally preferred. Accordingly, in certain embodiments the effector moiety shares an amino- or carboxy-terminal peptide bond with the antibody (i.e. the immunoconjugate is a fusion protein). In such immunoconjugates, an effector moiety may for example be fused to an immunoglobulin heavy or light chain. Particularly useful in the present invention are immunoconjugates comprising a full-length IgG class antibody, particularly a full-length $IgG_1$ sub-class antibody.

In one embodiment, the effector moiety is a single-chain effector moiety. In one embodiment the effector moiety is a cytokine. The antibodies and effector moieties of the immunoconjugate include those that are described in detail herein above and below. The antibody of the immunoconjugate can be directed against a variety of target molecules (e.g. an antigenic determinant on a protein molecule expressed on a tumor cell or tumor stroma). Non-limiting examples of antibodies are described herein. Particularly useful immunoconjugates as described herein typically exhibit one or more of the following properties: high specificity of action, reduced toxicity, good produceability and/or improved stability, particularly as compared to immunoconjugates of different configurations targeting the same antigenic determinants and carrying the same effector moieties. Particular immunoconjugates for use in the present invention are further described in PCT publication number WO 2012/146628, the entire contents of which are incorporated herein by reference.

Immunoconjugate Formats

The immunoconjugates described in PCT publication number WO 2012/146628 comprise not more than one effector moiety. Accordingly, in a particular embodiment, the immunoconjugate for use in the present invention comprises not more than one effector moiety. In a particular embodiment, the effector moiety is a single chain effector moiety. The antibody comprised in the immunoconjugates according to the invention is particularly a full-length IgG class antibody, more particularly a full-length $IgG_1$ sub-class antibody. In one embodiment the antibody is human. In other embodiments, the antibody is humanized or chimeric. In one embodiment, the antibody comprises a human Fc region, more particularly a human IgG Fc region, most particularly a human $IgG_1$ Fc region. The antibodies useful in the invention may comprise a human Ig gamma-1 heavy chain constant region, as set forth in SEQ ID NO: 124 (i.e. the antibodies are of human $IgG_1$ subclass).

In one embodiment the effector moiety shares an amino- or carboxy-terminal peptide bond with the antibody. In one embodiment, the immunoconjugate essentially consists of an effector moiety and an antibody, particularly an IgG class antibody, more particularly an $IgG_1$ sub-class antibody, joined by one or more peptide linkers. In a specific embodiment the effector moiety is fused at its amino-terminal amino acid to the carboxy-terminal amino acid of one of the immunoglobulin heavy chains, optionally through a peptide linker.

In certain embodiments, particularly where the immunoconjugate comprises only a single effector moiety, the antibody comprises in the Fc region a modification promoting heterodimerization of two non-identical immunoglobulin heavy chains. The site of most extensive protein-protein interaction between the two polypeptide chains of a human IgG Fc region is in the CH3 domain of the Fc region. Thus, in one embodiment said modification is in the CH3 domain of the Fc region. In a specific embodiment said modification is a knob-into-hole modification, comprising a knob modification in one of the immunoglobulin heavy chains and a hole modification in the other one of the immunoglobulin heavy chains. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two immunoglobulin heavy chains, and the hole modification comprises the amino acid substitutions T366S, L368A and Y407V in the other one of the two immunoglobulin heavy chains (Kabat numbering). In a further specific embodiment, immunoglobulin heavy chain comprising the knob modification additionally comprises the amino acid substitution S354C, and the immunoglobulin heavy chain comprising the hole modification additionally comprises the amino acid substitution Y349C. Introduction of these two cysteine residues results in formation of a disulfide bridge between the two heavy chains, further stabilizing the dimer (Carter, J Immunol Methods 248, 7-15 (2001)).

In a particular embodiment the effector moiety is joined to the carboxy-terminal amino acid of the immunoglobulin heavy chain comprising the knob modification.

In an alternative embodiment a modification promoting heterodimerization of two non-identical polypeptide chains comprises a modification mediating electrostatic steering effects, e.g. as described in PCT publication WO 2009/089004. Generally, this method involves replacement of one or more amino acid residues at the interface of the two polypeptide chains by charged amino acid residues so that homodimer formation becomes electrostatically unfavorable but heterodimerization electrostatically favorable.

An Fc region confers to the immunoconjugate favorable pharmacokinetic properties, including a long serum half-life which contributes to good accumulation in the target tissue and a favorable tissue-blood distribution ratio. At the same time it may, however, lead to undesirable targeting of the immunoconjugate to cells expressing Fc receptors rather than to the preferred antigen-bearing cells. Moreover, the co-activation of Fc receptor signaling pathways may lead to cytokine release which, in combination with the effector moiety and the long half-life of the immunoconjugate, results in excessive activation of cytokine receptors and severe side effects upon systemic administration. In line with this, conventional IgG-IL-2 immunoconjugates have been described to be associated with infusion reactions (see e.g. King et al., J Clin Oncol 22, 4463-4473 (2004)).

Accordingly, the antibody comprised in the immunoconjugate is engineered to have reduced effector function, as compared to a corresponding non-engineered antibody. In particular embodiments, the reduced effector function is reduced binding to an activating Fc receptor. In one such embodiment the antibody comprises in its Fc region one or more amino acid mutation that reduces the binding affinity of the immunoconjugate to an activating Fc receptor. Typically, the same one or more amino acid mutation is present in each of the two immunoglobulin heavy chains. In one embodiment said amino acid mutation reduces the binding affinity of the immunoconjugate to the activating Fc receptor by at least 2-fold, at least 5-fold, or at least 10-fold. In embodiments where there is more than one amino acid mutation that reduces the binding affinity of the immunoconjugate to the activating Fc receptor, the combination of these amino acid mutations may reduce the binding affinity of the immunoconjugate to the activating Fc receptor by at least 10-fold, at least 20-fold, or even at least 50-fold. In one embodiment the immunoconjugate comprising an engineered antibody exhibits less than 20%, particularly less than 10%, more particularly less than 5% of the binding affinity to an activating Fc receptor as compared to an immunoconjugate comprising a non-engineered antibody. In a specific embodiment the activating Fc receptor is an Fcγ receptor, more specifically an FcγRIIIa, FcγRI or FcγRIIa receptor. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the antibody to said receptor, is achieved when the antibody (or the immunoconjugate comprising said antibody) exhibits greater than about 70% of the binding affinity of a non-engineered form of the antibody (or the immunoconjugate comprising said non-engineered form of the antibody) to FcRn. Antibodies, or immunoconjugates comprising said antibodies, may exhibit greater than about 80% and even greater than about 90% of such affinity. In one embodiment the amino acid mutation is an amino acid substitution. In one embodiment the antibody, particularly a human $IgG_1$ subclass antibody, comprises an amino acid substitution at position P329 of the immunoglobulin heavy chain (Kabat numbering). In a more specific embodiment the amino acid substitution is P329A or P329G, particularly P329G. In one embodiment the antibody comprises a further amino acid substitution at a position selected from 5228, E233, L234, L235, N297 and P331 of the immunoglobulin heavy chain. In a more specific embodiment the further amino acid substitution is S228P, E233P, L234A, L235A, L235E, N297A, N297D or P331S. In a particular embodiment the antibody comprises amino acid substitutions at positions P329, L234 and L235 of the immunoglobulin heavy chain (Kabat numbering). In a more particular embodiment the antibody comprises the amino acid substitutions L234A, L235A and P329G (LALA P329G) in the immunoglobulin heavy chain. This combination of amino acid substitutions almost particularly efficiently abolishes Fcγ receptor binding of a human IgG molecule, and hence reduces effector function including antibody-dependent cell-mediated cytotoxicity (ADCC), as described in PCT publication no. WO 2012/130831, incorporated herein by reference in its entirety. WO 2012/130831 also describes methods of preparing such mutant antibodies and methods for determining its properties such as Fc receptor binding or effector functions.

Mutant antibodies can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of antibodies or immunoconjugates comprising an antibody for Fc receptors may be evaluated using cell lines known to express particular Fc receptors, such as NK cells expressing FcγIIIa receptor.

In some embodiments the antibody of the immunoconjugate is engineered to have reduced effector function, particularly reduced ADCC, as compared to a non-engineered antibody. Effector function of an antibody, or an immunoconjugate comprising an antibody, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments binding of the antibody to a complement component, specifically to C1q, is altered. Accordingly, in some embodiments wherein the antibody is engineered to have reduced effector function, said reduced effector function includes reduced CDC. C1q binding assays may be carried out to determine whether the immunoconjugate is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In some embodiments, the immunoconjugate comprises one or more proteolytic cleavage sites located between effector moiety and antibody. Components of the immunoconjugate may be linked directly or through various linkers, particularly peptide linkers comprising one or more amino acids, typically about 2-20 amino acids, that are described herein or are known in the art. Suitable, non-immunogenic peptide linkers include, for example, $(G4S)_n$, $(SG_4)_n$ or $G_4(SG_4)_n$ peptide linkers, wherein n is generally a number between 1 and 10, typically between 2 and 4.

Antibodies of Immunoconjugates

The antibody of the immunoconjugate of the invention is generally an immunoglobulin molecule that binds to a specific antigenic determinant and is able to direct the entity to which it is attached (e.g. an effector moiety) to a target site, for example to a specific type of tumor cell or tumor stroma that bears the antigenic determinant. The immunoconjugate can bind to antigenic determinants found, for example, on the surfaces of tumor cells, on the surfaces of virus-infected cells, on the surfaces of other diseased cells, free in blood serum, and/or in the extracellular matrix (ECM). Non-limiting examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1 MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2. Non-limiting examples of viral antigens include influenza virus hemagglutinin, Epstein-Barr virus LMP-1, hepatitis C virus E2 glycoprotein, HIV gp160, and HIV gp120. Non-limiting examples of ECM antigens include syndecan, heparanase, integrins, osteopontin, link, cadherins, laminin, laminin type EGF, lectin, fibronectin, notch, tenascin, and matrixin. The immunoconjugates of the invention can bind to the following specific non-limiting examples of cell surface antigens: FAP, Her2, EGFR, IGF-1R, CD2 (T-cell surface antigen), CD3 (heteromultimer associated with the TCR), CD22 (B-cell receptor), CD23 (low affinity IgE receptor), CD25 (IL-2 receptor a chain), CD30 (cytokine receptor), CD33 (myeloid cell surface antigen), CD40 (tumor necrosis factor receptor), IL-6R (IL6 receptor), CD20, MCSP, c-Met, CUB domain-containing protein-1 (CDCP1), and PDGFβR (β platelet-derived growth factor receptor).

In certain embodiments the antibody is directed to an antigen presented on a tumor cell or in a tumor cell environment. In a specific embodiment the antibody is directed to an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and Melanoma-associated Chondroitin Sulfate Proteoglycan (MCSP).

The antibody can be any type of antibody or fragment thereof that retains specific binding to an antigenic determinant and comprises an Fc region. In one embodiment the antibody is a full-length antibody. Particularly preferred antibodies are immunoglobulins of the IgG class, specifically of the IgG$_1$ subclass.

In one embodiment, the immunoconjugate comprises an antibody that is specific for the A1 and/or the A4 domain of Tenascin (TNC-A1 or TNC-A4 or TNC-A1/A4). In a specific embodiment, the antibody of the immunoconjugate comprises a heavy chain variable region sequence that is at least about 80%, 85%, 90%, 95%, 96%, 97%, 98%, 99% or 100% identical to either SEQ ID NO: 8 or SEQ ID NO: 9, or variants thereof that retain functionality. In another specific embodiment, the antibody of the immunoconjugate comprises a light chain variable region sequence that is at least about 80%, 85%, 90%, 95%, 96%, 97%, 98%, 99% or 100% identical to either SEQ ID NO: 6 or SEQ ID NO: 7, or variants thereof that retain functionality. In a more specific embodiment, the antibody of the immunoconjugate comprises a heavy chain variable region sequence that is at least about 80%, 85%, 90%, 95%, 96%, 97%, 98%, 99% or 100% identical to either SEQ ID NO: 8 or SEQ ID NO: 9 or variants thereof that retain functionality, and a light chain variable region sequence that is at least about 80%, 85%, 90%, 95%, 96%, 97%, 98%, 99% or 100% identical to either SEQ ID NO: 6 or SEQ ID NO: 7 or variants thereof that retain functionality.

In one embodiment, the immunoconjugate comprises an antibody that is specific for the A2 domain of Tenascin (TNC-A2). In a specific embodiment, the antibody of the immunoconjugate comprises a heavy chain variable region sequence that is at least about 80%, 85%, 90%, 95%, 96%, 97%, 98%, 99% or 100% identical to a sequence selected from the group of SEQ ID NO: 5, SEQ ID NO: 71, SEQ ID NO: 73, SEQ ID NO: 75, SEQ ID NO: 77, SEQ ID NO: 79, SEQ ID NO: 81, SEQ ID NO: 83 and SEQ ID NO: 85, or variants thereof that retain functionality. In another specific embodiment, the antibody of the immunoconjugate comprises a light chain variable region sequence that is at least about 80%, 85%, 90%, 95%, 96%, 97%, 98%, 99% or 100% identical to a sequence selected from the group of SEQ ID NO: 3, SEQ ID NO: 4; SEQ ID NO: 70, SEQ ID NO: 72, SEQ ID NO: 74, SEQ ID NO: 76, SEQ ID NO: 78, SEQ ID NO: 80, SEQ ID NO: 82 and SEQ ID NO: 84, or variants thereof that retain functionality. In a more specific embodiment, the antibody of the immunoconjugate comprises a heavy chain variable region sequence that is at least about 80%, 85%, 90%, 95%, 96%, 97%, 98%, 99% or 100% identical to a sequence selected from the group of SEQ ID NO: 5, SEQ ID NO: 71, SEQ ID NO: 73, SEQ ID NO: 75, SEQ ID NO: 77, SEQ ID NO: 79, SEQ ID NO: 81, SEQ ID NO: 83 and SEQ ID NO: 85, or variants thereof that retain functionality, and a light chain variable region sequence that is at least about 80%, 85%, 90%, 95%, 96%, 97%, 98%, 99% or 100% identical to a sequence selected from the group of SEQ ID NO: 3, SEQ ID NO: 4; SEQ ID NO: 70, SEQ ID NO: 72, SEQ ID NO: 74, SEQ ID NO: 76, SEQ ID NO: 78, SEQ ID NO: 80, SEQ ID NO: 82 and SEQ ID NO: 84, or variants thereof that retain functionality.

In one embodiment, the immunoconjugate comprises an antibody that is specific for the Fibroblast Activated Protein (FAP). In a specific embodiment, the antibody of the immunoconjugate comprises a heavy chain variable region sequence that is at least about 80%, 85%, 90%, 95%, 96%, 97%, 98%, 99% or 100% identical to a sequence selected from the group consisting of SEQ ID NO: 12, SEQ ID NO: 14, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67 and SEQ ID NO: 69, or variants thereof that retain functionality. In another specific embodiment, the antibody of the immunoconjugate comprises a light chain variable region sequence that is at least about 80%, 85%, 90%, 95%, 96%, 97%, 98%, 99% or 100% identical to a sequence selected from the group consisting of: SEQ ID NO: 10, SEQ ID NO: 11, SEQ ID NO: 13, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66 and SEQ ID NO: 68, or variants thereof that retain functionality. In a more specific embodiment, the antibody of the immunoconjugate comprises a heavy chain variable region sequence that is at least about 80%, 85%, 90%, 95%, 96%, 97%, 98%, 99% or 100% identical to a sequence selected from the group consisting of SEQ ID NO: 12, SEQ ID NO: 14, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67 and SEQ ID NO: 69, or variants thereof that retain functionality, and a light chain variable region sequence that is at least about 80%, 85%, 90%, 95%, 96%, 97%, 98%, 99% or 100% identical to a sequence selected from the group consisting of: SEQ ID NO: 10, SEQ ID NO: 11, SEQ ID NO: 13, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66 and SEQ ID NO: 68, or variants thereof that retain functionality. In another specific embodiment, the antibody of the immunoconjugate comprises the heavy chain variable region sequence of SEQ ID NO: 12 and the light chain variable region sequence of SEQ ID NO: 11. In another specific embodiment, the antibody of the immunoconjugate comprises the heavy chain variable region sequence of SEQ ID NO: 17 and the light chain variable region sequence of SEQ ID NO: 16. In another specific embodiment, the antibody of the immunoconjugate comprises the heavy chain variable region sequence of SEQ ID NO: 47 and the light chain variable region sequence of SEQ ID NO: 46. In another specific embodiment, the antibody of the immunoconjugate comprises the heavy chain variable region sequence of SEQ ID NO: 63 and the light chain variable region sequence of SEQ ID NO: 62. In another specific embodiment, the antibody of the immunoconjugate comprises the heavy chain variable region sequence of SEQ ID NO: 67 and the light chain variable region sequence of SEQ ID NO: 66. In another specific embodiment, the immunoconjugate of the present invention comprises a polypeptide sequence that is at least about 80%, 85%, 90%, 95%, 96%, 97%, 98%, 99% or 100% identical to SEQ ID NO: 125 or variants thereof that retain functionality, a polypeptide sequence that is at least about 80%, 85%, 90%, 95%, 96%, 97%, 98%, 99% or 100% identical to SEQ ID NO: 126 or variants thereof that retain functionality, and a polypeptide sequence that is at least about 80%, 85%, 90%, 95%, 96%, 97%, 98%, 99% or 100% identical to SEQ ID NO: 129 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 127 or variants thereof that retain functionality, a polypeptide sequence that is at least about 80%, 85%, 90%, 95%, 96%, 97%, 98%, 99% or 100% identical to SEQ ID NO: 128 or variants thereof that retain functionality, and a polypeptide sequence that is at least about 80%, 85%, 90%, 95%, 96%, 97%, 98%, 99% or 100% identical to SEQ ID NO: 129 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 130 or variants thereof that retain functionality, a polypeptide sequence that is at least about 80%, 85%, 90%, 95%, 96%, 97%, 98%, 99% or 100% identical to SEQ ID NO: 131 or variants thereof that retain functionality, and a polypeptide sequence that is at least about 80%, 85%, 90%, 95%, 96%, 97%, 98%, 99% or 100% identical to SEQ ID NO: 132 or variants thereof that retain functionality.

In one embodiment, the immunoconjugate comprises an antibody that is specific for the Melanoma Chondroitin Sulfate Proteoglycan (MCSP). In a specific embodiment, the antibody of the immunoconjugate comprises a heavy chain variable region sequence that is at least about 80%, 85%, 90%, 95%, 96%, 97%, 98%, 99% or 100% identical to the sequence of either SEQ ID NO: 86 or SEQ ID NO: 122 or variants thereof that retain functionality. In another specific embodiment, the antibody of the immunoconjugate comprises a light chain variable region sequence that is at least about 80%, 85%, 90%, 95%, 96%, 97%, 98%, 99% or 100% identical to the sequence of either SEQ ID NO: 87 or SEQ ID NO: 123 or variants thereof that retain functionality. In a more specific embodiment, the antibody of the immunoconjugate comprises a heavy chain variable region sequence that is at least about 80%, 85%, 90%, 95%, 96%, 97%, 98%, 99% or 100% identical to the sequence of either SEQ ID NO: 86 or SEQ ID NO: 122, or variants thereof that retain functionality, and a light chain variable region sequence that is at least about 80%, 85%, 90%, 95%, 96%, 97%, 98%, 99% or 100% identical to the sequence of either SEQ ID NO: 87 or SEQ ID NO: 123, or variants thereof that retain functionality. In a more specific embodiment, the antibody of the immunoconjugate comprises a heavy chain variable region sequence that is at least about 80%, 85%, 90%, 95%, 96%, 97%, 98%, 99% or 100% identical to the sequence of SEQ ID NO: 86, and a light chain variable region sequence that is at least about 80%, 85%, 90%, 95%, 96%, 97%, 98%, 99% or 100% identical to the sequence of SEQ ID NO: 87. In another specific embodiment, the antibody of the immunoconjugate comprises a heavy chain variable region sequence that is at least about 80%, 85%, 90%, 95%, 96%, 97%, 98%, 99% or 100% identical to the sequence of SEQ ID NO: 122, and a light chain variable region sequence that is at least about 80%, 85%, 90%, 95%, 96%, 97%, 98%, 99% or 100% identical to the sequence of SEQ ID NO: 123.

In one embodiment, the immunoconjugate comprises an antibody that is specific for the Carcinoembryonic Antigen (CEA). In a specific embodiment, the antibody of the immunoconjugate comprises a heavy chain variable region sequence that is at least about 80%, 85%, 90%, 95%, 96%, 97%, 98%, 99% or 100% identical to the sequence of SEQ ID NO: 114 or a variant thereof that retains functionality. In another specific embodiment, the antibody of the immunoconjugate comprises a light chain variable region sequence that is at least about 80%, 85%, 90%, 95%, 96%, 97%, 98%, 99% or 100% identical to the sequence of SEQ ID NO: 115 or a variant thereof that retains functionality. In a more specific embodiment, the antibody of the immunoconjugate comprises a heavy chain variable region sequence that is at least about 80%, 85%, 90%, 95%, 96%, 97%, 98%, 99% or 100% identical to the sequence of SEQ ID NO: 114, or a variant thereof that retains functionality, and a light chain variable region sequence that is at least about 80%, 85%, 90%, 95%, 96%, 97%, 98%, 99% or 100% identical to the sequence of SEQ ID NO: 115, or a variant thereof that retains functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 136 or variants thereof that retain functionality, a polypeptide sequence that is at least about 80%, 85%, 90%, 95%, 96%, 97%, 98%, 99% or 100% identical to SEQ ID NO: 137 or variants thereof that retain functionality, and a polypeptide sequence that is at least about 80%, 85%, 90%, 95%, 96%, 97%, 98%, 99% or 100% identical to SEQ ID NO: 138 or variants thereof that retain functionality.

Immunoconjugates according to the invention include those that comprise sequences that are at least about 80%, 85%, 90%, 95%, 96%, 97%, 98%, 99%, or 100% identical to the sequences set forth in SEQ ID NOs 3-87, 108-132 and 136-138, including functional fragments or variants thereof. The immunoconjugates according to the invention also encompasses antibodies comprising sequences of SEQ ID NOs 3-127 with conservative amino acid substitutions. It is understood that in the sequences of SEQ ID NOs 126, 128, 131, 134 and 137, the sequence of the sequence of the mutant IL-2 described herein (see SEQ ID NO: 2) may be replaced by the sequence of human IL-2 (see SEQ ID NO: 1).

Effector Moieties of Immunoconjugates

The effector moieties for use in the invention are generally polypeptides that influence cellular activity, for example, through signal transduction pathways. Accordingly, the effector moiety of the immunoconjugate useful in the invention can be associated with receptor-mediated signaling that transmits a signal from outside the cell membrane to modulate a response within the cell. For example, an effector moiety of the immunoconjugate can be a cytokine. In a particular embodiment, the effector moiety is a single-chain effector moiety as defined herein. In one embodiment, the effector moiety, typically a single-chain effector moiety, of the immunoconjugate according to the invention is a cytokine selected from the group consisting of: IL-2, GM-CSF, IFN-α, and IL-12. In one embodiment the effector moiety is IL-2. In another embodiment, the single-chain effector moiety of the immunoconjugate is a cytokine selected from the group consisting of: IL-8, MIP-la, and TGF-β.

In one embodiment, the effector moiety, particularly a single-chain effector moiety, of the immunoconjugate is IL-2. In a specific embodiment, the IL-2 effector moiety can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In certain embodiments, the IL-2 effector moiety is a mutant IL-2 effector moiety comprising at least one amino acid mutation that reduces or abolishes the affinity of the mutant IL-2 effector moiety to the α-subunit of the IL-2 receptor (also known as CD25) but preserves the affinity of the mutant IL-2 effector moiety to the intermediate-affinity IL-2 receptor (consisting of the β- and γ-subunits of the IL-2 receptor), compared to the non-mutated IL-2 effector moiety. In one embodiment the amino acid mutations are amino acid substitutions. In a specific embodiment, the mutant IL-2 effector moiety comprises one, two or three amino acid substitutions at one, two or three position(s) selected from the positions corresponding to residue 42, 45, and 72 of human IL-2 (SEQ ID NO: 1). In a more specific embodiment, the mutant IL-2 effector moiety comprises three amino acid substitutions at the positions corresponding to residue 42, 45 and 72 of human IL-2. In an even more specific embodiment, the mutant IL-2 effector moiety is human IL-2 comprising the amino acid substitutions F42A, Y45A and L72G. In one embodiment the mutant IL-2 effector moiety additionally comprises an amino acid mutation at a position corresponding to position 3 of human IL-2, which eliminates the O-glycosylation site of IL-2. Particularly said additional amino acid mutation is an amino acid substitution replacing a threonine residue by an alanine residue. The sequence of a quadruple mutant (QM) IL-2 comprising the amino acid substitutions T3A, F42A, Y45A and L72G is shown in SEQ ID NO: 2. Suitable mutant IL-2 molecules are described in more detail in PCT publication number WO 2012/107417.

Mutant IL-2 molecules useful as effector moieties in the immunoconjugates can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. In this regard, the nucleotide sequence of native IL-2 has been described by Taniguchi et al. (Nature 302, 305-10 (1983)) and nucleic acid encoding human IL-2 is available from public depositories such as the American Type Culture Collection (Rockville Md.). An exemplary sequence of human IL-2 is shown in SEQ ID NO: 1. Substitution or insertion may involve natural as well as non-natural amino acid residues. Amino acid modification includes well known methods of chemical modification such as the addition or removal of glycosylation sites or carbohydrate attachments, and the like.

In one embodiment, the effector moiety, particularly a single-chain effector moiety, of the immunoconjugate is GM-CSF. In a specific embodiment, the GM-CSF effector moiety can elicit proliferation and/or differentiation in a granulocyte, a monocyte or a dendritic cell. In one embodiment, the effector moiety, particularly a single-chain effector moiety, of the immunoconjugate is IFN-α. In a specific embodiment, the IFN-α effector moiety can elicit one or more of the cellular responses selected from the group consisting of: inhibiting viral replication in a virus-infected cell, and upregulating the expression of major histocompatibility complex I (MHC I). In another specific embodiment, the IFN-α effector moiety can inhibit proliferation in a tumor cell. In one embodiment, the effector moiety, particularly a single-chain effector moiety, of the immunoconjugate is IL-12. In a specific embodiment, the IL-12 effector moiety can elicit one or more of the cellular responses selected from the group consisting of: proliferation in a NK cell, differentiation in a NK cell, proliferation in a T cell, and differentiation in a T cell. In one embodiment, the effector moiety, particularly a single-chain effector moiety, of the immunoconjugate is IL-8. In a specific embodiment, the IL-8 effector moiety can elicit chemotaxis in neutrophils. In one embodiment, the effector moiety, particularly a single-chain effector moiety, of the immunoconjugate, is MIP-1α. In a specific embodiment, the MIP-1α effector moiety can elicit chemotaxis in monocytes and T lymphocyte cells. In one embodiment, the effector moiety, particularly a single-chain effector moiety, of the immunoconjugate is MIP-1β. In a specific embodiment, the MIP-1β effector moiety can elicit chemotaxis in monocytes and T lymphocyte cells. In one embodiment, the effector moiety, particularly a single-chain effector moiety, of the immunoconjugate is TGF-β. In a specific embodiment, the TGF-β effector moiety can elicit one or more of the cellular responses selected from the group consisting of: chemotaxis in monocytes, chemotaxis in macrophages, upregulation of IL-1 expression in activated macrophages, and upregulation of IgA expression in activated B cells.

Antibodies for Combination with the Immunconjugates

According to the invention, antibodies for combination with the immunoconjugates are engineered to have increased effector function. Antibodies useful in the present invention for combination with the immunoconjugates include antibodies or antibody fragments that bind to a specific antigenic determinant, for example a specific tumor cell antigen, and comprise an Fc region. In certain embodiments the antibody is directed to an antigen presented on a tumor cell. Particular target antigens of the antibodies useful in the present invention include antigens expressed on the surface of tumor cells, including, but not limited to, cell surface receptors such as epidermal growth factor receptor (EGFR), insulin-like growth factor receptors (IGFR) and platelet-derived growth factor receptors (PDGFR), prostate specific membrane antigen (PSMA), carcinoembryonic antigen (CEA), dipeptidyl peptidase IV (CD26, DPPIV), FAP, HER2/neu, HER-3, E-cadherin, CD20, melanoma-associated chondroitin sulfate proteoglycan (MCSP), c-Met, CUB domain-containing protein-1 (CDCP1), and squamous cell carcinoma antigen (SCCA).

In a specific embodiment the antibody is directed to an antigen selected from the group of CD20, Epidermal Growth Factor Receptor (EGFR), HER2, HER3, Insulin-like Growth Factor 1 Receptor (IGF-1R), Carcinoembryonic Antigen (CEA), c-Met, CUB domain-containing protein-1 (CDCP1), and Melanoma-associated Chondroitin Sulfate Proteoglycan (MCSP). In one embodiment, the antibody a multispecific antibody directed to two or more antigens selected from the group of CD20, Epidermal Growth Factor Receptor (EGFR), HER2, HER3, Insulin-like Growth Factor 1 Receptor (IGF-1R), Carcinoembryonic Antigen (CEA), c-Met, CUB domain-containing protein-1 (CDCP1), and Melanoma-associated Chondroitin Sulfate Proteoglycan (MCSP).

Specific anti-CD20 antibodies useful in the present invention are humanized, IgG-class Type II anti-CD20 antibodies, having the binding specificity of the murine B-Ly1 antibody (Poppema and Visser, Biotest Bulletin 3, 131-139 (1987)). Particularly useful is a humanized, IgG-class Type II anti-CD20 antibody, comprising a) in the heavy chain variable domain a CDR1 of SEQ ID NO: 88, a CDR2 of SEQ ID NO: 89, and a CDR3 of SEQ ID NO: 90, and
  b) in the light chain variable domain a CDR1 of SEQ ID NO: 91, a CDR2 of SEQ ID NO: 92, and a CDR3 of SEQ ID NO: 93.

Particularly, the heavy chain variable region framework regions (FRs) FR1, FR2, and FR3 of said antibody are human FR sequences encoded by the VH1_10 human germ-line sequence, the heavy chain variable region FR4 of said antibody is a human FR sequence encoded by the JH4 human germ-line sequence, the light chain variable region FRs FR1, FR2, and FR3 of said antibody are human FR sequences encoded by the VK_2_40 human germ-line sequence, and the light chain variable region FR4 of said antibody is a human FR sequence encoded by the JK4 human germ-line sequence.

A more particular anti-CD20 antibody which is useful in the present invention comprises the heavy chain variable domain of SEQ ID NO: 94 and the light chain variable domain of SEQ ID NO: 95.

Such anti-CD20 antibodies are described in WO 2005/044859, which is incorporated herein by reference in its entirety.

Specific anti-EGFR antibodies useful in the present invention are humanized, IgG-class antibodies, having the binding specificity of the rat ICR62 antibody (Modjtahedi et al., Br J Cancer 67, 247-253 (1993)). Particularly useful is a humanized, IgG-class anti-EGFR antibody, comprising
 a) in the heavy chain variable domain a CDR1 of SEQ ID NO: 96, a CDR2 of SEQ ID NO: 97, and a CDR3 of SEQ ID NO: 98, and
 b) in the light chain variable domain a CDR1 of SEQ ID NO: 99, a CDR2 of SEQ ID NO: 100, and a CDR3 of SEQ ID NO: 101.

A more particular anti-EGFR antibody which is useful in the invention comprises the heavy chain variable domain of SEQ ID NO: 102 and the light chain variable domain of SEQ ID NO: 103.

Such anti-EGFR antibodies are described in WO 2006/082515 and WO 2008/017963, each of which is incorporated herein by reference in its entirety.

Other suitable humanized IgG-class anti-EGFR antibodies useful for the invention include cetuximab/IMC-C225 (Erbitux®, described in Goldstein et al., Clin Cancer Res 1, 1311-1318 (1995)), panitumumab/ABX-EGF (Vectibix®, described in Yang et al., Cancer Res 59, 1236-1243 (1999), Yang et al., Critical Reviews in Oncology/Hematology 38, 17-23 (2001)), nimotuzumab/h-R3 (TheraCim®, described in Mateo et al., Immunotechnology 3, 71-81 (1997); Crombet-Ramos et al., Int J Cancer 101, 567-575 (2002), Boland & Bebb, Expert Opin Biol Ther 9, 1199-1206 (2009)), matuzumab/EMD 72000 (described in Bier et al., Cancer Immunol Immunother 46, 167-173 (1998), Kim, Curr Opin Mol Ther 6, 96-103 (2004)), and zalutumumab/2F8 (described in Bleeker et al., J Immunol 173, 4699-4707 (2004), Lammerts van Bueren, PNAS 105, 6109-6114 (2008)).

Specific anti-IGF-1R antibodies useful in the present invention are described in WO 2005/005635 and WO 2008/077546, the entire content of each of which is incorporated herein by reference, and inhibit the binding of insulin-like growth factor-1 (IGF-1) and insulin-like growth factor-2 (IGF-2) to insulin-like growth factor-1 receptor (IGF-1R).

The anti-IGF-1R antibodies useful for the invention are preferably monoclonal antibodies and, in addition, chimeric antibodies (human constant domain), humanized antibodies and especially preferably fully human antibodies. Particular anti-IGF-1R antibodies useful for the invention bind to human IGF-1R in competition to antibody 18, i.e. they bind to the same epitope of IGF-1R as antibody 18, which is described in WO 2005/005635. Particular anti-IGF-1R antibodies are further characterized by an affinity to IGF-1R of $10^{-8}$ M ($K_D$) or less, particularly of about $10^{-9}$ to $10^{-13}$ M, and preferably show no detectable concentration-dependent inhibition of insulin binding to the insulin receptor.

Particular anti-IGF-1R antibodies useful for the invention comprise complementarity determining regions (CDRs) having the following sequences:
 a) an antibody heavy chain comprising as CDRs CDR1, CDR2 and CDR3 of SEQ ID NO: 104 or 106;
 b) an antibody light chain comprising as CDRs CDR1, CDR2 and CDR3 of SEQ ID NO: 105 or 107.

Particularly, the anti-IGF-1R antibodies useful for the invention comprise an antibody heavy chain variable domain amino acid sequence of SEQ ID NO: 104 and an antibody light chain variable domain amino acid sequence of SEQ ID NO: 105, or an antibody heavy chain variable domain amino acid sequence of SEQ ID NO: 106 and an antibody light chain variable domain amino acid sequence of SEQ ID NO: 107.

Particular anti-IGF-1R antibodies useful for the invention are obtainable from the hybridoma cell lines <IGF-1R> HUMAB-Clone 18 and <IGF-1R> HUMAB-Clone 22, which are deposited with Deutsche Sammlung von Mikroorganismen and Zellkulturen GmbH (DSMZ), Germany, under deposition numbers DSM ACC 2587 and DSM ACC 2594, respectively.

Other suitable anti-IGF-1R antibodies useful for the invention are e.g. the fully human $IgG_1$ mAb cixutumumab/IMC-A12 (described in Burtrum et al., Cancer Res 63, 8912-21 (2003); Rowinsky et al., Clin Cancer Res 13, 5549s-5555s (2007), the fully human IgGl mAb AMG-479 (described in Beltran et al., Mol Cancer Ther 8, 1095-1105 (2009); Tolcher et al., J Clin Oncol 27, 5800-7 (2009)), the humanized $IgG_1$ mAb MK-0646/h7C10 (described in Goetsch et al., Int J Cancer 113, 316-28 (2005); Broussas et al., Int J Cancer 124, 2281-93 (2009); Hidalgo et al., J Clin Oncol 26, abstract 3520 (2008); Atzori et al., J Clin Oncol 26, abstract 3519 (2008)), the humanized $IgG_1$ mAb AVE1642 (described in Descamps et al., Br J Cancer 100, 366-9 (2009); Tolcher et al., J Clin Oncol 26, abstract 3582 (2008); Moreau et al., Blood 110, abstract 1166 (2007); Maloney et al., Cancer Res 63, 5073-83 (2003)), the fully human $IgG_2$ mAb figitumumab/CP-751,871 (Cohen et al., Clin Cancer Res 11, 2063-73 (2005); Haluska et al., Clin Cancer Res 13, 5834-40 (2007); Lacy et al., J Clin Oncol 26, 3196-203 (2008); Gualberto & Karp, Clin Lung Cancer 10, 273-80 (2009), the fully human $IgG_1$ mAb SCH-717454 (described in WO 2008/076257 or Kolb et al., Pediatr Blood Cancer 50, 1190-7 (2008)), the 2.13.2. mAb (described in U.S. Pat. No. 7,037,498 (WO 2002/053596)) or the fully human $IgG_4$ mAb BIIB022.

Specific anti-CEA antibodies useful in the present invention are humanized, IgG-class antibodies, having the binding specificity of the murine PR1A3 antibody (Richman and Bodmer, Int J Cancer 39, 317-328 (1987)). Particularly useful is a humanized, IgG-class anti-CEA antibody, comprising
 a) in the heavy chain variable domain a CDR1 of SEQ ID NO: 108, a CDR2 of SEQ ID NO: 109, and a CDR3 of SEQ ID NO: 110, and
 b) in the light chain variable domain a CDR1 of SEQ ID NO: 111, a CDR2 of SEQ ID NO: 112, and a CDR3 of SEQ ID NO: 113.

A more particular anti-CEA antibody which is useful in the invention comprises the heavy chain variable domain of SEQ ID NO: 114 and the light chain variable domain of SEQ ID NO: 115.

Such anti-CEA antibodies are described in PCT publication number WO 2011/023787, which is incorporated herein by reference in its entirety.

Specific anti-HER3 antibodies that are useful in the present invention are humanized, IgG-class antibodies, such as the Mab 205.10.1, Mab 205.10.2 and Mab 205.10.3, particularly Mab 205.10.2, described in PCT publication number WO 2011/076683. Particularly useful is a humanized, IgG-class anti-HER3 antibody, comprising
 a) in the heavy chain variable domain a CDR1 of SEQ ID NO: 139, a CDR2 of SEQ ID NO: 140, and a CDR3 of SEQ ID NO: 141, and b) in the light chain variable domain a CDR1 of SEQ ID NO: 143, a CDR2 of SEQ ID NO: 144, and a CDR3 of SEQ ID NO: 145.

A more particular anti-HER3 antibody which is useful in the invention comprises the heavy chain variable domain of SEQ ID NO: 142 and the light chain variable domain of SEQ ID NO: 146.

Specific anti-CDCP1-antibodies that are useful in the present invention are humanized, IgG-class antibodies derived from the CUB4 antibody (deposition number DSM ACC 2551 (DSMZ), as described in PCT publication number WO 2011/023389.

Exemplary anti-MCSP antibodies that can be used in the present invention are described e.g. in European patent application number EP 11178393.2. Particularly useful is a humanized, IgG-class anti-MCSP antibody, comprising a) in the heavy chain variable domain a CDR1 of SEQ ID NO: 116, a CDR2 of SEQ ID NO: 117, and a CDR3 of SEQ ID NO: 118, and
b) in the light chain variable domain a CDR1 of SEQ ID NO: 119, a CDR2 of SEQ ID NO: 120, and a CDR3 of SEQ ID NO: 121.

A more particular anti-MCSP antibody which is useful in the invention comprises the heavy chain variable domain of SEQ ID NO: 122 and the light chain variable domain of SEQ ID NO: 123.

In one embodiment the antibody is a full-length antibody of the IgG-class. In a particular embodiment, the antibody is an IgG$_1$ antibody. In one embodiment, the antibody comprises a human Fc region, more particularly a human IgG Fc region, most particularly a human IgG$_1$ Fc region. The antibodies useful in the invention, such as the anti-IGF-1R, anti-EGFR and anti-CD20 antibodies described above, may comprise a human Ig gamma-1 heavy chain constant region, as set forth in SEQ ID NO: 124 (i.e. the antibodies are of human IgG$_1$ subclass).

The antibodies useful in the present invention are engineered to have increased effector function, as compared to a corresponding non-engineered antibody. In one embodiment the antibody engineered to have increased effector function has at least 2-fold, at least 10-fold or even at least 100-fold increased effector function, compared to a corresponding non-engineered antibody. The increased effector function can include, but is not limited to, one or more of the following: increased Fc receptor binding, increased C1q binding and complement dependent cytotoxicity (CDC), increased antibody-dependent cell-mediated cytotoxicity (ADCC), increased antibody-dependent cellular phagocytosis (ADCP), increased cytokine secretion, increased immune complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming.

In one embodiment the increased effector function one or more selected from the group of increased Fc receptor binding, increased CDC, increased ADCC, increased ADCP, and increased cytokine secretion. In one embodiment the increased effector function is increased binding to an activating Fc receptor. In one such embodiment the binding affinity to the activating Fc receptor is increased at least 2-fold, particularly at least 10-fold, compared to the binding affinity of a corresponding non-engineered antibody. In a specific embodiment the activating Fc receptor is selected from the group of FcγRIIIa, FcγRI, and FcγRIIa. In one embodiment the activating Fc receptor is FcγRIIIa, particularly human FcγRIIIa. In another embodiment the increased effector function is increased ADCC. In one such embodiment the ADCC is increased at least 10-fold, particularly at least 100-fold, compared to the ADCC mediated by a corresponding non-engineered antibody. In yet another embodiment the increased effector function is increased binding to an activating Fc receptor and increased ADCC.

Increased effector function can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998). Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. According to a particular embodiment, binding affinity to an activating Fc receptor is measured by surface plasmon resonance using a BIACORE® T100 machine (GE Healthcare) at 25° C. Alternatively, binding affinity of antibodies for Fc receptors may be evaluated using cell lines known to express particular Fc receptors, such as NK cells expressing FcγIIIa receptor. C1q binding assays may also be carried out to determine whether the antibody is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Increased effector function may result e.g. from glycoengineering of the Fc region or the introduction of amino acid mutations in the Fc region of the antibody. In one embodiment the antibody is engineered by introduction of one or more amino acid mutations in the Fc region. In a specific embodiment the amino acid mutations are amino acid substitutions. In an even more specific embodiment the amino acid substitutions are at positions 298, 333, and/or 334 of the Fc region (EU numbering of residues). Further suitable amino acid mutations are described e.g. in Shields et al., J Biol Chem 9(2), 6591-6604 (2001); U.S. Pat. No. 6,737,056; WO 2004/063351 and WO 2004/099249. Mutant Fc regions can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

In another embodiment the antibody is engineered by modification of the glycosylation in the Fc region. In a specific embodiment the antibody is engineered to have an increased proportion of non-fucosylated oligosaccharides in the Fc region as compared to a non-engineered antibody. An increased proportion of non-fucosylated oligosaccharides in the Fc region of an antibody results in the antibody having increased effector function, in particular increased ADCC.

In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are non-fucosylated. The non-fucosylated oligosaccharides may be of the hybrid or complex type.

In another specific embodiment the antibody is engineered to have an increased proportion of bisected oligosaccharides in the Fc region as compared to a non-engineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are bisected. The bisected oligosaccharides may be of the hybrid or complex type.

In yet another specific embodiment the antibody is engineered to have an increased proportion of bisected, non-fucosylated oligosaccharides in the Fc region, as compared to a non-engineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, at least about 35% or at least about 50%, of the N-linked oligosaccharides in the Fc region of the antibody are bisected, non-fucosylated. The bisected, non-fucosylated oligosaccharides may be of the hybrid or complex type.

The oligosaccharide structures in the antibody Fc region can be analysed by methods well known in the art, e.g. by MALDI TOF mass spectrometry as described in Umana et al., Nat Biotechnol 17, 176-180 (1999) or Ferrara et al., Biotechn Bioeng 93, 851-861 (2006). The percentage of non-fucosylated oligosaccharides is the amount of oligosaccharides lacking fucose residues, relative to all oligosaccharides attached to Asn 297 (e.g. complex, hybrid and high mannose structures) and identified in an N-glycosidase F treated sample by MALDI TOF MS. Asn 297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The percentage of bisected, or bisected non-fucosylated, oligosaccharides is determined analogously.

In one embodiment the antibody is engineered to have modified glycosylation in the Fc region, as compared to a non-engineered antibody, by producing the antibody in a host cell having altered activity of one or more glycosyltransferase. Glycosyltransferases include β(1,4)-N-acetylglucosaminyltransferase III (GnTIII), β(1,4)-galactosyltransferase (GalT), β(1,2)-N-acetylglucosaminyltransferase I (GnTI), β(1,2)-N-acetylglucosaminyltransferase II (GnTII) and α(1,6)-fucosyltransferase. In a specific embodiment the antibody is engineered to have an increased proportion of non-fucosylated oligosaccharides in the Fc region, as compared to a non-engineered antibody, by producing the antibody in a host cell having increased β(1,4)-N-acetylglucosaminyltransferase III (GnTIII) activity. In an even more specific embodiment the host cell additionally has increased α-mannosidase II (ManII) activity. The glycoengineering methodology that can be used for engineering antibodies useful for the present invention has been described in greater detail in Umana et al., Nat Biotechnol 17, 176-180 (1999); Ferrara et al., Biotechn Bioeng 93, 851-861 (2006); WO 99/54342 (U.S. Pat. No. 6,602,684; EP 1071700); WO 2004/065540 (U.S. Pat. Appl. Publ. No. 2004/0241817; EP 1587921), WO 03/011878 (U.S. Pat. Appl. Publ. No. 2003/0175884), the entire content of each of which is incorporated herein by reference in its entirety. Antibodies glycoengineered using this methodology are referred to as GLYCOM-ABs herein.

Generally, any type of cultured cell line, including the cell lines discussed herein, can be used to generate cell lines for the production of anti-TNC A2 antibodies with altered glycosylation pattern. Particular cell lines include CHO cells, BHK cells, NS0 cells, SP2/0 cells, YO myeloma cells, P3X63 mouse myeloma cells, PER cells, PER.C6 cells or hybridoma cells, and other mammalian cells. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. In a specific embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in Ferrara et al., Biotechn Bioeng 93, 851-861 (2006) and WO2004/065540, the entire contents of which are expressly incorporated herein by reference.

The host cells which contain the coding sequence of an antibody useful for the invention and/or the coding sequence of polypeptides having glycosyltransferase activity, and which express the biologically active gene products may be identified e.g. by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g. by employing a lectin which binds to biosynthetis products of GnTIII or ManII, respectively. An example for such a lectin is the $E_4$-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased effector function, e.g. increased Fc receptor binding, mediated by antibodies produced by the cells engineered with the polypeptide having GnTIII or ManII activity may be used.

In another embodiment the antibody is engineered to have an increased proportion of non-fucosylated oligosaccharides in the Fc region, as compared to a non-engineered antibody, by producing the antibody in a host cell having decreased α(1,6)-fucosyltransferase activity. A host cell having decreased α(1,6)-fucosyltransferase activity may be a cell in which the α(1,6)-fucosyltransferase gene has been disrupted or otherwise deactivated, e.g. knocked out (see Yamane-Ohnuki et al., Biotech Bioeng 87, 614 (2004); Kanda et al., Biotechnol Bioeng, 94(4), 680-688 (2006); Niwa et al., J Immunol Methods 306, 151-160 (2006)).

Other examples of cell lines capable of producing defucosylated antibodies include Lec13 CHO cells deficient in protein fucosylation (Ripka et al., Arch Biochem Biophys 249, 533-545 (1986); US Pat. Appl. No. US 2003/0157108; and WO 2004/056312, especially at Example 11). The antibodies useful in the present invention can alternatively be glycoengineered to have reduced fucose residues in the Fc region according to the techniques disclosed in EP 1 176 195 A1, WO 03/084570, WO 03/085119 and U.S. Pat. Appl. Pub. Nos. 2003/0115614, 2004/093621, 2004/110282, 2004/110704, 2004/132140, U.S. Pat. No. 6,946,292 (Kyowa), e.g. by reducing or abolishing the activity of a GDP-fucose transporter protein in the host cells used for antibody production.

Glycoengineered antibodies useful in the invention may also be produced in expression systems that produce modified glycoproteins, such as those taught in WO 03/056914 (GlycoFi, Inc.) or in WO 2004/057002 and WO 2004/024927 (Greenovation).

Recombinant Methods

Methods to produce antibodies and immunoconjugates useful in the invention are well known in the art, and described for example in WO 2012/146628, WO 2005/044859, WO 2006/082515, WO 2008/017963, WO 2005/005635, WO 2008/077546, WO 2011/023787, WO 2011/076683, WO 2011/023389 and WO 2006/100582. Established methods to produce polyclonal antibodies and monoclonal antibodies are also described, e.g., in Harlow and Lane, "Antibodies, a laboratory manual", Cold Spring Harbor Laboratory, 1988.

Non-naturally occurring antibodies or fragments thereof can be constructed using solid phase-peptide synthesis, can be produced recombinantly (e.g. as described in U.S. Pat. No. 4,816,567) or can be obtained, for example, by screening combinatorial libraries comprising variable heavy chains and variable light chains (see e.g. U.S. Pat. No. 5,969,108 to McCafferty). For recombinant production of immunoconjugates and antibodies useful in the invention, one or more polynucleotide(s) encoding said immunoconjugate or antibody is isolated and inserted into one or more vectors for further cloning and/or expression in a host cell. Such polynucleotides may be readily isolated and sequenced using conventional procedures. Methods which are well known to those skilled in the art can be used to construct expression vectors containing the coding sequence of an antibody or immunoconjugate along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989).

Immunoconjugates useful in the invention may be expressed from a single polynucleotide that encodes the entire immunoconjugate or from multiple (e.g., two or more) polynucleotides that are co-expressed. Polypeptides encoded by polynucleotides that are co-expressed may associate through, e.g., disulfide bonds or other means to form a functional immunoconjugate. For example, the light chain portion of an antibody may be encoded by a separate polynucleotide from the portion of the immunoconjugate comprising the heavy chain portion of the antibody and the effector moiety. When coexpressed, the heavy chain polypeptides will associate with the light chain polypeptides to form the antibody.

Host cells suitable for replicating and for supporting expression of recombinant proteins are well known in the art. Such cells may be transfected or transduced as appropriate with the particular expression vector and large quantities of vector containing cells can be grown for seeding large scale fermenters to obtain sufficient quantities of the proteins, e.g. for clinical applications. Suitable host cells include prokaryotic microorganisms, such as E. coli, or various eukaryotic cells, such as Chinese hamster ovary cells (CHO), insect cells, or the like. For example, recombinant proteins may be produced in bacteria in particular when glycosylation is not needed. After expression, the protein may be isolated from the bacterial cell paste in a soluble fraction and can be further purified. In addition to prokaryotes, eukaryotic microbes such as filamentous fungi or yeast are suitable cloning or expression hosts for protein-encoding vectors, including fungi and yeast strains whose glycosylation pathways have been "humanized," resulting in the production of a protein with a partially or fully human glycosylation pattern. See Gerngross, Nat Biotech 22, 1409-1414 (2004), and Li et al., Nat Biotech 24, 210-215 (2006). Suitable host cells for the expression of (glycosylated) proteins are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177; 6,040,498; 6,420,548; 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney (HEK) line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, particularly a mammalian cell, e.g. a Chinese Hamster Ovary (CHO) cell, a human embryonic kidney (HEK) 293 cell, or lymphoid cell (e.g., Y0, NS0, Sp20 cell).

If the antibody and immunoconjugate are intended for human use, chimeric forms of antibodies may be used wherein the antibody constant regions are from a human. A humanized or fully human form of the antibody can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antibodies useful in the present invention are engineered to have enhanced binding affinity according to, for example, the methods disclosed in U.S. Pat. Appl. Publ. No. 2004/0132066, the entire contents of which are hereby incorporated by reference. The ability of the antibodies useful in the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)).

Antibodies and immunoconjugates prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art.

Pharmaceutical Compositions

In another aspect the invention provides a pharmaceutical composition comprising (a) an immunoconjugate comprising a first antibody engineered to have reduced effector function and an effector moiety, and (b) a second antibody engineered to have increased effector function, in a pharmaceutically acceptable carrier. These pharmaceutical compositions may be used, e.g., in any of the therapeutic methods described below.

Pharmaceutical compositions of an immunoconjugate and an antibody having increased effector function as described herein are prepared by mixing such immunoconjugate and antibody having the desired degree of purity with one or more optional pharmaceutically acceptable carriers (Remington's Pharmaceutical Sciences 18th edition, Mack Printing Company (1990)), in the form of lyophilized formulations or aqueous solutions. Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

The pharmaceutical composition herein may also contain additional active ingredients as necessary for the particular indication being treated, particularly those with complementary activities that do not adversely affect each other. For example, if the disease to be treated is cancer, it may be desirable to further provide one or more anti-cancer agents, e.g. a chemotherapeutic agent, an inhibitor of tumor cell proliferation, or an activator of tumor cell apoptosis. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, Mack Printing Company (1990).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The compositions to be used for in vivo administration are generally sterile. Sterility may be readily accomplished, e.g., by filtration through sterile filtration membranes.

Methods of Treatment

The combination provided herein of (a) an immunoconjugate comprising a first antibody engineered to have reduced effector function and an effector moiety, and (b) a second antibody engineered to have increased effector function, may be used in therapeutic methods.

In one aspect, a combination of (a) an immunoconjugate comprising a first antibody engineered to have reduced effector function and an effector moiety, and (b) a second antibody engineered to have increased effector function, for use as a medicament is provided. In further aspects, a combination of (a) an immunoconjugate comprising a first antibody engineered to have reduced effector function and an effector moiety, and (b) a second antibody engineered to have increased effector function, for use in treating a disease is provided. In certain embodiments, a combination of (a) an immunoconjugate comprising a first antibody engineered to have reduced effector function and an effector moiety, and (b) a second antibody engineered to have increased effector function, for use in a method of treatment is provided. In certain embodiments, the invention provides a combination of (a) an immunoconjugate comprising a first antibody engineered to have reduced effector function and an effector moiety, and (b) a second antibody engineered to have increased effector function, for use in a method of treating an individual having a disease comprising administering to the individual a therapeutically effective amount of the combination. In one such embodiment, the method further comprises administering to the individual a therapeutically effective amount of at least one additional therapeutic agent, e.g., as described below. In further embodiments, the invention provides a combination of (a) an immunoconjugate comprising a first antibody engineered to have reduced effector function and an effector moiety, and (b) a second antibody engineered to have increased effector function, for use in stimulating effector cell function. In certain embodiments, the invention provides a combination of (a) an immunoconjugate comprising a first antibody engineered to have reduced effector function and an effector moiety, and (b) a second antibody engineered to have increased effector function, for use in a method of stimulating effector cell function in an individual comprising administering to the individual an effective amount of the combination to stimulate effector cell function. An "individual" according to any of the above embodiments is a mammal, particularly a human. A "disease" according to any of the above embodiments is a disease treatable by stimulation of effector cell function. In certain embodiments the disease is a cell proliferation disorder, particularly cancer.

In a further aspect, the invention provides for the use of a combination of (a) an immunoconjugate comprising a first antibody engineered to have reduced effector function and an effector moiety, and (b) a second antibody engineered to have increased effector function, in the manufacture or preparation of a medicament. In one embodiment, the medicament is for treatment of a disease. In a further embodiment, the medicament is for use in a method of treating a disease comprising administering to an individual having the disease a therapeutically effective amount of the medicament. In one such embodiment, the method further comprises administering to the individual a therapeutically effective amount of at least one additional therapeutic agent, e.g., as described below. In a further embodiment, the medicament is for stimulating effector cell function. In a further embodiment, the medicament is for use in a method of stimulating effector cell function in an individual comprising administering to the individual an amount of the medicament effective to stimulate effector cell function. An "individual" according to any of the above embodiments is a mammal, particularly a human. A "disease" according to any of the above embodiments is a disease treatable by stimulation of effector cell function. In certain embodiments the disease is a cell proliferation disorder, particularly cancer.

In a further aspect, the invention provides a method for treating a disease. In one embodiment, the method comprises administering to an individual having such disease a therapeutically effective amount of a combination of (a) an immunoconjugate comprising a first antibody engineered to have reduced effector function and an effector moiety, and (b) a second antibody engineered to have increased effector function. In one such embodiment, the method further comprises administering to the individual a therapeutically effective amount of at least one additional therapeutic agent, as described below. An "individual" according to any of the above embodiments is a mammal, particularly a human. A "disease" according to any of the above embodiments is a disease treatable by stimulation of effector cell function. In certain embodiments the disease is a cell proliferation disorder, particularly cancer.

In a further aspect, the invention provides a method for stimulating effector cell function in an individual. In one embodiment, the method comprises administering to the individual an effective amount of a combination of (a) an immunoconjugate comprising a first antibody engineered to have reduced effector function and an effector moiety, and (b) a second antibody engineered to have increased effector function, to stimulate effector cell function. In one embodiment, an "individual" is a mammal, particularly a human.

In a further aspect, the invention provides pharmaceutical composition comprising any of the combinations of (a) an immunoconjugate comprising a first antibody engineered to have reduced effector function and an effector moiety, and (b) a second antibody engineered to have increased effector function provided herein, e.g., for use in any of the above therapeutic methods. In one embodiment, a pharmaceutical composition comprises a combination provided herein, of (a) an immunoconjugate comprising a first antibody engineered to have reduced effector function and an effector moiety and (b) a second antibody engineered to have increased effector function, and a pharmaceutically acceptable carrier. In another embodiment, a pharmaceutical composition comprises any of the combinations provided herein and at least one additional therapeutic agent, e.g., as described below.

According to any of the above embodiments, the disease is a disorder treatable by stimulation of effector cell function. Combinations of the invention are useful in treating disease states where stimulation of the immune system of the host is beneficial, in particular conditions where an enhanced cellular immune response is desirable. These may include disease states where the host immune response is insufficient or deficient. Disease states for which the combinations of the invention can be administered comprise, for example, a tumor or infection where a cellular immune response would be a critical mechanism for specific immunity. Specific disease states for which the combinations of the present invention can be employed include cancer, specifically renal cell carcinoma or melanoma; immune deficiency, specifically in HIV-positive patients, immunosuppressed patients, chronic infection and the like. In certain embodiments the disease is a cell proliferation disorder. In a particular embodiment the disease is cancer, specifically a cancer selected from the group of lung cancer, colorectal cancer, renal cancer, prostate cancer, breast cancer, head and neck cancer, ovarian cancer, brain cancer, lymphoma, leukemia, skin cancer.

Combinations of the invention can be used either alone or together with other agents in a therapy. For instance, a combination of the invention may be co-administered with at least one additional therapeutic agent. In certain embodiments, an additional therapeutic agent is an anti-cancer agent, e.g. a chemotherapeutic agent, an inhibitor of tumor cell proliferation, or an activator of tumor cell apoptosis.

Combination therapies as provided herein encompass administration of the antibody and the immunoconjugate together (where the two or more therapeutic agents are included in the same or separate formulations), and separately, in which case, administration of the antibody can occur prior to, simultaneously, and/or following, administration of the immunoconjugate, additional therapeutic agent and/or adjuvant. Combinations of the invention can also be combined with radiation therapy.

A combination of the invention (and any additional therapeutic agent) can be administered by any suitable route, including parenteral, intrapulmonary, and intranasal, and, if desired for local treatment, intralesional administration. Parenteral infusions include intramuscular, intravenous, intraarterial, intraperitoneal, or subcutaneous administration. The antibody and the immunoconjugate may be administered by the same or by different routes. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Combinations of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agents, the method of administration, the scheduling of administration, and other factors known to medical practitioners. The combination need not be, but is optionally formulated with one or more agents currently used to prevent or treat the disorder in question. The effective amount of such other agents depends on the amount of antibody and immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody and immunoconjugate (when used in the combinations of the invention, optionally together with one or more other additional therapeutic agents) will depend on the type of disease to be treated, the type of antibody and immunoconjugate, the severity and course of the disease, whether the combination is administered for preventive or therapeutic purposes, previous therapy, the patient's clinical history and response to the antibody and/or immunoconjugate, and the discretion of the attending physician. The antibody and the immunoconjugate are suitably administered to the patient at one time or over a series of treatments.

Depending on the type and severity of the disease, about 1 mg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. The same considerations with respect to dosage apply to the immunconjugate to be used in the combinations according to the invention. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises one or more container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody to be used in the combinations of the invention. Another active agent is the immunoconjugate to be used in the combinations of the invention, which may be in the same composition and container like the antibody, or may be provided in a different composition and container. The label or package insert indicates that the composition is used for treating the condition of choice.

In one aspect the invention provides a kit intended for the treatment of a disease, comprising in the same or in separate containers (a) an immunoconjugate comprising a first antibody engineered to have reduced effector function and an effector moiety, and (b) a second antibody engineered to have increased effector function, and optionally further comprising (c) a package insert comprising printed instructions directing the use of the combined treatment as a method for treating the disease. Moreover, the kit may comprise (a) a first container with a composition contained therein, wherein the composition comprises an antibody engineered to have increased effector function; (b) a second container with a composition contained therein, wherein the composition comprises an immunoconjugate comprising an antibody engineered to have reduced effector function and an effector moiety; and optionally (c) a third container with a composition contained therein, wherein the composition comprises a further cytotoxic or otherwise therapeutic agent. The kit in this embodiment of the invention may further comprise a package insert indicating that the compositions can be used to treat a particular condition. Alternatively, or additionally, the kit may further comprise a third (or fourth) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

General Methods

Glycoengineereing of the Fc region of an antibody leads to increased binding affinity to human FcγRIII receptors, which in turn translates into enhanced ADCC induction and anti-tumor efficacy. Human FcγRIII receptors are expressed on macrophages, neutrophils, and natural killer (NK), dendritic and γδ T cells. In the mouse, the most widely utilized species for preclinical efficacy testing, murine FcγRIV, the murine homologue of human FcγRIIIa, is present on marcophages and neutrophils but not on NK cells. Therefore, not the full extent of any expected improved efficacy with glycoengineered antibodies is reflected in those models. We have generated a mouse transgenic for human FcγRIIIa (CD16a), exhibiting stable human CD16a expression on murine NK cells in blood, lymphoid tissues and tumors. Moreover, the expression level of human CD16a on unstimulated NK cells in the blood of these transgenic mice mirrors that found in human. We also showed that a down-regulation of human FcγRIIIa on the tumor-associated NK cells after antibody therapy correlates with antitumoral activity. Finally, we showed significantly improved efficacy of glycoengineered antibody treatment in tumor models using this new mouse strain as compared to their human CD16-negative littermates.

Example 1

FaDu Head and Neck Carcinoma Xenograft Model

The FAP-targeted 28H1 IgG-IL2 and untargeted DP47GS IgG-IL2 immunoconjugates comprising the IL-2 quadruple mutant (qm) (SEQ ID NOs: 125, 126, 129, and SEQ ID NOs: 133-135, respectively) and the anti-EGFR GLYCOMAB (SEQ ID NOs: 102 and 103) were tested in the human head and neck carcinoma cell line FaDu, intralingually injected into SCID mice. This tumor model was shown by IHC on fresh frozen tissue to be positive for FAP. FaDu cells were originally obtained from ATCC (American Type Culture Collection) and after expansion deposited in the Glycart internal cell bank. The tumor cell line was routinely cultured in DMEM containing 10% FCS (Gibco), at 37° C. in a water-saturated atmosphere at 5% $CO_2$. In vitro passage 9 was used for intralingual injection, at a viability of 95.8%. Twenty μl cell suspension ($2\times10^5$ FaDu cells in AimV medium (Gibco)) was injected intralingually. Female SCID mice (Taconics, Denmark), aged 8-9 weeks at the start of the experiment were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to new environment and for observation. Continuous health monitoring was carried out on a regular basis. Mice were injected intralingually on study day 0 with $2\times10^5$ FaDu cells, randomized and weighed. One week after the tumor cell injection, mice were injected i.v. with the 28H1 IgG-IL2 qm immunoconjugate, the DP47GS IgG-IL2 qm immunoconjugate, the anti-EGFR GLYCOMAB, the combination of the 28H1 IgG-IL2 qm immunoconjugate and the anti-EGFR GLYCOMAB, or the combination of the DP47GS IgG-IL2 qm immunoconjugate and the anti-EGFR GLYCOMAB once weekly for four weeks. All mice were injected i.v. with 200 μl of the appropriate solution. Doses are specified in Table 2. The mice in the vehicle group were injected with PBS and the treatment groups with the 28H1 IgG-IL2 qm immunoconjugate, the DP47GS IgG-IL2 qm immunoconjugate, the anti-EGFR GLYCOMAB, the combination of the 28H1 IgG-IL2 qm immunoconjugate and the anti-EGFR GLYCOMAB, or the combination of the DP47GS IgG-IL2 qm immunoconjugate and the anti-EGFR GLYCOMAB. To obtain the proper amount of immunoconjugate per 200 the stock solutions were diluted with PBS when necessary. FIG. 1A shows that only the combination of the FAP-targeted 28H1 IgG-IL2 qm immunoconjugate and the anti-EGFR GLYCOMAB mediated superior efficacy in terms of enhanced median survival compared to the 28H1 IgG-IL2 qm immunoconjugate or the anti-EGFR GLYCOMAB alone. In contrast thereto, the combination of the untargeted DP47GS IgG-IL2 qm and the anti-EGFR GLYCOMAB did not show superiority over the single agent administration (FIG. 1B).

TABLE 2

| Compound | Dose/mouse | Formulation buffer | Concentration (mg/mL) |
| --- | --- | --- | --- |
| Anti-EGFR GLYCOMAB | 625 μg | 20 mM His/HisCl 240 mM trehalose 0.02% polysorbate 80 10 mM methionine pH 5.5 | 26.65 (=stock solution) |
| FAP 28H1 IgG-IL2 qm | 50 μg | 20 mM histidine, 140 mM NaCl, pH 6.0 | 3.46 (=stock solution) |
| untargeted DP47GS IgG-IL2 qm | 50 μg | 20 mM histidine, 140 mM NaCl, pH 6.0 | 5.87 (=stock solution) |

Example 2

In Vitro Boosting of NK Cell Killing Capacity by IL-2 Immunoconjugates

To determine the effect of immunoconjugates on NK cells, we assessed the killing of tumor cells upon treatment with the immunoconjugates, particularly immunoconjugates comprising IL-2 as effector moiety. For this purpose, peripheral blood mononuclear cells (PBMCs) were isolated according to standard procedures, using Histopaque-1077 (Sigma Diagnostics Inc., St. Louis, Mo., USA). In brief, venous blood was taken with heparinized syringes from healthy volunteers. The blood was diluted 2:1 with PBS not containing calcium or magnesium and layered on Histopaque-1077. The gradient was centrifuged at 450×g for 30 min at room temperature (RT) without brake. The interphase containing the PBMCs was collected and washed with PBS in total three times (350×g followed by 300×g for 10 min at RT).

The isolated PBMCs were incubated with IL-2 (Proleukin) or IL-2 immunoconjugates, added to the cell supernatant, for 45 h. Subsequently, the PBMCs were recovered and used for anti-EGFR GLYCOMAB-mediated ADCC of A549 cells at an E:T of 10:1, for 4 h. Target cell killing was detected by measuring LDH release into the cell supernatants (Roche Cytotoxicity Detection Kit LDH). FIG. 2 shows the overall A549 tumor cell killing by PBMCs, pre-treated or not with 0.57 nM (A) or 5.7 nM (B) FAP-targeted 28H1 IgG-IL2 qm immunoconjugate or IL-2 (Proleukin), in the presence of different concentrations of anti-EGFR GLYCOMAB. The graphs show that immunoconjugate pre-treatment of effector cells results in a greater increase in target cell killing with increasing concentrations of GLYCOMAB, as compared to untreated effector cells.

Example 3

LS174T Colorectal Xenograft Model

The CEA-targeted CH1A1A IgG-IL2 qm immunoconjugate (SEQ ID NOs: 136-138), the anti-EGFR GLYCOMAB (SEQ ID NOs: 102 and 103) and cetuximab were tested in the human colorectal LS174T cell line, intrasplenically injected into SCID-human FcγRIII transgenic mice. This tumor model was shown by IHC on fresh frozen tissue to be positive for CEA. LS174T cells (human colon carcinoma cells) were originally obtained from ECACC (European Collection of Cell Culture) and after expansion deposited in the Glycart internal cell bank. LS174T were cultured in MEM Eagle's medium containing 10% FCS (PAA Laboratories, Austria), 1% GLUTAMAX (L-alanyl-L-glutamine) and 1% MEM Non-Essential Amino Acids (Sigma). The cells were cultured at 37° C. in a water-saturated atmosphere at 5% $CO_2$. In vitro passage 19 or 23 was used for intrasplenic injection, at a viability of 99%. A small incision was made at the left abdominal site of anesthetized SCID FcγRIII transgenic mice. Thirty microliters cell suspension ($2\times10^6$ LS174T cells in AimV medium) was injected through the abdominal wall just under the capsule of the spleen. Skin wounds were closed using clamps or resolvable sutures. Female SCID FcγRIII transgenic mice; aged 8-9 weeks at the start of the experiment (purchased from Taconics, Denmark) were maintained under specific-pathogen-free conditions with daily cycles of 12 h light/12 h darkness according to committed guidelines (GV-Solas; Felasa; TierschG). The experimental study protocol was reviewed and approved by local government (P 2008016, P2011/128). After arrival, animals were maintained for one week to get accustomed to the new environment and for observation. Continuous health monitoring was carried out on a regular basis. Mice were injected intrasplenically on study day 0 with $2\times10^6$ LS174T cells, randomized and weighed. One week after the tumor cell injection mice were injected i.v. with the CH1A1A IgG-IL2 qm immunoconjugate, the anti-EGFR GLYCOMAB, cetuximab, the combination of the CH1A1A IgG-IL2 qm immunoconjugate and the anti-EGFR GLYCOMAB or the combination of the CH1A1A IgG-IL2 qm immunoconjugate and cetuximab once weekly for three weeks. All mice were injected i.v. with 200 µl of the appropriate solution. Doses are specified in Table 3. The mice in the vehicle group were injected with PBS and the treatment groups with the CH1A1A IgG-IL2 qm immunoconjugate or the anti-EGFR GLYCOMAB, cetuximab, the combination of the CH1A1A IgG-IL2 qm immunoconjugate and the anti-EGFR GLYCOMAB, or the combination of the CH1A1A IgG-IL2 qm immunoconjugate and cetuximab. To obtain the proper amount of immunoconjugate per 200 µl the stock solutions were diluted with PBS when necessary. FIG. 3 and Tables 3A and 3B show that the combination of the CH1A1A IgG-IL2 qm immunoconjugate and the anti-EGFR GLYCOMAB mediated superior efficacy in terms of enhanced median and overall survival compared to the CH1A1A IgG-IL2 qm immunoconjugate alone, the anti-EGFR GLYCOMAB alone, cetuximab alone, or the combination of the CH1A1A IgG-IL2 qm immunoconjugate and cetuximab.

TABLE 3

| Compound | Dose/mouse | Formulation buffer | Concentration (mg/mL) |
| --- | --- | --- | --- |
| Anti-EGFR GLYCOMAB | 500 µg | 20 mM His/HisCl 240 mM trehalose 0.02% TWEEN (polysorbate) 20 pH 6.0 | 25.3 (=stock solution) |
| CH1A1A IgG-IL2 qm | 40 µg (FIG. 3A) or 20 µg (FIG 3B) | 20 mM histidine, 140 mM NaCl, pH 6.0 | 4.27 (=stock solution) |
| Cetuximab | 500 µg | 10 mM Na-citrate, NaCl, glycine, TWEEN (polysorbate) 80, pH 5.5 | 4.36 (=stock solution) |

TABLE 3A

Summary of survival data corresponding to FIG. 3A.

| Treatment | Median survival (days) | Overall survival |
| --- | --- | --- |
| Vehicle | 24 | 0/8 |
| CH1A1A IgG-IL2 qm | 33 | 0/8 |
| Anti-EGFR GLYCOMAB | 40 | 0/8 |
| CH1A1A IgG-IL2 qm + anti-EGFR GLYCOMAB | 141 | 3/8 |

TABLE 3B

Summary of survival data corresponding to FIG. 3B.

| Treatment | Median survival (days) | Overall survival |
| --- | --- | --- |
| Vehicle | 29 | 0/8 |
| CH1A1A IgG-IL2 qm | 35 | 0/8 |
| Cetuximab | 39 | 0/8 |
| CH1A1A IgG-IL2 qm + Cetuximab | 53 (ongoing) | 2/8 (ongoing) |

Example 4

A549 Lung Xenograft Model

The CEA-targeted CH1A1A IgG-IL2 qm immunoconjugate (SEQ ID NOs: 136-138), the anti-EGFR GLYCOMAB (SEQ ID NOs: 102 and 103) and cetuximab were tested in the human NSCLC cell line A549, injected i.v. into SCID-human FcγRIII transgenic mice.

The A549 non-small cell lung carcinoma cells were originally obtained from ATCC (CCL-185) and after expansion deposited in the Roche-Glycart internal cell bank. The tumor cell line was routinely cultured in DMEM containing 10% FCS (Gibco) at 37° C. in a water-saturated atmosphere at 5% $CO_2$. Passage 8 was used for transplantation, at a viability of 97-98%. $5 \times 10^6$ cells per animal were injected i.v. into the tail vein in 200 µl of Aim V cell culture medium (Gibco). Female SCID-FcγRIII mice (Roche-Glycart; Switzerland), aged 8-9 weeks at the start of the experiment (bred at Charles Rivers, Lyon, France) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Mice were injected i.v. on study day 0 with $5 \times 10^6$ A549 cells, randomized and weighed. One week (FIG. 4A) or two weeks (FIG. 4B) after the tumor cell injection, mice were injected i.v. with the CH1A1A IgG-IL2 qm immunoconjugate, the anti-EGFR GLYCOMAB, cetuximab, the combination of the CH1A1A IgG-IL2 qm immunoconjugate and the anti-EGFR GLYCOMAB, or the combination of the CH1A1A IgG-IL2 qm immunoconjugate and cetuximab once weekly for three weeks. All mice were injected i.v. with 200 µl of the appropriate solution. Doses are specified in Table 4. The mice in the vehicle group were injected with PBS and the treatment group with the CH1A1A IgG-IL2 qm immunoconjugate, the anti-EGFR GLYCOMAB, the combination of the CH1A1A IgG-IL2 qm immunoconjugate and the anti-EGFR GLYCOMAB, or the combination of the CH1A1A IgG-IL2 qm immunoconjugate and cetuximab. To obtain the proper amount of immunoconjugate per 200 the stock solutions were diluted with PBS when necessary. FIG. 4 and Tables 4A and 4B show that the combination of the CH1A1A IgG-IL2 qm immunoconjugate and the anti-EGFR GLYCOMAB mediates superior efficacy in terms of enhanced median and overall survival compared to the respective immunoconjugate, the anti-EGFR GLYCOMAB or cetuximab alone, as well as the combination of the CH1A1A IgG-IL2 qm immunoconjugate and cetuximab.

TABLE 4

| Compound | Dose | Formulation buffer | Concentration (mg/mL) |
|---|---|---|---|
| CH1A1A IgG-IL2 qm | 20 µg | 20 mM histidine, 140 mM NaCl, pH 6.0 | 4.27 (=stock solution) |
| Anti-EGFR GLYCOMAB | 500 µg | 20 mM His/HisCl, 240 mM trehalose, 0.02% TWEEN (polysorbate) 20, pH 6.0 | 25.3 (=stock solution) |
| Cetuximab | 500 µg | 10 mM Na-citrate, NaCl, glycine, TWEEN (polysorbate) 80, pH 5.5 | 4.36 (=stock solution) |

TABLE 4A

Summary of survival data corresponding to FIG. 4A.

| Treatment | Median survival (days) | Overall survival |
|---|---|---|
| Vehicle | 53 | 0/9 |
| CH1A1A IgG-IL2 qm | 103 | 0/9 |
| Anti-EGFR GLYCOMAB | 211 | 2/9 |
| CH1A1A IgG-IL2 qm + anti-EGFR GLYCOMAB | not reached | 9/9 |

TABLE 4B

Summary of survival data corresponding to FIG. 4B.

| Treatment | Median survival (days) | Overall survival |
|---|---|---|
| Vehicle | 49 | 0/10 |
| CH1A1A IgG-IL2 qm | 64 | 0/10 |
| Cetuximab | 68 | 0/10 |
| CH1A1A IgG-IL2 qm + Cetuximab | 91 | 0/10 |

Example 5

LS174T Colorectal Xenograft Model

The CEA-targeted CH1A1A IgG-IL2 qm immunoconjugate (SEQ ID NOs: 136-138) and the anti-Her3 GLYCOMAB (SEQ ID NOs: 142 and 146) were tested in the human colorectal LS174T cell line, intrasplenically injected into SCID-human FcγRIII transgenic mice.

LS174T cells (human colon carcinoma cells) were originally obtained from ECACC (European Collection of Cell Culture) and after expansion deposited in the Roche-Glycart internal cell bank. LS174T were cultured in MEM Eagle's medium containing 10% FCS (PAA Laboratories, Austria), 1% GLUTAMAX (L-alanyl-L-glutamine) and 1% MEM Non-Essential Amino Acids (Sigma). The cells were cultured at 37° C. in a water-saturated atmosphere at 5% $CO_2$. In vitro passage 21 was used for intrasplenic injection, at a viability of 97.9%. A small incision was made at the left abdominal site of anesthetized SCID-human FcγRIII transgenic mice. Thirty microliters ($2 \times 10^6$ LS174T cells in AimV medium) cell suspension was injected through the abdominal wall just under the capsule of the spleen. Skin wounds were closed using resolvable sutures.

Female SCID-human FcγRIII transgenic mice; aged 8-9 weeks at the start of the experiment (Roche-Glycart, Switzerland) were maintained under specific-pathogen-free conditions with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Mice were injected intrasplenically on study day 0 with $2 \times 10^6$ LS174T cells, randomized and weighed. One week after the tumor cell injection mice were injected i.v. with the CH1A1A IgG-IL2 qm immunoconjugate, the anti-Her3 GLYCOMAB or the combination of the CH1A1A IgG-IL2 qm immunoconjugate and the anti-Her3 GLYCOMAB once weekly for three weeks.

All mice were injected i.v. with 200 µl of the appropriate solution. Doses are specified in Table 5. The mice in the vehicle group were injected with PBS and the treatment groups with the CH1A1A IgG-IL2 qm immunoconjugate, the anti-Her3 GLYCOMAB or the combination of the CH1A1A IgG-IL2 qm immunoconjugate and the anti-Her3 GLYCOMAB. To obtain the proper amount of immunoconjugate per 200 µl, the stock solutions were diluted with PBS when necessary. FIG. 5 and Table 5A show that the combination of the CH1A1A IgG-IL2 qm immunoconjugate and the anti-Her3 GLYCOMAB mediated superior efficacy in terms of enhanced median survival compared to the CH1A1A IgG-IL2 qm immunoconjugate or the anti-Her3 GLYCOMAB alone.

TABLE 5

| Compound | Dose | Formulation buffer | Concentration (mg/mL) |
|---|---|---|---|
| Anti-Her3 GLYCOMAB | 200 µg | | 10.0 (=stock solution) |
| CH1A1A IgG-IL2 qm | 20 µg | 20 mM histidine, 140 mM NaCl, pH 6.0 | 13.60 (=stock solution) |

TABLE 5A

Summary of survival data corresponding to FIG. 5.

| Treatment | Median survival (days) | Overall survival |
|---|---|---|
| Vehicle | 24 | 0/10 |
| CH1A1A IgG-IL2 qm | 25 | 0/10 |
| Anti-Her3 GLYCOMAB | 27 | 0/10 |
| CH1A1A IgG-IL2 qm + anti-Her3 GLYCOMAB | 34 | 0/10 |

Example 6

ACHN Renal Carcinoma Xenograft Model

The FAP-targeted 28H1 IgG-IL2 immunoconjugate comprising the IL-2 quadruple mutant (qm) (SEQ ID NOs: 125, 126 and 129) and the anti-EGFR GLYCOMAB (SEQ ID NOs: 102 and 103) were tested in the human renal cell line ACHN, intrarenally injected into SCID-human FcγRIII transgenic mice.

ACHN cells (human renal adenocarcinoma cells) were originally obtained from ATCC (American Type Culture Collection) and after expansion deposited in the Roche-Glycart internal cell bank. ACHN were cultured in DMEM containing 10% FCS. The cells were cultured at 37° C. in a water-saturated atmosphere at 5% $CO_2$. In vitro passage 22 was used for intrarenal injection, at a viability of 96.4%. A small incision (2 cm) was made at the right flank and peritoneal wall of anesthetized SCID-human FcγRIII transgenic mice. Fifty µl (1×10⁶ ACHN cells in AimV medium) cell suspension was injected 2 mm subcapsularly in the kidney. Skin wounds and peritoneal wall were closed using resolvable sutures.

Female SCID-human FcγRIII transgenic mice; aged 8-9 weeks at the start of the experiment (Roche-Glycart, Switzerland) were maintained under specific-pathogen-free conditions with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to new environment and for observation. Continuous health monitoring was carried out on a regular basis.

Mice were injected intrarenally on study day 0 with 1×10⁶ ACHN cells, randomized and weighed. One week after the tumor cell injection, mice were injected i.v. with vehicle, anti-EGFR-GLYCOMAB, the combination of the 28H1 IgG-IL2 immunoconjugate and the anti-EGFR-GLYCOMAB, or the combination of Proleukin® and the anti-EGFR-GLYCOMAB. The EGFR-GLYCOMAB and the 28H1 IgG-IL2 immunoconjugate were dose once a week for 3 weeks. Proleukin® was injected daily from Monday to Friday for 3 weeks.

All mice were injected i.v. with 200 µl of the appropriate solution. Doses are specified in Table 6. The mice in the vehicle group were injected with PBS and the treatment groups with anti-EGFR-GLYCOMAB, the combination of the 28H1 IgG-IL2 immunoconjugate and the anti-EGFR-GLYCOMAB, or the combination of Proleukin® and the anti-EGFR-GLYCOMAB. To obtain the proper amount of immunoconjugate per 200 µl, the stock solutions were diluted with PBS when necessary.

FIG. 6 and Table 6A show that the combination of the 28H1 IgG-IL2 immunoconjugate and the anti-EGFR-GLYCOMAB mediated superior efficacy in terms of enhanced median and overall survival compared to anti-EGFR-GLYCOMAB alone and the combination of Proleukin® and the anti-EGFR-GLYCOMAB.

TABLE 6

| Compound | Dose | Formulation buffer | Concentration (mg/mL) |
|---|---|---|---|
| Anti-EGFR-GLYCOMAB | 625 µg | 20 mM His/HisCl 240 mM trehalose 0.02% TWEEN (polysorbate) 20, pH 6.0 | 26.65 (=stock solution) |
| 28H1 IgG-IL2 | 78 µg | 20 mM histidine, 140 mM NaCl, pH 6.0 | 3.46 (=stock solution) |
| Proleukin® | 22.2 µg | | 1 (=stock solution) |

TABLE 6A

Summary of survival data corresponding to FIG. 6.

| Treatment | Median survival (days) | Overall survival |
|---|---|---|
| Vehicle | 59 | 0/7 |
| Anti-EGFR GLYCOMAB | 155 | 0/7 |
| Anti-EGFR GLYCOMAB + Proleukin® | 174 | 0/7 |
| 28H1 IgG-IL2 qm + anti-EGFR GLYCOMAB | not reached | 7/7 |

Example 7

In Vitro Boosting of NK Cell Killing Capacity and NK Cell CD25 and CD69 Expression by IL-2 Immunoconjugates As in Example 2, we assessed the killing of tumor cells (LS174T) by NK cells upon treatment with an immunoconjugate, particularly an immunoconjugate comprising IL-2 as effector moiety, and a GLYCOMAB, in this case an anti-Her3 GLYCOMAB. Target cell killing was detected by measuring LDH release into the cell supernatant.

PBMCs were isolated from fresh blood. Briefly, blood was diluted 3:1 with PBS. About 30 ml of the blood/PBS mixture was stacked on 15 ml of Histopaque (Sigma) and centrifuged for 30 min at 450 g for 30 min without brake. The lymphocytes were collected with a 5 ml pipette into 50 ml tubes containing PBS. The tubes were filled up to 50 ml with PBS and centrifuged for 10 min at 350 g. The supernatant was discarded, the pellet re-suspended in 50 ml PBS and centrifuged for 10 min at 300 g. The washing step was repeated once. The cells were counted and re-suspended in pre-warmed RPMI containing 1% glutamine and 10% FCS with $1\times10^6$ cells per ml. The cells were incubated overnight at 37° C. On the next day the cells were harvested and counted.

LS174T (ECACC #87060401) is a human Caucasian colon adenocarcinoma cell line. The cells were cultured in EMEM containing 1% glutamine, 1% non-essential amino acids and 10% FCS and splitted every two to three days before reaching confluence. LS174T cells were detached using trypsin. The cells were counted and viability was checked. The viability of the cells before the assay was 99.4%. The cells were re-suspended in their respective medium at $0.3\times10^6$ per ml. 100 µl of the cell suspension was seeded into a 96 well cell culture treated flat bottom plate and incubated overnight at 37° C. On the next day the supernatant was removed from the cells. Then 50 µl of the diluted anti-Her3 GLYCOMAB (SEQ ID NOs: 142 and 146) at 1000 ng/ml, 100 ng/ml and 10 ng/ml or medium was added to the respective wells. Then, 50 µl of the CEA-targeted CH1A1A IgG-IL2 qm immunoconjugate (SEQ ID NOs: 136-138) at the indicated concentrations (see FIG. 7) or medium was added per well. After 10 minutes incubation at room temperature 100 nl of PBMCs at $3\times10^6$ cells per ml or medium were added to reach a final volume of 200 µl per well. The cells were incubated for 24 hours in the incubator. After the incubation the plate was centrifuged for 4 minutes at 400 g and the supernatant was collected. 50 µl per well of the supernatant were used to measure LDH release (Roche Cytotoxicity Detection Kit LDH). The remaining supernatant was stored at −20° C. until further use. The cells were re-suspended in FACS buffer and stored at 4° C. before starting with the FACS staining (see below)

FIG. 7 shows the overall LS174T cell killing by PBMCs upon treatment with anti-Her3 GLYCOMAB alone (left panel), the CH1A1A IgG-IL-2 qm immunoconjugate alone (right panel) or the combination of the CH1A1A IgG-IL-2 qm immunoconjugate with the anti-Her3 GLYCOMAB (right panel).

The PBMCs were harvested after 24 h and used for FACS analysis of NK cell CD25 and CD69 expression. The cells were centrifuged for 4 min at 400 g and washed once with PBS containing 0.1% BSA (FACS buffer). Then 20 µl per well of the antibody mix was added to the cells. The cells were incubated for 30 min in the fridge. Afterwards the cells were washed twice with FACS buffer and re-suspended in 200 µl FACS buffer containing 2% PFA per well. The analysis was performed using the BD FACS Fortessa, and the following antibody mix: CD3 PE/Cy7 (BioLegend, #300420; diluted 1:40), CD56 APC (BioLegend #318310; diluted 1:20), CD69 Brilliant Violet 421 (BioLegend #310929; diluted 1:40), CD25 PE (BD Bioscience #557138; diluted 1:20).

FIG. 8 shows expression of CD25 (A) or CD69 (B) on NK cells upon treatment with anti-Her3 GLYCOMAB alone (left panel), the CH1A1A IgG-IL-2 qm immunoconjugate alone (right panel) or the combination of the CH1A1A IgG-IL-2 qm immunoconjugate with the anti-Her3 GLYCOMAB (right panel).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a carcinoembryonic antigen (CEA)-expressing or Fibroblast Activation Protein (FAP)-expressing cancer in an individual comprising administering to the individual a combination of:
   (a) an immunoconjugate comprising:
      (i) a first full-length IgG antibody which specifically binds to a CEA antigen or a FAP antigen, wherein the first full-length IgG antibody comprises a human IgG Fc region, and is engineered to have reduced effector function compared to a corresponding non-engineered antibody and comprises in the heavy chain one or more amino acid substitutions selected from the group consisting of S228P, E233P, L234A, L235A, L235E, N297A, N297D, P331S, and P329G according to EU numbering, and
      (ii) a mutant interleukin-2 (IL-2) effector moiety, wherein the mutant IL-2 effector moiety is human IL-2 comprising the amino acid substitutions F42A, Y45A, and L72G according to the amino acid residue positions of SEQ ID NO:1, and
   (b) a second full-length IgG antibody which specifically binds to Epidermal Growth Factor Receptor (EGFR), wherein the second full-length IgG antibody is cetuximab,
   in a therapeutically effective amount.

2. The method of claim 1, wherein the first full-length IgG antibody is an IgG$_1$ antibody.

3. The method of claim 1, wherein the mutant IL-2 effector moiety shares an amino- or carboxy-terminal peptide bond with the first full-length IgG antibody.

4. The method of claim 1, wherein the first full-length IgG antibody is engineered to have reduced binding to an activating Fc receptor, or reduced binding to human FcγRIIIa.

5. The method of claim 1, wherein the first full-length IgG antibody comprises an amino acid substitution at position P329 in the immunoglobulin heavy chains according to EU numbering.

6. The method of claim 1, wherein the first full-length IgG antibody comprises the amino acid substitutions L234A, L235A and P329G in the immunoglobulin heavy chains according to EU numbering.

7. The method of claim 1, wherein the immunoconjugate consists essentially of the mutant IL-2 effector moiety and the first full-length IgG antibody, wherein the mutant IL-2 effector moiety is fused at its amino-terminal amino acid to the carboxy-terminus of one of the heavy chains of the first full-length IgG antibody, optionally through a peptide linker.

8. The method of claim 1, wherein the effector function is selected from the group of binding to an activating Fc receptor, antibody-dependent cell-mediated cytotoxicity (ADCC), antibody-dependent cellular phagocytosis (ADCP), complement-dependent cytotoxicity (CDC), and cytokine secretion.

9. The method of claim 1, wherein the effector function is binding to an activating Fc receptor and/or ADCC.

10. The method of claim 1, wherein the individual is a human.

11. The method of claim 1, wherein the first full-length IgG antibody comprises the heavy chain variable region sequence of SEQ ID NO: 114 and the light chain variable region sequence of SEQ ID NO: 115.

12. The method of claim 1, wherein the first full-length IgG antibody comprises:
   (a) the heavy chain variable region sequence of SEQ ID NO: 12 and the light chain variable region sequence of SEQ ID NO: 11;
   (b) the heavy chain variable region sequence of SEQ ID NO: 17 and the light chain variable region sequence of SEQ ID NO: 16;
   (c) the heavy chain variable region sequence of SEQ ID NO: 47 and the light chain variable region sequence of SEQ ID NO: 46;
   (d) the heavy chain variable region sequence of SEQ ID NO: 63 and the light chain variable region sequence of SEQ ID NO: 62; or
   (e) the heavy chain variable region sequence of SEQ ID NO: 67 and the light chain variable region sequence of SEQ ID NO: 66.

13. The method of claim 1, wherein the mutant IL-2 additionally comprises an amino acid mutation at a position corresponding to position 3 according to the amino acid residue positions of SEQ ID NO:1, which eliminates the O-glycosylation site of IL-2.

14. The method of claim 13, wherein the additional amino acid mutation is an amino acid substitution replacing a threonine residue with an alanine residue.

15. The method of claim 1, wherein the mutant IL-2 comprises the sequence of SEQ ID NO: 2.

16. The method of claim 1, wherein the cancer is selected from the group consisting of lung cancer, colorectal cancer, renal cancer, and head and neck cancer.

17. The method of claim 1, wherein the first full-length IgG antibody binds to CEA and comprises:
   a) in the heavy chain variable domain a CDR1 of SEQ ID NO: 108, a CDR2 of SEQ ID NO: 109, and a CDR3 of SEQ ID NO: 110, and
   b) in the light chain variable domain a CDR1 of SEQ ID NO: 111, a CDR2 of SEQ ID NO: 112, and a CDR3 of SEQ ID NO: 113.

18. The method of claim 1, wherein the human IgG Fc region of the first full-length IgG antibody is a human IgG1 Fc region.

19. A method of stimulating effector cell function in an individual having a carcinoembryonic antigen (CEA)-expressing or Fibroblast Activation Protein (FAP)-expressing cancer, comprising administering to the individual a combination of
   (a) an immunoconjugate comprising:
      (i) a first full-length IgG antibody which specifically binds to a CEA antigen or a FAP antigen, wherein the first full-length IgG antibody comprises a human IgG Fc region, and is engineered to have reduced effector function compared to a corresponding non-engineered antibody and comprises in the heavy chain one or more amino acid substitutions selected from the group consisting of S228P, E233P, L234A, L235A, L235E, N297A, N297D, P331S, and P329G according to EU numbering, and
      (ii) a mutant interleukin-2 (IL-2) effector moiety, wherein the mutant IL-2 effector is human IL-2 comprising the amino acid substitutions F42A, Y45A, and L72G according to the amino acid residue positions of SEQ ID NO:1, and
   (b) a second full-length IgG antibody which specifically binds to Epidermal Growth Factor Receptor (EGFR), wherein the second full-length IgG antibody is cetuximab,
in an amount effective to stimulate effector cell function.

20. The method of claim 19, wherein the first full-length IgG antibody binds to CEA and comprises:
   a) in the heavy chain variable domain a CDR1 of SEQ ID NO: 108, a CDR2 of SEQ ID NO: 109, and a CDR3 of SEQ ID NO: 110, and
   b) in the light chain variable domain a CDR1 of SEQ ID NO: 111, a CDR2 of SEQ ID NO: 112, and a CDR3 of SEQ ID NO: 113.

21. The method of claim 19, wherein the first full-length IgG antibody comprises the heavy chain variable region sequence of SEQ ID NO: 114 and the light chain variable region sequence of SEQ ID NO: 115.

22. The method of claim 19, wherein the mutant IL-2 comprises the sequence of SEQ ID NO: 2.

* * * * *